US012570654B2

(12) United States Patent
Binkowski et al.

(10) Patent No.: US 12,570,654 B2
(45) Date of Patent: Mar. 10, 2026

(54) NANOLUC SUICIDE SUBSTRATES

(71) Applicant: PROMEGA CORPORATION, Madison, WI (US)

(72) Inventors: Brock Binkowski, Sauk City, WI (US); Mary P. Hall, Waunakee, WI (US); Thomas Machleidt, Madison, WI (US); Joel Walker, San Luis Obispo, CA (US); Wenhui Zhou, San Luis Obispo, CA (US)

(73) Assignee: PROMEGA CORPORATION, Madison, WI (US)

( * ) Notice: Subject to any disclaimer, the term of this patent is extended or adjusted under 35 U.S.C. 154(b) by 517 days.

(21) Appl. No.: 18/296,203

(22) Filed: Apr. 5, 2023

(65) Prior Publication Data

US 2023/0382908 A1 Nov. 30, 2023

Related U.S. Application Data

(62) Division of application No. 16/399,410, filed on Apr. 30, 2019, now Pat. No. 11,655,247.

(60) Provisional application No. 62/665,346, filed on May 1, 2018.

(51) Int. Cl.

| | |
|---|---|
| ***C07D 471/04*** | (2006.01) |
| ***C07D 519/00*** | (2006.01) |
| ***C12Q 1/66*** | (2006.01) |
| ***G01N 33/52*** | (2006.01) |
| ***G01N 33/533*** | (2006.01) |
| ***G01N 33/542*** | (2006.01) |

(52) U.S. Cl.

CPC ......... *C07D 471/04* (2013.01); *C07D 519/00* (2013.01); *C12Q 1/66* (2013.01); *G01N 33/52* (2013.01); *G01N 33/533* (2013.01); *G01N 33/542* (2013.01); *G01N 2458/15* (2013.01)

(58) Field of Classification Search

CPC ...... C07D 471/04; C07D 519/00; C12Q 1/66; G01N 33/52; G01N 33/533; G01N 33/542; G01N 2458/15

USPC .................................................... 252/301.16

See application file for complete search history.

(56) References Cited

U.S. PATENT DOCUMENTS

| | | | |
|---|---|---|---|
| 8,557,970 | B2 | 10/2013 | Encell et al. |
| 8,669,103 | B2 | 3/2014 | Binkowski et al. |
| 2008/0248511 | A1 | 10/2008 | Daily et al. |
| 2011/0275134 | A1 | 11/2011 | Bouvier et al. |
| 2012/0107849 | A1 | 5/2012 | Klaubert et al. |
| 2012/0117667 | A1 | 5/2012 | Klaubert et al. |

(Continued)

FOREIGN PATENT DOCUMENTS

| | | |
|---|---|---|
| WO | WO 2003/040100 | 5/2003 |
| WO | WO 2012/061529 | 5/2012 |

(Continued)

OTHER PUBLICATIONS

Adamczyk et al., "Synthesis of 3,7-dihydroimidazo[1,2a]pyrazine-3-ones and their chemiluminescent properties," *Tetrahedron*, vol. 59, No. 41, pp. 8129-8142 (Oct. 6, 2003).

(Continued)

*Primary Examiner* — Anita Nassiri-Motlagh

(74) *Attorney, Agent, or Firm* — Casimir Jones, S.C.; Anne M. Reynolds

(57) ABSTRACT

Compounds that may inhibit *Oplophorus*-derived luciferases are disclosed as well as compositions and kits comprising the compounds and methods of using the compounds.

23 Claims, 19 Drawing Sheets

Specification includes a Sequence Listing.

(56) References Cited

U.S. PATENT DOCUMENTS

| | | | |
|---|---|---|---|
| 2013/0130289 | A1 | 5/2013 | Benink et al. |
| 2013/0230466 | A1 | 9/2013 | Hermanson et al. |
| 2015/0212078 | A1 | 7/2015 | Zhou et al. |
| 2015/0307916 | A1 | 10/2015 | Zhou et al. |
| 2016/0002703 | A1 | 1/2016 | Klaubert et al. |
| 2016/0376568 | A1 | 12/2016 | Duellman et al. |
| 2017/0233789 | A1 | 8/2017 | Shakhmin et al. |
| 2018/0030059 | A1 | 2/2018 | Hall et al. |
| 2018/0119200 | A1 | 5/2018 | Hall et al. |
| 2018/0155350 | A1 | 6/2018 | Hall et al. |
| 2018/0223330 | A1 | 8/2018 | Shakhmin et al. |
| 2018/0334463 | A1 | 11/2018 | Hall et al. |

FOREIGN PATENT DOCUMENTS

| | | |
|---|---|---|
| WO | WO 2012/061530 | 5/2012 |
| WO | WO 2013/078244 | 5/2013 |
| WO | WO 2018/102693 | 6/2018 |

OTHER PUBLICATIONS

Chou et al. "Chemical synthesis of coelenterazine and its analogs: new route by four segment-couplings," *Heterocycles*, 2012, vol. 86, No. 2, pp. 1323-1339.

Hall et al., "Engineered Luciferase Reporter from a Deep Sea Shrimp Utilizing a Novel Imidazopyrazinone Substrate," *ACS Chemical Biology*, 2012, vol. 7, No. 11, pp. 1848-1857.

Hirayama et al., "Fluorogenic probes reveal a role of GLUT4 N-glycosylation in intracellular trafficking," *Nature Chemical Biology*, 2016, vol. 12, pp. 853-859, plus supporting information.

International Search Report and Written Opinion of PCT/US2019/029975, mailed Jul. 4, 2019 (11 pages).

Kojima et al., "Rational Design and Development of Near-Infrared Emitting Firefly Luciferins Available In Vivo," *Angewandte Chemie International Edition*, 2013, vol. 52, issue 4, pp. 1175-1179.

Lavis et al., "Bright Building Blocks for Chemical Biology," *ACS Chemical Biology*, 2014, vol. 9, issue 4, pp. 855-866.

Lindberg et al., "Development of cell-impermeable coelenterazine derivatives," *Chemical Science*, 2013, vol. 4, No. 12, p. 4395-4400, plus supporting information.

Nishihara et al. "Azide- and dye-conjugated coelenterazine analogues for a multiplex molecular imaging platform" *Bioconjugate Chemistry*, 2018, vol. 29, No. 6, pp. 1922-1931.

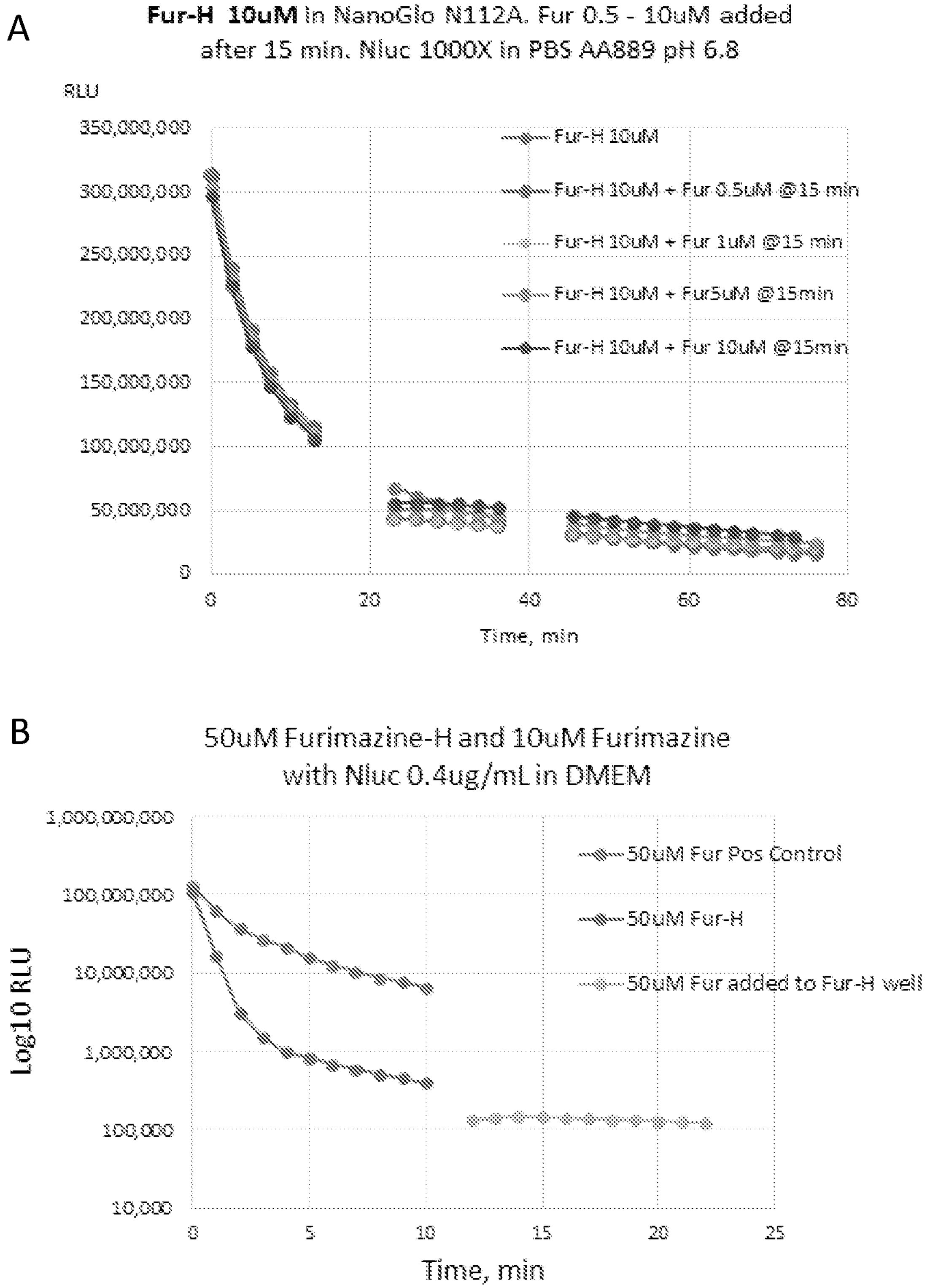
FIGS. 3A-B

A.
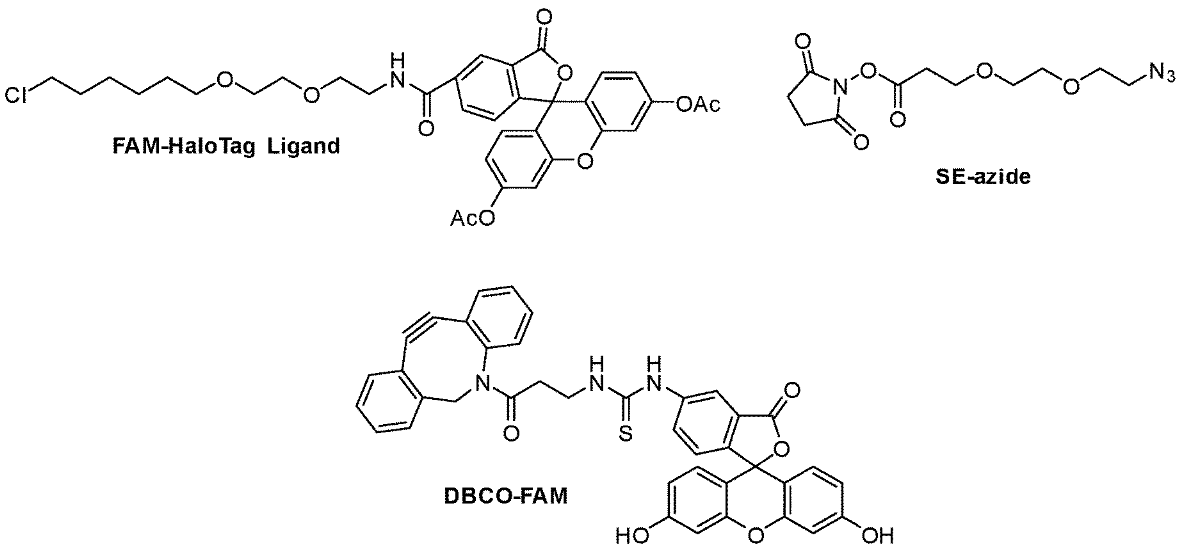
FAM-HaloTag Ligand
SE-azide
DBCO-FAM
B.
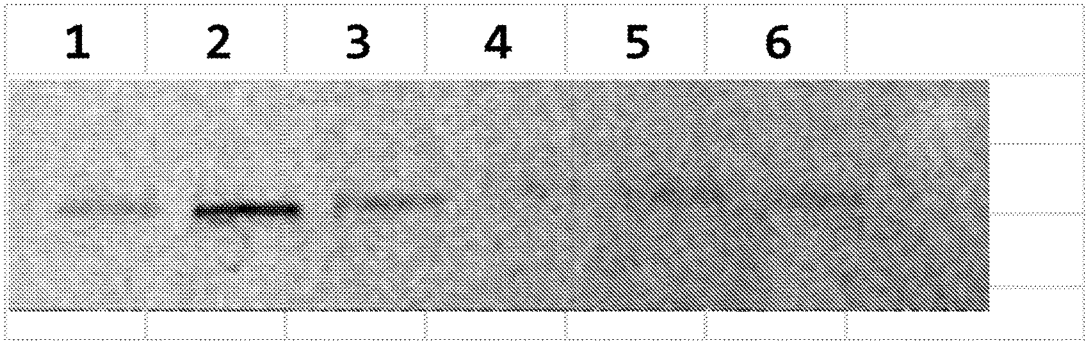
FIGS. 10A-B

A.
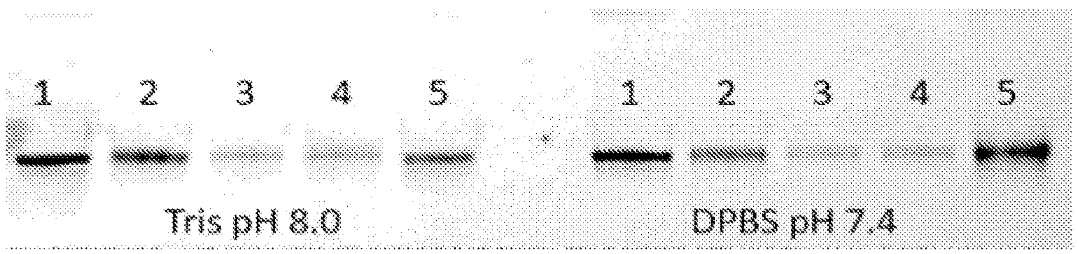
B.
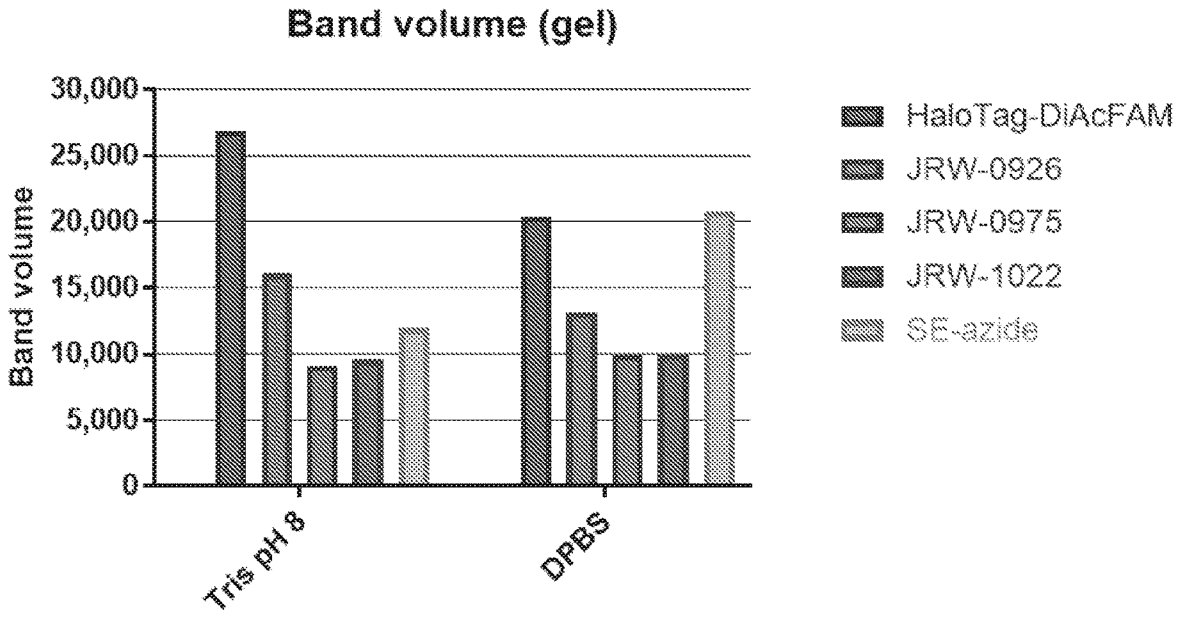
FIGS. 11A-B

A.
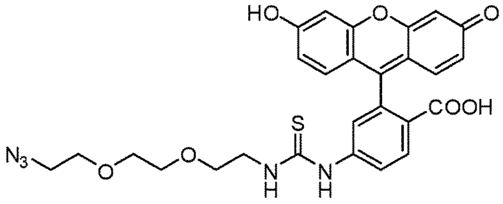
Azide-FAM
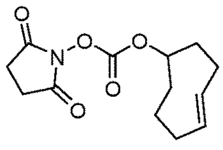
SE-TCO
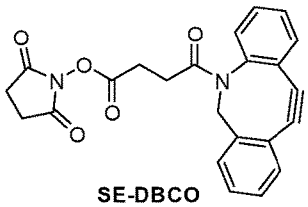
SE-DBCO
B.
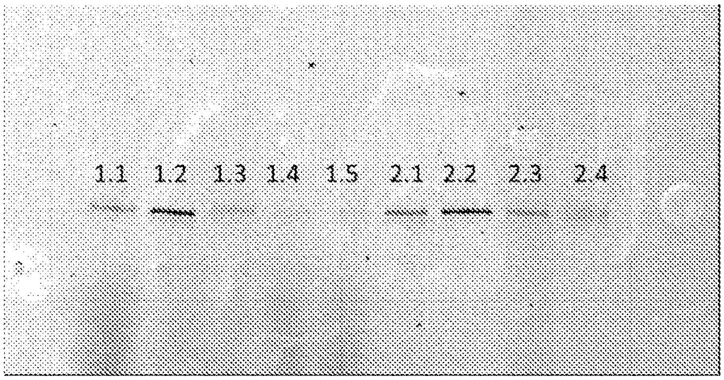
1.1 JRW-1550, 1 hour, Azide-FAM 4 hour
1.2 HT DiAcFAM, 1 hour
1.3 JRW-1022, 1 hour, DBCO-FAM, 4 hour
1.4 JRW-1549, 1 hour, Azide-FAM, 4 hour
1.5 SE-DBCO 1 hour, Azide-FAM, 4 hour
2.1 JRW-1567, 1 hour, JRW-1577, 4 hour
2.2 HT DiAcFAM, 1 hour
2.3 JRW-1566, 1 hour, JRW-1577, 4 hour
2.4 SE-TCO, 1 hour, JRW-1577, 4 hour
C.
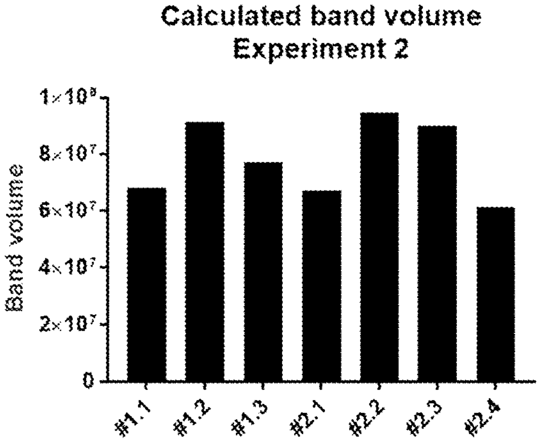
| Sample | Normalized |
|---|---|
| #1.1 | 0.7 |
| #1.2 | 1.0 |
| #1.3 | 0.8 |
| #2.1 | 0.7 |
| #2.2 | 1.0 |
| #2.3 | 1.0 |
| #2.4 | 0.7 |
FIGS. 12A-C

NANOLUC SUICIDE SUBSTRATES

CROSS-REFERENCE TO RELATED APPLICATIONS

The present application is a divisional of U.S. patent application Ser. No. 16/399,410, filed on Apr. 30, 2019, which claims the priority benefit of U.S. Provisional Patent Application Ser. No. 62/665,346, filed on May 1, 2018, which is incorporated herein by reference in its entirety.

SEQUENCE LISTING STATEMENT

The contents of the electronic sequence listing titled (PRMG-37070.404.xml; Size: 6,091 bytes; and Date of Creation: Apr. 5, 2023) is herein incorporated by reference in its entirety.

TECHNICAL FIELD

The present disclosure is directed to compounds that may be used to detect or inhibit *Oplophorus*-derived luciferases.

BACKGROUND

Reporter molecules are routinely used to monitor molecular events in the fields of biology, biochemistry, immunology, cell biology, and molecular biology. Luciferases based on the luciferase secreted from the deep-sea shrimp, *Oplophorus gracilirostris*, may be used as reporter molecules and have been shown to have advantageous characteristics including broad substrate specificity, high activity, and high quantum yield. It may be further advantageous, in certain applications, to label or to control the luminescent signal from *Oplophorus* luciferases.

SUMMARY

In one aspect, the disclosure provides a compound of formula (I), or a salt thereof:

(I)

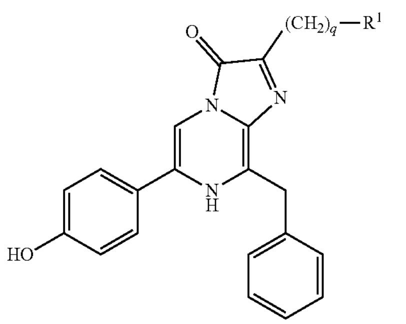

or a tautomer or a salt thereof, wherein:

$R^1$ is optionally substituted aryl, optionally substituted heteroaryl, optionally substituted heterocycle, or optionally substituted cycloalkyl, wherein $R^1$ is substituted with at least one group that is -Q-L-Z;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y}$—$CR^{1x}R^{1y}$—$O)_{t1}$—$(CR^{1x}R^{1y})_{t2}$-$Q^1$-, —$(CR^{1x}R^{1y})_{t2}$-A-$(CR^{1x}R^{1y}$—$CR^{1x}R^{1y}$—$O)_{t1}$-$Q^1$-, —$(CR^{1x}R^{1y})_{t3}$-A-$(CR^{1x}R^{1y}$—$CR^{1x}R^{1y}$—$O)_{t1}$—$(CR^{1x}R^{1y})_{t2}$—, or —$(CR^{1x}R^{1y})_{t3}$-A-$(CR^{1x}R^{1y})_{t4}$—, wherein each $Q^1$ is independently a bond, —O—, or —$NR^{Q1}$—, and each A is independently a bond, —O—, —$NR^Q$—, —$NR^Q$—CO—, —CO—$NR^Q$—, —O—CO—$NR^Q$—, or —$NR^Q$—CO—O—;

Z is —$COOR^2$, —$SO_2$—$OR^3$, —$PO(OR^4)(OR^5)$, halo, azide, $C_2$-$C_{10}$ alkynyl, a biotin moiety, —$NR^6R^7$, —$NR^8$—CO—$R^9$, —CO—$R^{10}$, or —$NR^{11}$—CO—O—$R^{12}$;

$R^2$, $R^3$, $R^4$, $R^5$, $R^8$, $R^9$, $R^{10}$, $R^{11}$, and $R^{12}$ at each occurrence are independently hydrogen, optionally substituted $C_1$-$C_8$ alkyl, optionally substituted aryl, optionally substituted cycloalkyl, optionally substituted cycloalkenyl, optionally substituted heteroaryl, optionally substituted heterocycle, optionally substituted heteroalkyl, or an energy acceptor;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1, 2, 3, 4, 5, 6, 7, 8, 9, 10, 11, or 12;

t1 at each occurrence is independently 1, 2, 3, 4, 5, 6, 7, 8, 9, or 10; and t2 is an integer from 0-5;

t3 at each occurrence is 1, 2, 3, 4, 5, 6, 7, 8, 9, or 10; and t4 is an integer from 0-5, wherein the compound is not 4-[4-[[8-benzyl-6-(4-hydroxyphenyl)-3-oxo-7H-imidazo[1,2-a]pyrazin-2-yl]methyl]phenoxy]butanoic acid.

In one aspect, the disclosure provides a method of labeling an *Oplophorus*-derived luciferase in a sample, the method comprising contacting the *Oplophorus*-derived luciferase with a compound described herein.

In one aspect, the disclosure provides a method of labeling an *Oplophorus*-derived luciferase in a sample, the method comprising (a) contacting the sample with a compound disclosed herein; and (b) detecting luminescence in the sample.

In one aspect, the disclosure provides a method of detecting an *Oplophorus*-derived luciferase in a sample, the method comprising contacting the sample with a compound described herein, such as a compound of formula (I).

In one aspect, the disclosure provides a method of detecting luminescence in a sample, the method comprising:

(a) contacting the sample with a compound described herein, such as a compound of formula (I);

(b) contacting the sample with an *Oplophorus*-derived luciferase, if it is not present in the sample; and (c) detecting luminescence in the sample.

In one aspect, the disclosure provides a method of labeling an *Oplophorus*-derived luciferase in a sample, the method comprising contacting the sample with a compound described herein, such as a compound of formula (I).

In one aspect, the disclosure provides a method of labeling an *Oplophorus*-derived luciferase in a sample, the method comprising:

(a) contacting the sample with a compound described herein, such as a compound of formula (I), wherein the compound includes at least one fluorescent dye;

(b) washing the sample after the contacting step to remove any unreacted or degraded compound; and (c) detecting fluorescence in the sample after the washing step.

In one aspect, the disclosure provides a method of labeling an *Oplophorus*-derived luciferase in a sample, the method comprising:

(a) contacting the sample with a compound described herein, such as a compound of formula (I), wherein the compound includes a first functional group;

(b) washing the sample to remove any unreacted or degraded compound;

(c) contacting the sample with a fluorescent dye that includes a second functional group, wherein the second functional group can react with or bind to the first functional group;

(d) washing the sample to remove any unreacted fluorescent dye; and (e) detecting fluorescence in the sample.

In one aspect, the disclosure provides a method of isolating an *Oplophorus*-derived luciferase from a sample, wherein the sample comprises live cells, the method comprising:

(a) contacting a live cell sample comprising an *Oplophorus*-derived luciferase with a compound described herein, such as a compound of formula (I), wherein the compound has a first functional group;

(b) washing the sample to remove any unreacted or degraded compound;

(c) contacting the sample with one or more lysis reagents;

(d) adding to the sample a capturing agent having a second functional group that binds to or reacts with the first functional group, to capture the *Oplophorus*-derived luciferase;

(e) washing the sample to remove uncaptured *Oplophorus*-derived luciferase; and (f) isolating the *Oplophorus*-derived luciferase captured in step (e).

In one aspect, the disclosure provides a method of isolating an *Oplophorus*-derived luciferase from a sample, wherein the sample comprises live cells, the method comprising:

(a) contacting a sample comprising an *Oplophorus*-derived luciferase with one or more lysis reagents;

(b) contacting a live cell sample comprising an *Oplophorus*-derived luciferase with a compound described herein, such as a compound of formula (I), wherein the compound has a first functional group;

(c) washing the sample to remove any unreacted or degraded compound;

(d) adding to the sample a capturing agent having a second functional group that binds to or reacts with the first functional group, to capture the *Oplophorus*-derived luciferase;

(e) washing the sample to remove uncaptured *Oplophorus*-derived luciferase; and (f) isolating the *Oplophorus*-derived luciferase captured in step (e).

In one aspect, the disclosure provides a method of inhibiting an *Oplophorus*-derived luciferase, the method comprising contacting the *Oplophorus*-derived luciferase with a compound described herein, such as a compound of formula (I).

In one aspect, the disclosure provides a method of modulating luminescence of an *Oplophorus*-derived luciferase in a sample, the method comprising, (a) contacting the sample with a coelenterazine substrate and a compound described herein, such as a compound of formula (I), and (b) detecting luminescence in the sample, wherein the compound causes a decrease in the luminescence from the *Oplophorus*-derived luciferase.

In one aspect, the disclosure provides a kit comprising:

(a) a compound described herein, such as a compound of formula (I); and (b) an *Oplophorus*-derived luciferase.

BRIEF DESCRIPTION OF THE DRAWINGS

FIGS. 3A-B show NanoLuc® luciferase (Nluc) treated with furimazine-h becomes unresponsive to various concentrations of furimazine.

FIGS. 10A-B show results of a two-step labeling process using a substrate having an appended azide followed by reaction with an alkyne compound having an appended FAM dye.

FIGS. 11A-B show results of a two-step labeling process using a substrate having an appended azide followed by reaction with an alkyne compound having an appended FAM dye.

FIGS. 12A-C show results of an additional two-step labeling process using an alkene-tetrazine pair.

DETAILED DESCRIPTION

Figure 1:
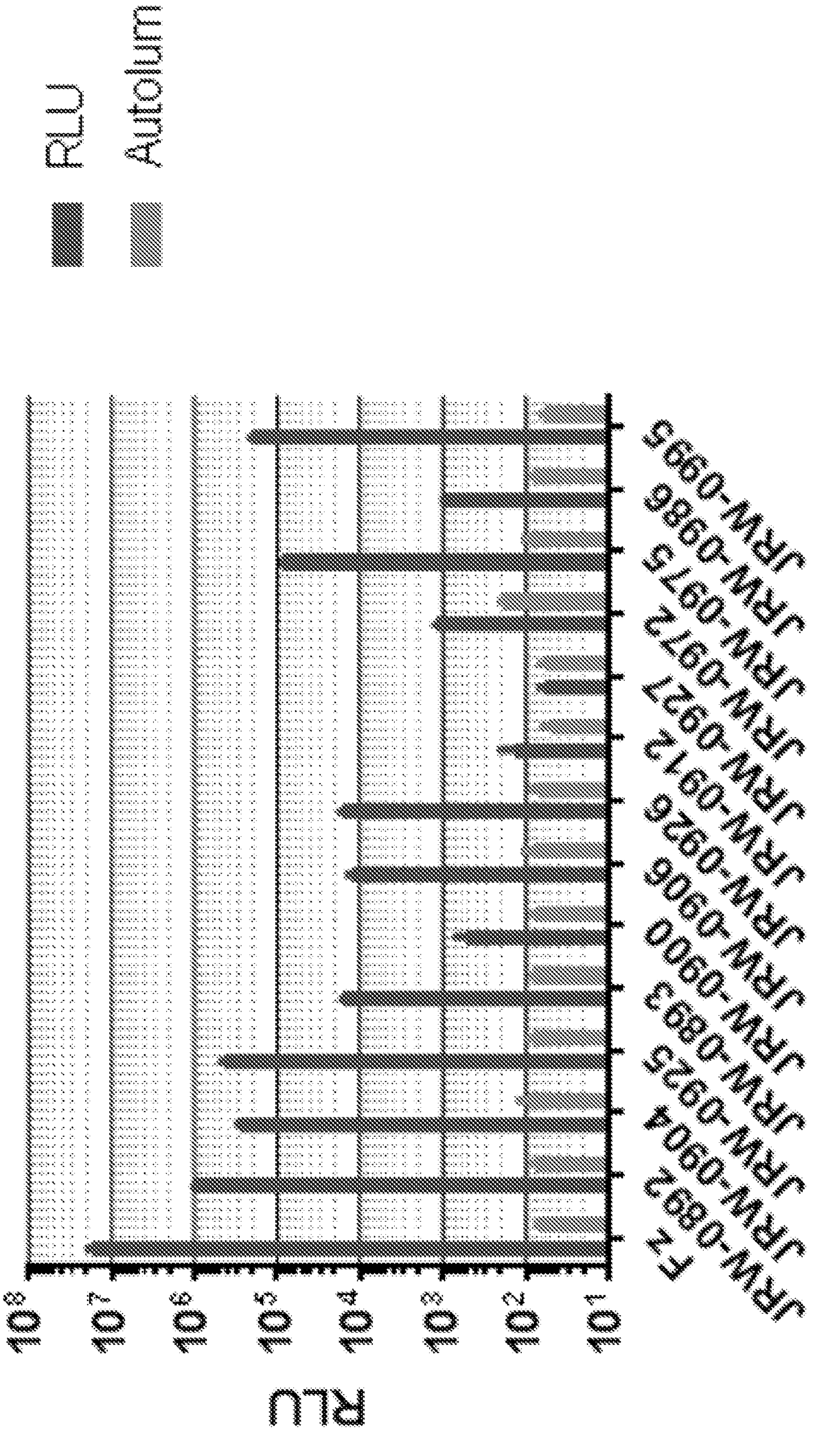
FIG. 1 shows biochemical bioluminescent activity and autoluminescent activity of exemplary compounds in comparison to furimazine (Fz).

Disclosed herein are coelenterazine analogues. The disclosed compounds may include a coelenterazine analog core, a covalent chain linker, and a functional group. The coelenterazine analog core may bind to a luciferase at the enzyme's binding site. The compounds may be useful as labeling reagents for *Oplophorus*-derived luciferases such as suicide inhibitors. When the compounds further include a covalently-tethered functional group, they may further be used to detect *Oplophorus*-derived luciferases. The disclosed compounds may be selective substrates to *Oplophorus*-derived luciferases, such as a luciferase of SEQ ID NO:2 (also interchangeably referred to herein as "NanoLuc," "Nluc," "Nluc luciferase," and "Nluc enzyme").

The disclosed compounds may be inhibitors of *Oplophorus*-derived luciferases. The disclosed compounds may selectively inhibit *Oplophorus*-derived luciferases, such as a luciferase of SEQ ID NO:2 (also interchangeably referred to herein as "NanoLuc," "Nluc," "Nluc luciferase," and "Nluc enzyme"). The disclosed compounds may be suicide inhibitors, which irreversibly inhibit the luciferase activity of the *Oplophorus*-derived luciferases. The disclosed compounds may be partial inhibitors which partially reduce the luciferase activity of the *Oplophorus*-derived luciferases. The disclosed compounds may be suicide substrates of *Oplophorus*-derived luciferase, which initially produce a bioluminescent signal upon reaction with the luciferase and subsequently irreversibly inhibit the *Oplophorus*-derived luciferase. The disclosed compounds may inhibit NanoLuc as well as the NanoBiT complementary enzyme system.

The disclosed compounds may be appended to a fluorescent dye or chromophore for use in live cell imaging, cell sorting, or histogram stain. The disclosed compounds may be used for the capture or immobilization of NanoLuc-fused protein of interests on surface or solids. The disclosed compounds may be appended to various biomolecules and used for post-labeling of NanoLuc or NanoBiT with appropriate functional groups. The disclosed compounds may be used in a two-step method to fluorescently label NanoLuc. For example, the disclosed compounds may be appended to a reactive functional group and a fluorescent dye with a complementary reactive group could be added to fluorescently label NanoLuc. In an exemplary embodiment, the disclosed compounds may include an azide and a fluorescent dye conjugated to an alkyne could be added to fluorescently label NanoLuc.

The disclosed compounds may be modified to produce both cell-permeable and cell-impermeable compounds. Due to their stabilities and their potential to be excreted from cells, it may be advantageous to use selective inhibitors to suppress the luminescence from *Oplophorus*-derived luciferases in certain applications. For example, in applications involving temporal multiplexing of multiple luminescent systems, it can be beneficial to have selective inhibitors for each system to allow for the measurement and/or detection of only one luminescent signal at a time. Additionally, in some plate-based assays, a certain amount of luciferase may be excreted from cells. An extracellular inhibitor compound would allow for luminescence from excreted luciferase to be selectively suppressed and may, therefore, help to improve the signal-to-noise ratio in certain assays.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene" as used herein, refers to a divalent group derived from a straight or branched chain hydrocarbon of 1 to 10 carbon atoms, for example, of 2 to 5 carbon atoms. Representative examples of alkylene include, but are not limited to, $-CH_2CH_2-$, $-CH_2CH_2CH_2-$, $-CH_2CH_2CH_2CH_2-$, and $-CH_2CH_2CH_2CH_2CH_2-$.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "biotin moiety," as used herein, refers to a radical of biotin or a portion thereof. For example, a biotin moiety may include the bicyclic heterocyclic ring ((3aR, 6aS)-tetrahydro-1H-thieno[3,4-d]imidazol-2(3H)-one) that is directly attached to the remainder of the molecule (e.g., at the 4-position of the ring system), or the biotin moiety may include one or more of the four methylene groups naturally occurring in biotin that link the 4-position of the bicyclic heterocyclic ring to the biotin —COOH group, or the biotin moiety may include the bicyclic heterocycle along with the four methylene groups and a —C(O)— or —CO(O)— group. In some embodiments, a biotin moiety may have any of the following formulae:

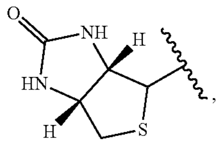
,
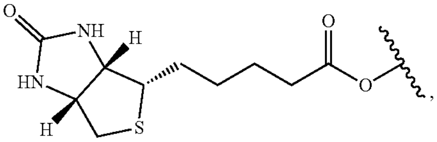
,
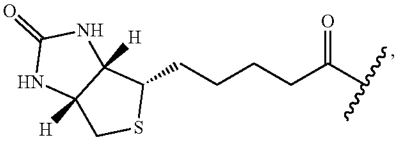
, or
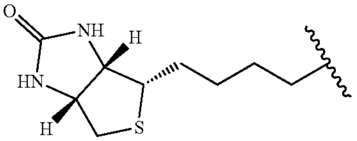

The term "cycloalkyl" as used herein, refers to a carbocyclic ring system containing three to ten carbon atoms and zero heteroatoms, and optionally containing 1 or 2 double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven, or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P, and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds, and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.$1^{3,7}$]decane), and oxa-adamantane (2-oxatricyclo[3.3.1.$1^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

As used herein, the term "halogen" or "halo" refers to a fluoro, chloro, bromo, or iodo radical.

As used herein, the term "bioluminescence" or "luminescence" may refer to light produced as a result of a reaction between an enzyme and a substrate that generates light. Examples of such enzymes (bioluminescent enzymes) include *Oplophorus* luciferase, e.g., *Oplophorous gracilirostris*, firefly luciferase, e.g. *Photinus pyralis* or *Photuris pennsylvanica*, click beetle luciferase, *Renilla* luciferase, cypridina luciferase, Aequorin photoprotein, obelin photoprotein, and the like.

As used herein, the term "bioactive agent" may refer to a molecule or a functional component of a molecule that is capable of interacting with a biological molecule (such as proteins and nucleic acids) and cause a change in the biological activity of the biological molecule. For example, the biological molecule may function as an enzyme, a transporter, or a receptor that regulates the signal transduction, metabolism, and other biological processes in a cell. The bioactive agent may enhance or inhibit the activity of such biological molecule. The bioactive agent may include, for example, a pharmaceutical agent for a disease or disorder, an enzyme inhibitor, or an inhibitor of a cellular receptor. Suitable bioactive agent may include a kinase inhibitor such as dasatinib. The bioactive agent may also include proteins and surfaces that interact with a biological molecule. For example, the bioactive agent may include a protein such as HaloTag® proteins.

As used herein, the term "capturing agent" refers to an agent that is capable of capturing a protein from a sample. For example, the capturing agent may be a bead or a surface that includes a functional group that is capable of binding to or reacting with a functional group of a protein of interest in a sample. An exemplary capturing agent includes streptavidin beads or streptavidin coated surfaces.

As used herein, the term "coelenterazine substrate" refers to a class of reporter molecules that luminesce when acted upon by a wide variety of bioluminescent proteins such as luciferases (e.g., marine luciferases). Coelenterazine substrates include coelenterazine as well as analogs and derivatives thereof.

The term "energy acceptor" or "acceptor molecule" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog). In certain embodiments, energy acceptors include but are not limited to small molecule fluorescent dyes such as NCT, quenchers, fluorescent particles such as Quantum dots, luminescent metal complexes, and any other known energy acceptors.

The term "luminescent enzyme," "bioluminescent enzyme," or "luciferase" as used interchangeably herein refers to a class of oxidative enzymes used in bioluminescence wherein the enzyme produces and emits light when given a substrate. The luciferase may be a naturally occurring, recombinant, or mutant luciferase that uses a luciferase substrate. The luciferase substrate may be luciferin, a luciferin derivative or analog, a pre-luciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as Aequorin, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the terms "*Oplophorus* luciferase" and "*Oplophorus*-derived luciferase" are used interchangeably and refer to a luciferase secreted from the deep-sea shrimp *Oplophorus gracilirostris* (e.g., SEQ ID NO: 1), including wild-type, variants, and mutants thereof. For example, suitable *Oplophorus* luciferase variants are described in U.S. Pat. Nos. 8,557,970 and 8,669,103, each of which is incorporated herein by reference in its entirety. Exemplary *Oplophorus*-derived luciferases include, for example, that of SEQ ID NO: 2 (also interchangeably referred to herein as "NanoLuc," "Nluc," "Nluc luciferase," and "Nluc enzyme").

As used herein, the term "reporter moiety" may refer to a moiety that, under appropriate conditions, directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, napthyl luciferin, fluorolucifeirn, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a fluorophore, such as coumarin, R110, fluorescein, DDAO, resorufin, cresyl violet, sily xanthene, or carbopyronine. Fluorescence may be detected using a fluorimeter.

As used herein, "suicide substrate" or "labeling reagent" refers to a compound that binds to an *Oplophorus* luciferase, undergoes catalysis and releases light, and then inhibits the *Oplophorus* luciferase. The suicide substrate may inhibit the *Oplophorus* luciferase by forming a covalent adduct with the *Oplophorus* luciferase.

When methods are described herein by describing certain method steps, (e.g., (a), (b), (c), etc.), it is understood that the method steps are performed in the order in which they are listed. For example, if a method lists steps (a), (b), and (c) in that order, then it will be understood that steps (a), (b) and (c) are performed sequentially in the order listed.

2. COMPOUNDS

Provided herein are compounds that may label/detect *Oplophorus*-derived luciferases and/or *Oplophorus*-derived luciferase activity. Provided herein are compounds that may inhibit *Oplophorus*-derived luciferases and/or *Oplophorus*-derived luciferase activity. The disclosed compounds may be inhibitors of *Oplophorus*-derived luciferases. The disclosed compounds may be suicide inhibitors which irreversibly inhibit the luciferase activity of the *Oplophorus*-derived luciferases. The disclosed compounds may be partial inhibitors which partially reduce the luciferase activity of the *Oplophorus*-derived luciferases. The disclosed compounds may be substrates of *Oplophorus*-derived luciferases. The disclosed compounds may be substrates of *Oplophorus*-derived luciferase which initially produce a bioluminescent signal upon reaction with the luciferase and subsequently inhibit the *Oplophorus*-derived luciferase. For example, the disclosed compounds may initially produce a bioluminescent signal upon reaction with the luciferase and subsequently inhibit the bioluminescent signal generated upon addition of a coelenterazine substrate to the *Oplophorus*-derived luciferase. The disclosed compounds may be suicide substrates of *Oplophorus*-derived luciferase which initially produce a bioluminescent signal upon reaction with the luciferase and subsequently irreversibly inhibit the *Oplophorus*-derived luciferase. The disclosed compounds may be substrates of *Oplophorus*-derived luciferase which initially produce a bioluminescent signal upon reaction with the luciferase and subsequently partially inhibit the *Oplophorus*-derived luciferase. The disclosed compounds may inhibit the *Oplophorus*-derived luciferase by forming a covalent adduct with the *Oplophorus*-derived luciferase. The disclosed compounds may inhibit NanoLuc as well as the NanoBiT complementary enzyme system.

The present compounds include compounds of formula (I):

(I)

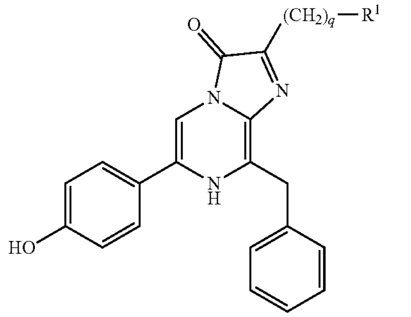

or a tautomer or a salt thereof, wherein:

$R^1$ is optionally substituted aryl, optionally substituted heteroaryl, optionally substituted heterocycle, or optionally substituted cycloalkyl, wherein $R^1$ is substituted with at least one group that is -Q-L-Z;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y}$—$CR^{1x}R^{1y}$—$O)_{t1}$—$(CR^{1x}R^{1y})_{t2}$-$Q^1$-, —$(CR^{1x}R^{1y})_{t2}$-A-$(CR^{1x}R^{1y}$—$CR^{1x}R^{1y}$—$O)_{t1}$-$Q^1$-, —$(CR^{1x}R^{1y})_{t3}$-A-$(CR^{1x}R^{1y}$—$CR^{1x}R^{1y}$—$O)_{t1}$—$(CR^{1x}R^{1y})_{t2}$—, or —$(CR^{1x}R^{1y})_{t3}$-A-$(CR^{1x}R^{1y})_{t4}$—, wherein each $Q^1$ is independently a bond, —O—, or —$NR^{Q1}$—, and each A is independently a bond, —O—, —$NR^Q$—, —$NR^Q$—CO—, —CO—$NR^Q$—, —O—CO—$NR^Q$—, or —$NR^Q$—CO—O—;

Z is —$COOR^2$, —$SO_2$—$OR^3$, —$PO(OR^4)(OR^5)$, halo, azide, —$NR^6R^7$, —$NR^8$—CO—$R^9$, —CO—$R^{10}$, or —$NR^{11}$—CO—O—$R^{12}$;

$R^2$, $R^3$, $R^4$, $R^5$, $R^8$, $R^9$, $R^{10}$, $R^{11}$, and $R^{12}$ at each occurrence are independently hydrogen, optionally substituted $C_1$-$C_8$ alkyl, optionally substituted aryl, optionally substituted cycloalkyl, optionally substituted cycloalkenyl, optionally substituted heteroaryl, optionally substituted heterocycle, optionally substituted heteroalkyl, or an energy acceptor;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1, 2, 3, 4, 5, 6, 7, 8, 9, 10, 11, or 12;

t1 at each occurrence is independently 1, 2, 3, 4, 5, 6, 7, 8, 9, or 10;

t2 is an integer from 0-5;

t3 at each occurrence is 1, 2, 3, 4, 5, 6, 7, 8, 9, or 10; and t4 is an integer from 0-5, wherein the compound is not 4-[4-[[8-benzyl-6-(4-hydroxyphenyl)-3-oxo-7H-imidazo[1,2-a]pyrazin-2-yl]methyl]phenoxy]butanoic acid.

In some embodiments, the compound is a compound of formula (I'):

(I')

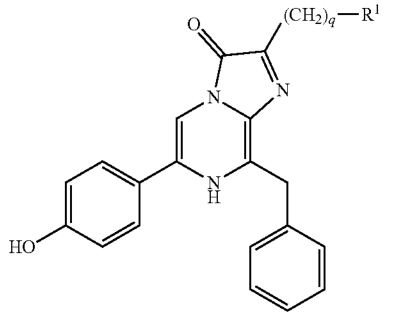

or a tautomer or a salt thereof, wherein:

$R^1$ is optionally substituted aryl, optionally substituted heteroaryl, optionally substituted heterocycle, or optionally substituted cycloalkyl, wherein $R^1$ is substituted with at least one group that is -Q-L-Z;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y}$—$CR^{1x}R^{1y}$—$O)_{t1}$—$(CR^{1x}R^{1y})_{t2}$-$Q^1$-, or —$(CR^{1x}R^{1y})_{t2}$-A-$(CR^{1x}R^{1y}$—$CR^{1x}R^{1y}$—$O)_{t1}$-$Q^1$-, wherein each $Q^1$ is independently a bond, —O—, or —$NR^{Q1}$—, and A is a bond, —O—, —$NR^Q$—, —$NR^Q$—CO—, —CO—$NR^Q$—, —O—CO—$NR^Q$—, or —$NR^Q$—CO—O—;

Z is —$COOR^2$, —$SO_2$—$OR^3$, —$PO(OR^4)(OR^5)$, halo, azide, —$NR^6R^7$, or —$NR^8$—CO—$R^9$;

$R^2$, $R^3$, $R^4$, $R^5$, $R^8$, and $R^9$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1, 2, 3, 4, 5, 6, 7, 8, 9, 10, 11, or 12;

t1 at each occurrence is independently 1, 2, 3, 4, 5, 6, 7, 8, 9, or 10; and t2 is an integer from 0-5, wherein the compound is not 4-[4-[[8-benzyl-6-(4-hydroxyphenyl)-3-oxo-7H-imidazo[1,2-a]pyrazin-2-yl]methyl]phenoxy]butanoic acid.

In some embodiments, q is 1.

In some embodiments, $R^1$ is phenyl substituted with one substituent -Q-L-Z, and optionally further substituted with 1 or 2 substituents independently selected from halogen, cyano, nitro, haloalkyl, haloalkoxy, hydroxy, hydroxyalkyl, alkoxy, alkoxyalkyl, amino, alkylamino, dialkylamino, acylamino, aminoalkyl, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y})_{t3}$-A-$(CR^{1x}R^{1y}$—$CR^{1x}R^{1y}$—$O)_{t1}$—$(CR^{1x}R^{1y})_{t2}$—, or —$(CR^{1x}R^{1y})_{t3}$-A-$(CR^{1x}R^{1y})_{t4}$—;

each A is independently —$NR^Q$—CO—;

$R^{1a}$, $R^{1b}$, $R^Q$, $R^{1x}$, and $R^{1y}$ at each occurrence are hydrogen;

m is 6, 7, or 8;

t1 is 6, 7, or 8;

t2 is 1, 2, or 3;

t3 is 6, 7, or 8;

t4 is 1, 2, or 3;

Z is —$SO_2$—$OR^3$, azide, —$NR^6R^7$, —$NR^8$—CO—$R^9$, —CO—$R^{10}$, or —$NR^{11}$—CO—O—$R^{12}$;

$R^3$, $R^6$, $R^7$, $R^8$, $R^9$, $R^{10}$, $R^{11}$, and $R^{12}$ are independently hydrogen, optionally substituted aryl, optionally substituted cycloalkyl, optionally substituted cycloalkenyl, optionally substituted heteroaryl, or optionally substituted heterocycle.

In some embodiments, $R^1$ is phenyl substituted with one substituent -Q-L-Z, and optionally further substituted with 1 or 2 substituents independently selected from halogen, cyano, nitro, haloalkyl, haloalkoxy, hydroxy, hydroxyalkyl, alkoxy, alkoxyalkyl, amino, alkylamino, dialkylamino, acylamino, aminoalkyl, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—;

Z is —$SO_2$—$OR^3$, azide, —$NR^6R^7$, or —$NR^8$—CO—$R^9$;

$R^3$, $R^6$, $R^7$ and $R^8$ are independently hydrogen, optionally substituted $C_1$-$C_8$ alkyl, optionally substituted aryl, optionally substituted cycloalkyl, optionally substituted heteroaryl, or optionally substituted heterocycle; and $R^9$ is optionally substituted heteroalkyl or an energy acceptor.

In some embodiments, $R^1$ is phenyl substituted with one substituent -Q-L-Z and is optionally further substituted with one halogen.

In some embodiments, Q is O.

In some embodiments, L is —$(CR^{1a}R^{1b})_m$—. In some embodiments, at each occurrence, $R^{1a}$ and $R^{1b}$ are hydrogen. In some embodiments, m is 6. In some embodiments, m is 8.

In some embodiments, L is —$(CR^{1x}R^{1y})_{t3}$-A-$(CR^{1x}R^{1y}$—$CR^{1x}R^{1y}$—$O)_{t1}$—$(CR^{1x}R^{1y})_{t2}$—. In some embodiments, at each occurrence, $R^{1x}$ and $R^{1y}$ are hydrogen. In some embodiments, A is —$NR^Q$—CO—, and $R^Q$ is H. In some embodiments, t1 is 2, t2 is 2, and t3 is 8.

In some embodiments, L is —$(CR^{1x}R^{1y})_{t3}$-A-$(CR^{1x}R^{1y})_{t4}$—. In some embodiments, at each occurrence, $R^{1x}$ and $R^{1y}$ are hydrogen. In some embodiments, A is —$NR^Q$—CO—, and $R^Q$ is H. In some embodiments, t3 is 8 and t4 is 2.

In some embodiments, the compound is a compound of formula (Ia)

(Ia)

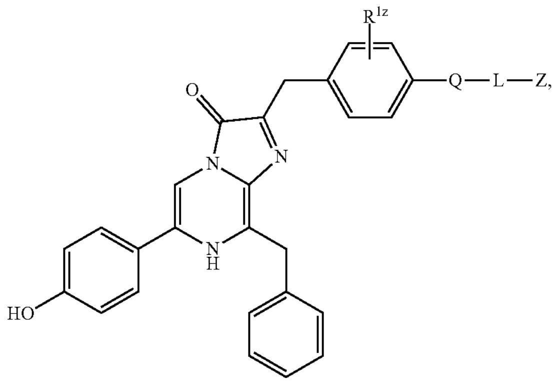

wherein $R^{1z}$ is halogen.

In some embodiments, Q is O; L is —$(CR^{1a}R^{1b})_m$—; $R^{1a}$ and $R^{1b}$ are hydrogen; m is 5, 6, 7, 8, 9 or 10; Z is —$NR^8$—CO—$R^9$; $R^8$ is hydrogen; and $R^9$ is an energy acceptor.

In some embodiments, the energy acceptor is a fluorescent dye selected from a fluorescein, a rhodamine, a coumarin, a pyrene, a cyanine, a squaraine, and a boron-dipyrromethene.

In some embodiments, the group -Q-L-Z has a structure selected from:
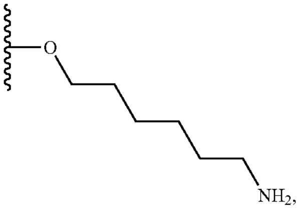
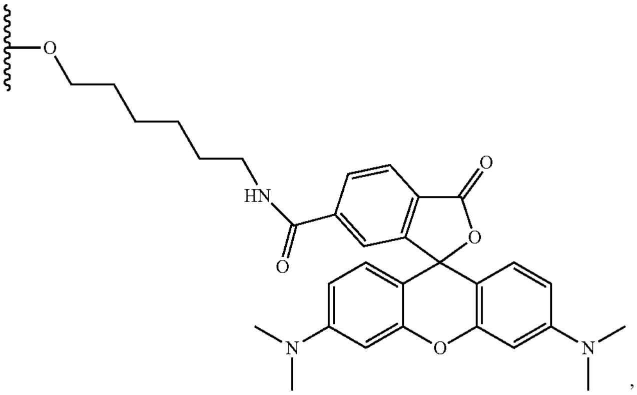
,
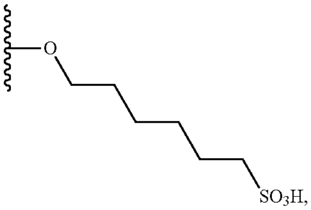
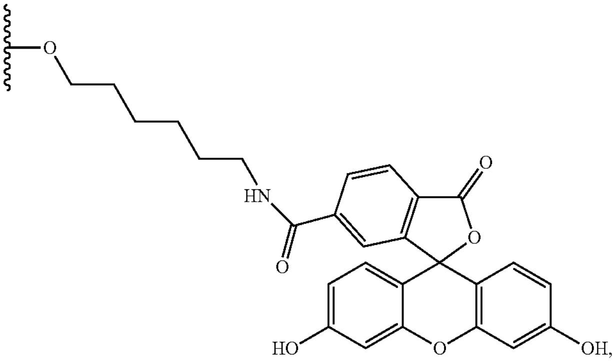
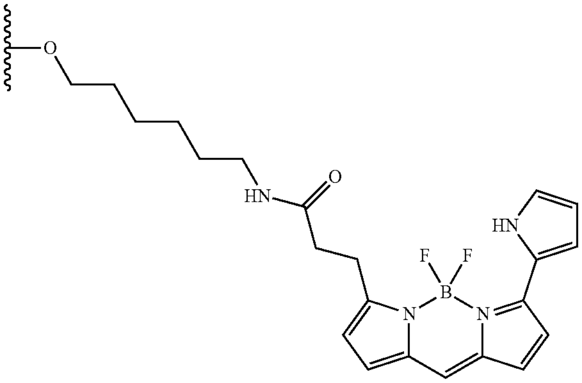
,
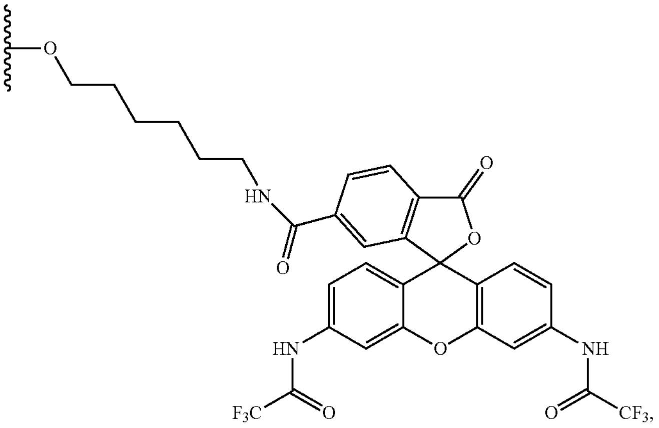

-continued
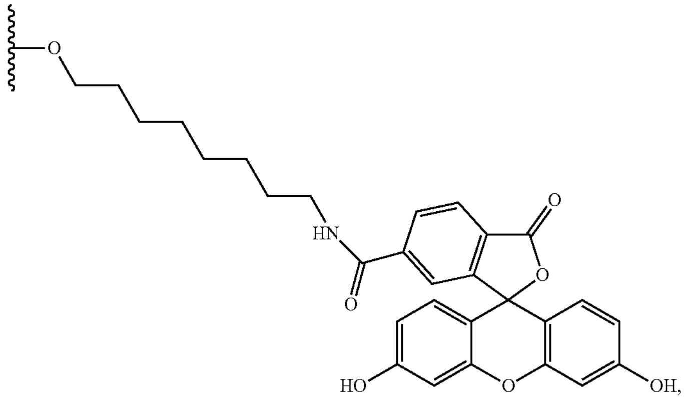
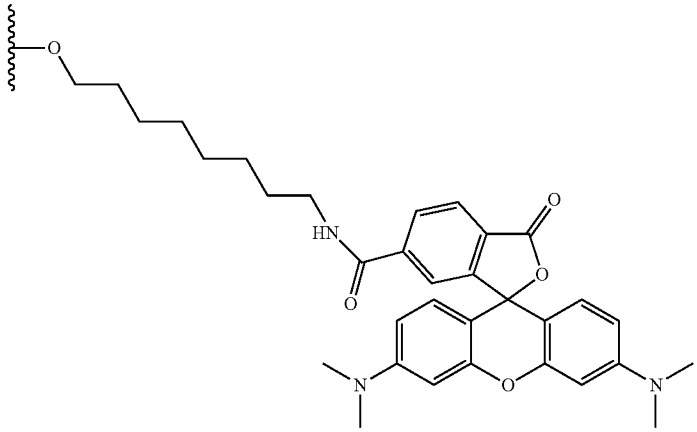
,
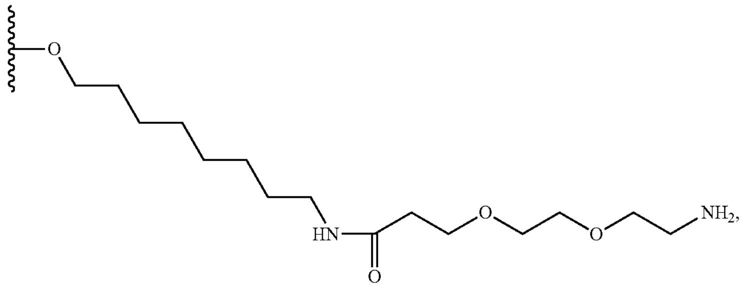
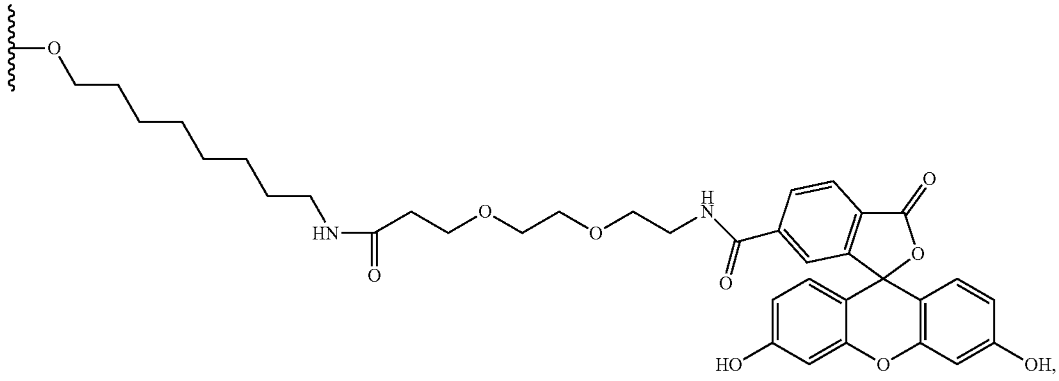

-continued
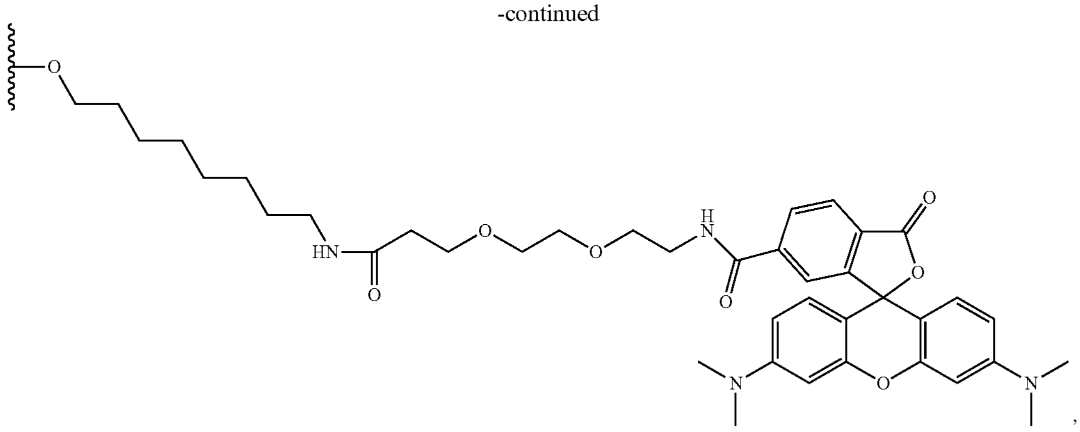
,
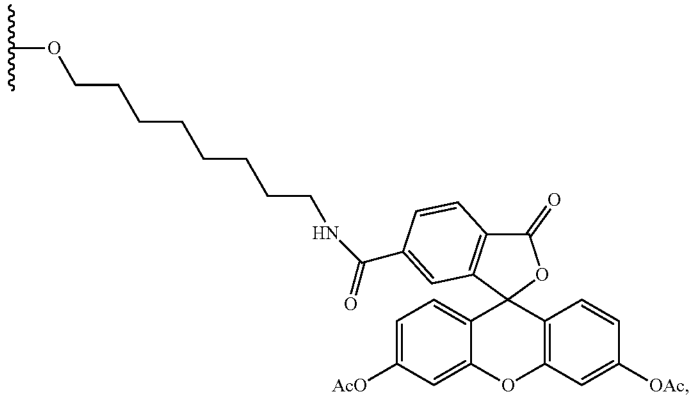
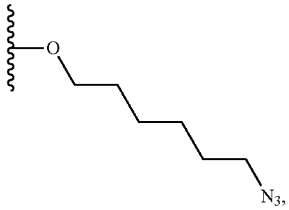
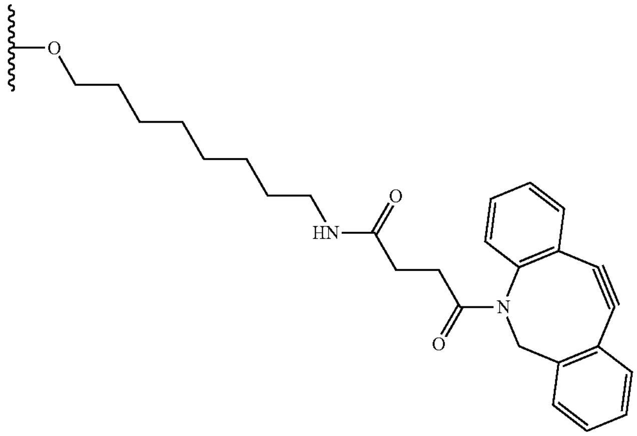
, and
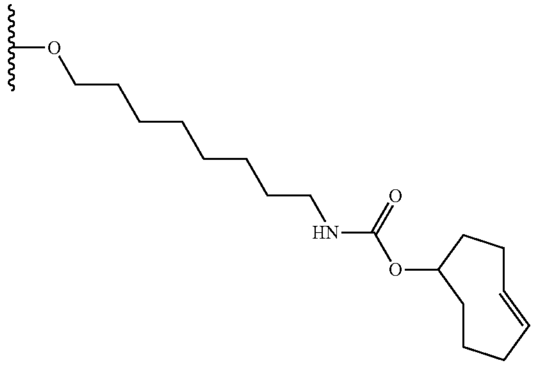
.

In some embodiments, the compound is selected from the group consisting of:

2-(4-((6-aminohexyl)oxy)-3-fluorobenzyl)-8-benzyl-6-(4-hydroxyphenyl)imidazo[1,2-a]pyrazin-3(7H)-one;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-bis(dimethylamino)-3-oxo-3H-spiro[isobenzofuran-1,9'-xanthene]-6-carboxamide;

6-(4-((8-benzyl-6-(4-hydroxyphenyl)-3-oxo-3,7-dihydroimidazo[1,2-a]pyrazin-2-yl)methyl)-2-fluorophenoxy)hexane-1-sulfonic acid;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-dihydroxy-3-oxo-3H-spiro[isobenzofuran-1,9'-xanthene]-6-carboxamide;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3-(5,5-difluoro-7-(1H-pyrrol-2-yl)-5H-514,614-dipyrrolo[1,2-c:2',1'-f][1,3,2]diazaborinin-3-yl)propanamide;

N,N'-(6-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-3-oxo-3H-spiro[isobenzofuran-1,9'-xanthene]-3',6'-diyl)bis(2,2,2-trifluoroacetamide);

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-dihydroxy-3-oxo-3H-spiro[isobenzofuran-1,9'-xanthene]-6-carboxamide;

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-bis(dimethylamino)-3-oxo-3H-spiro[isobenzofuran-1,9'-xanthene]-6-carboxamide;

3-(2-(2-aminoethoxy)ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-dihydroxy-3-oxo-3H-spiro[isobenzofuran-1,9'-xanthene]-6-carboxamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-bis(dimethylamino)-3-oxo-3H-spiro[isobenzofuran-1,9'-xanthene]-6-carboxamide;

6-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-3-oxo-3H-spiro[isobenzofuran-1,9'-xanthene]-3',6'-diyl diacetate;

2-(4-((6-azidohexyl)oxy)-3-fluorobenzyl)-8-benzyl-6-(4-hydroxyphenyl)imidazo[1,2-a]pyrazin-3(7H)-one;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(2,7-difluoro-3,6-dihydroxyxanthylium-9-yl)benzoate;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,11-dihydroxydibenzo[c,h]xanthen-14-ium-7-yl)benzoate;

N1-(8-(4-((8-benzyl-6-(4-hydroxyphenyl)-3-oxo-3,7-dihydroimidazo[1,2-a]pyrazin-2-yl)methyl)-2-fluorophenoxy)octyl)-N4-(2-(5,5-difluoro-1,3-dimethyl-5H-5$\lambda^4$,6$\lambda^4$-dipyrrolo[1,2-c:2',1'-f][1,3,2]diazaborinin-10-yl)ethyl)succinamide;

$N^1$-(8-(4-((8-benzyl-6-(4-hydroxyphenyl)-3-oxo-3,7-dihydroimidazo[1,2-a]pyrazin-2-yl)methyl)-2-fluorophenoxy)octyl)-$N^4$-(dibenzylcyclooctenyl)-succinamide; and (E)-cyclooct-4-en-1-yl (8-(4-((8-benzyl-6-(4-hydroxyphenyl)-3-oxo-3,7-dihydroimidazo[1,2-a]pyrazin-2-yl)methyl)-2-fluorophenoxy)octyl)carbamate.

Structures of these compounds are shown in the Examples. Compound names can be assigned by using Struct=Name naming algorithm as part of CHEMDRAW® ULTRA v. 12.0.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry," $5^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms, as well as geometric isomers, and that these also constitute an aspect of the invention.

Those skilled in the art will appreciate that in compounds in which $R^9$ is an energy acceptor that is a fluorescent dye such as fluorescein, reagents to install the fluorescent dye may be commercially available as mixtures of isomers. For example, carboxyfluorescein succinimidyl ester is commercially available as the 5-isomer, the 6-isomer, and as a mixture of isomers. In some embodiments herein, compounds are illustrated as the 5-isomer or the 6-isomer respectively. However, the disclosure is intended to cover additional isomers and mixtures thereof, depending on the particular starting material that is used.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds of Formula (I)

The compounds of formula (I) may be substrates of luciferases to produce luminescence. "Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multi-well plate such as a 96-well plate) containing the luminescent protein. In still other embodiments, the compounds (e.g., compounds of formula (I)) are introduced into a host and measurements of luminescence are made on the host or a portion thereof, which can include a whole organism or cells, tissues, explants, or extracts thereof. In certain embodiments, the measurement of luminescence is made on the surface of host, such as on the cell surface. In still other embodiments, the compounds (e.g., compounds of formula (I)) are introduced into a host and measurements of luminescence are made in the extracellular space. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) can have an RLU of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100 relative to coelenterazine or a known coelenterazine analogue such as furimazine.

"Cell permeability," "cell membrane permeability," or "membrane permeability," as used interchangeably herein, refers to the ability of the compound to penetrate the cell membrane. This may refer to the ability of the compound to partially embed within the cell membrane. This may refer to the ability of the compound to completely pass through the cell membrane to reach the intracellular space. The coelenterazine analogues disclosed herein may display decreased cell permeability.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the coelenterazine analogues (e.g., compounds of formula (I)), may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® assay technology), or another method known in the art. The effect of the compounds of formula (I) on cell viability or apoptosis may be compared to the effect of native or known coelenterazine analogues on cell viability or apoptosis.

Enhanced biocompatibility may also be determined by measuring the effect of the coelenterazine analogues (e.g., compounds of formula (I)) on cell growth or gene expression. For example, enhanced biocompatibility of the compounds of formula (I) may be determined by measuring the cell number after a period of time or by determining the expression of stress response genes in a sample of cells that are exposed to compounds of formula (I) compared to cells exposed to a native or known coelenterazine or no coelenterazine. The effect of the compounds of formula (I) on cell growth or gene expression may be compared to a native or known coelenterazine.

B. Synthesis of Compounds of Formula (I)

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^1$ and q have the meanings as set forth in the Summary section unless otherwise noted, can be synthesized as shown in Schemes 1-3 and General Procedures A-G. Suitable synthesis methods may also include, for example, those disclosed in U.S. patent application Ser. No. 15/431,961 to Shakhmin et al. entitled "COELENTERAZINE ANALOGUES," filed Feb. 14, 2017), which is incorporated by reference herein in its entirety.

Abbreviations which have been used in the descriptions of the Schemes that follow are: TBDMS, tert-butyldimethylsilyl; TMG, tetramethylguanidine; MeOH, methanol; DCM, dichloromethane; TFA, trifluoroacetic acid.

Scheme 1. Synthesis of compounds with a para-hydroxy 6-position phenyl group
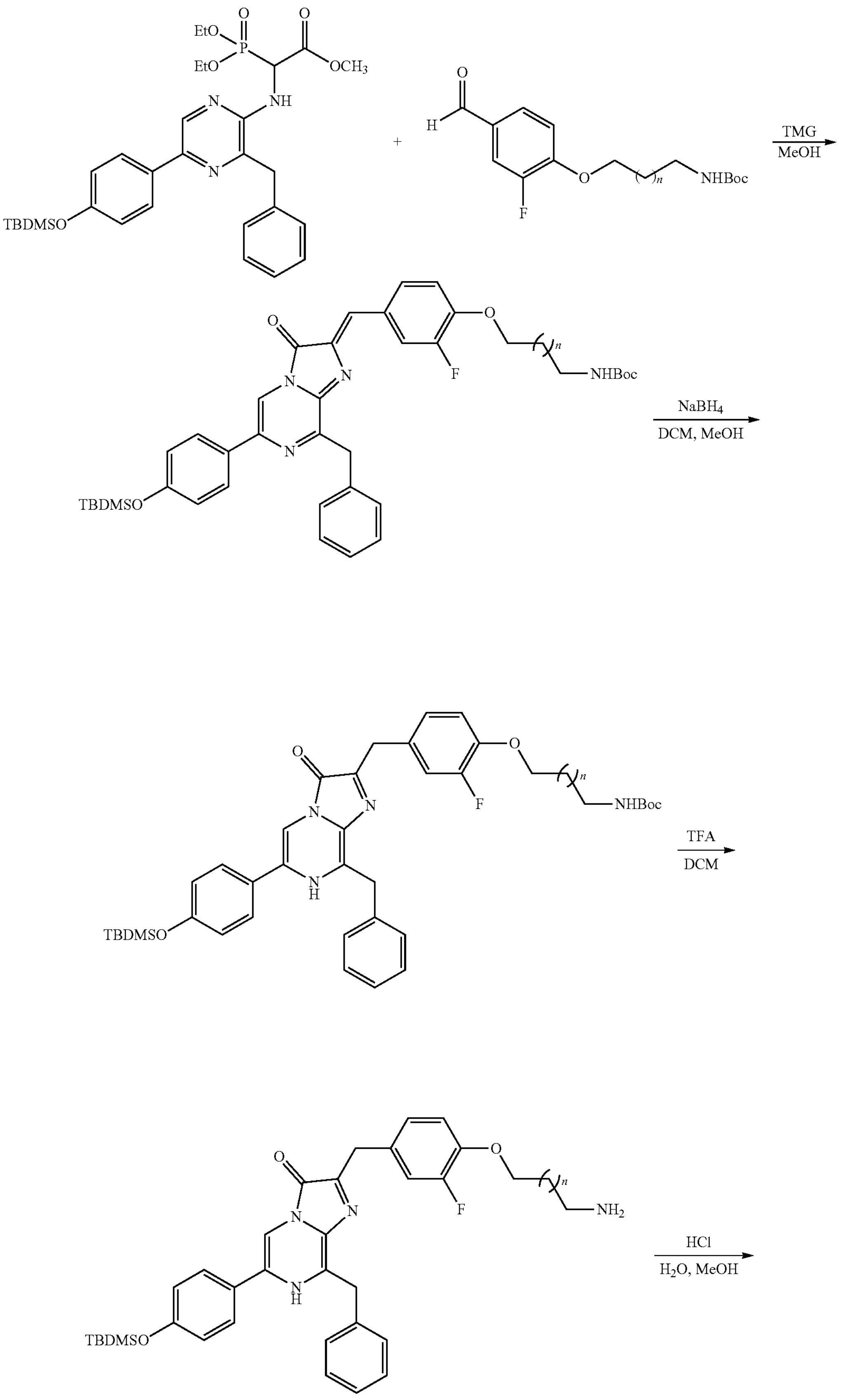

-continued

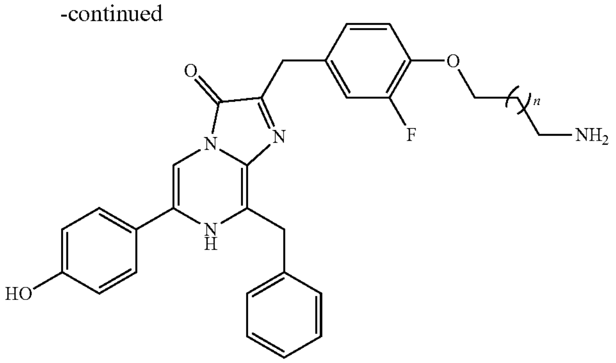

Scheme 2. Synthesis of sulfonate-containing compounds

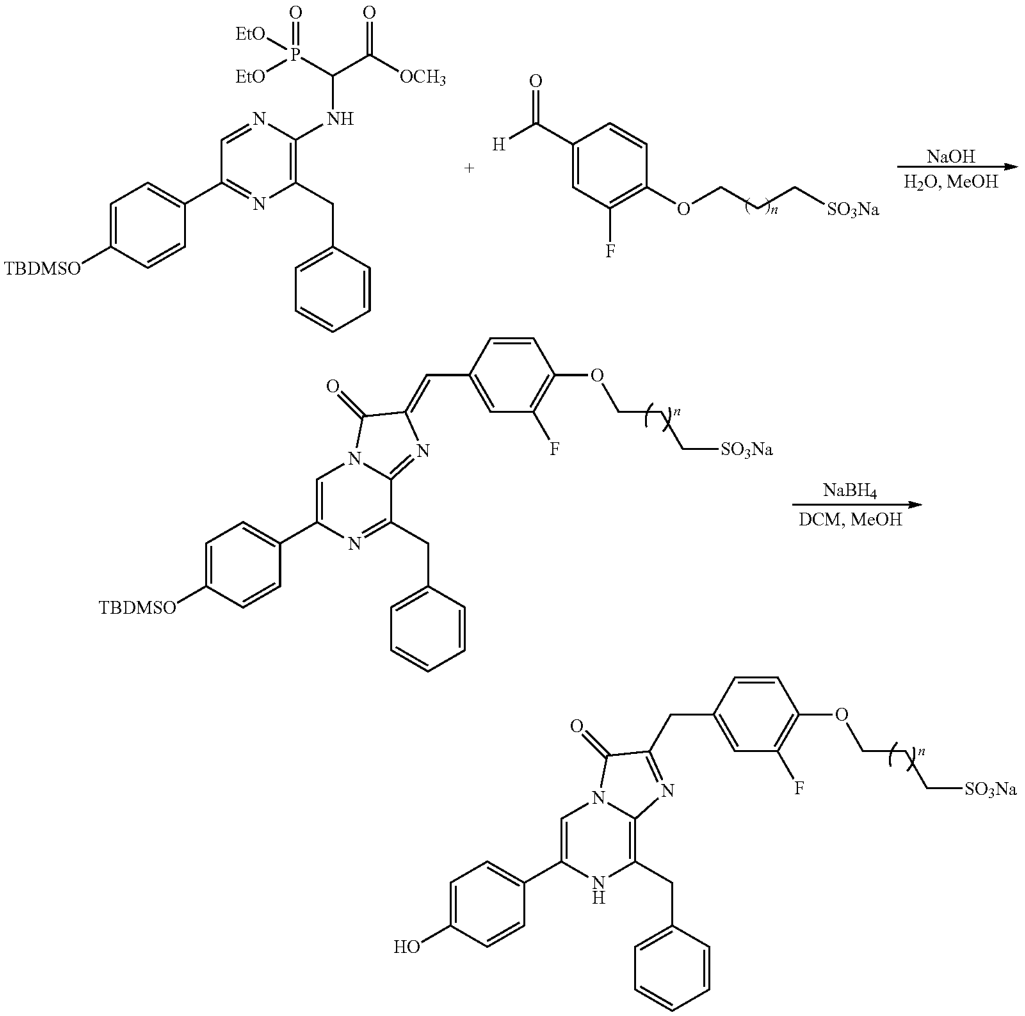

General Procedure A (HWE reaction): To a solution of the aldehyde (1 eq) and methyl 2-((3-benzyl-5-phenylpyrazin-2-yl)amino)-2-(diethoxyphosphoryl)acetate (1 eq) in methanol, 1,1,3,3-tetramethylguanidine (3 eq) was added. The solution was stirred at RT for 0.5-2 h. The mixture was diluted with dichloromethane and ~0.1 M HCl, and the aqueous layer was extracted with dichloromethane. The organic layers were combined, dried with sodium sulfate, filtered, concentrated, and purified with silica gel chromatography.

General Procedure B (reduction): A suspension of the dehydro-coelenterazine (1 eq) in dichloromethane and methanol (1:1) was chilled with an ice bath. Sodium borohydride (5 eq) was added, and the mixture stirred for 0.5-2 h. The mixture was diluted with dichloromethane and ~0.1

M HCl, and the aqueous layer was extracted with dichloromethane. The organic layers were combined, dried with sodium sulfate, filtered, concentrated, and purified with silica gel chromatography.

General Procedure C (TBDMS deprotection): To a solution of the coelenterazine analogue in methanol (10 mL), HCl (6M, 1 mL) was added. The solution was stirred for 2-6 h. The mixture was diluted with DCM and water, and the aqueous layer was extracted with dichloromethane. The organic layers were combined, dried with sodium sulfate, filtered, concentrated, and purified with silica gel chromatography.

General Procedure D (TFA deprotection): To a solution of the coelenterazine analogue in dichloromethane (10 mL), trifluoroacetic acid (1 mL) was added. The solution was stirred for 2-6 h. The mixture was diluted with toluene, concentrated, resuspended in toluene, and concentrated. This was repeated two times. The crude product was purified with silica gel chromatography.

General Procedure E (HWE reaction with sulfonates): To a solution of the sulfonated aldehyde (1 eq) and methyl 2-((3-benzyl-5-phenylpyrazin-2-yl)amino)-2-(diethoxyphosphoryl)acetate (1 eq) in methanol, sodium hydroxide (2 M, 3 eq) was added. The solution was stirred at RT for 0.5-2 h. The mixture was diluted with ethanol, added to Celite, concentrated, and purified with silica gel chromatography.

General Procedure F (reduction with sulfonates): A suspension of the dehydro-coelenterazine (1 eq) in dichloromethane and methanol (1:1) was chilled with an ice bath. Sodium borohydride (5 eq) was added, and the mixture stirred for 0.5-2 h. The mixture was diluted with ethanol, added to Celite, concentrated, and purified with silica gel chromatography.

General Procedure G (reaction of succinimide ester): To a solution of the amino-coelenterazine (1 eq) in dichloromethane and methanol (10:1) was added lutidene (5 eq) and succinimide ester (1 eq). The mixture stirred for 2-18 h. The mixture was diluted with methanol, added to Celite, concentrated, and purified with silica gel chromatography.

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purifying according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups, and the methods for protecting and deprotecting different substituents using such suitable protecting groups, are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. *OPLOPHORUS* LUCIFERASES

The disclosed compounds may be substrates of *Oplophorus*-derived luciferases. The disclosed compounds may be used to label/detect *Oplophorus*-derived luciferases. The disclosed compounds may be used to inhibit *Oplophorus*-derived luciferases. The disclosed compounds may inhibit the luciferase activity of the *Oplophorus*-derived luciferases. The *Oplophorus*-derived luciferase may be a wild-type *Oplophorus* luciferase or a variant of an *Oplophorus* luciferase, such as a luciferase of SEQ ID NO:2. *Oplophorus* luciferase variants are described in U.S. Pat. Nos. 8,557,970 and 8,669,103, each of which is incorporated herein by reference in its entirety.

The polypeptide sequence of the mature 19 kDa subunit of the naturally-occurring form of the *Oplophorus gracilirostris* luciferase is provided in SEQ ID NO: 1. An exemplary polypeptide sequence for a synthetic *Oplophorus*-derived luciferase, which can be used in the methods described herein, is provided in SEQ ID NO: 2 (also interchangeably referred to herein as "NanoLuc," "Nluc," "Nluc luciferase," and "Nluc enzyme").

4. COELENTERAZINE SUBSTRATES

The disclosed compounds may be substrates of *Oplophorus*-derived luciferases. The disclosed compounds of the present invention may be used to label/detect *Oplophorus*-derived luciferases. The disclosed compounds may be used to inhibit luciferase activity. The disclosed compounds may inhibit luciferase activity by competing or interfering with a coelenterazine or coelenterazine-derivative substrate from binding to a luciferase. Coelenterazine substrates are a class of reporter molecules that luminesce when acted upon by luciferases and other bioluminescent proteins. Examples of coelenterazine substrates include but are not limited to: coelenterazine; coelenterazine derivatives and/or analogs such as 2-furanylmethyl-deoxy-coelenterazine (furimazine), coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl-coelenterazine, in addition to those disclosed in WO 2003/040100, U.S. Patent Publication No. 2008/0248511, and U.S. Patent Publication No. US 2012/0117667; pro-coelenterazines (i.e. compounds that are not substrates for a non-luminescent enzyme, which converts the compound to a substrate for a luciferase), quinone-masked coelenterazines, and the like. Further examples of coelenterazine substrates are described in, for example, U.S. Publication No. 2012/0107849, U.S. Publication No. 2013/0130289, U.S. patent application Ser. No. 14/608,910, and U.S. patent application Ser. No. 14/609,372, each of which is incorporated herein by reference.

5. METHODS OF DETECTING, LABELING, AND ISOLATING *OPLOPHORUS* LUCIFERASES

The compounds of the disclosure may be used in any way that luciferase substrates, e.g., coelenterazine analogues, have been used. For example, they may be used in a bioluminogenic method that employs an analogue of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) may be used to quantify small molecules. In some embodiments, a coelenterazine (e.g., a native or known coelenterazine or a compound of formula (I)) can be used as a probe of a specific biochemical activity, e.g., apoptosis or drug metabolism. In some embodiments, the coelenterazine concentration is coupled to a specific enzyme activity by a "pro-coelenterazine" or "pro-substrate" that can be acted on by the specific enzyme of interest. In some embodiments, the pro-coelenterazine is a molecule that cannot support luminescence directly when combined with a luciferase, but can be converted into coelenterazine through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. For example, coelenterazine (e.g., a native or known coelenterazine, or a compound of formula (I)) can be modified to contain a cleavable group, such as 6'-O-methyl. In some embodiments, when incubated with a specific cytochrome P450 enzyme, the 6'O-methyl is cleaved, and the pro-coelenterazine converted to coelenterazine, which can be detected with a luciferase. In some embodiments, the pro-coelenterazine can be combined with other components necessary to support luminescence, e.g., luminescent protein such as a luciferase, to provide a single reagent and a homogeneous assay. For example, when the reagent is added to a sample, luminescence is generated as pro-coelenterazine is converted to coelenterazine. In various embodiments, similar assays can be developed for other enzymes, small molecules, or other cellular processes that can be linked to the generation of coelenterazines from pro-coelenterazines.

In certain embodiments, the compounds of formula (I) can be used for detecting luminescence in live cells. In some embodiments, a luciferase can be expressed in cells (as a reporter or otherwise), and the cells treated with a coelenterazine (e.g., a compound of formula (I)), which will permeate cells in culture, react with the luciferase and generate luminescence. In addition to being cell permeant, the compounds of formula (I) show comparable biocompatibility to native coelenterazine in terms of cell viability. In some embodiments, the compounds of formula (I) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) may be assayed using various microscopy and imaging techniques. In still other embodiments, a secretable luciferase is expressed in cells as part of a live-cell reporter system.

The disclosed compounds may be used in assays that are used detect the presence or activity of enzymes using *Oplophorus* luciferases. For example, they may be used in a bioluminogenic method which employs an *Oplophorus* luciferase and a coelenterazine or coelenterazine-derivative substrate to detect one or more molecules in a sample, e.g., a protein of interest (e.g., an enzyme, a binding partner, a ligand, etc.), a cofactor for an enzymatic reaction, an enzyme substrate, an enzyme inhibitor, an enzyme activator, or OH radicals, or one or more conditions, e.g., redox conditions.

The disclosed compounds may be used in methods to label *Oplophorus* luciferase by forming a covalent bond in the active site. The method may include contacting a compound disclosed herein with a cell expressing or containing an *Oplophorus*-derived luciferase. The method may include contacting a compound disclosed herein with a cell expressing or containing an *Oplophorus*-derived luciferase, wherein the disclosed compounds may selectively react with and disable the *Oplophorus*-derived luciferase. The method may include contacting the sample with a compound disclosed herein, wherein the compound disclosed herein causes luminescence from the *Oplophorus*-derived luciferase with a fast decay rate.

The method may include contacting a compound disclosed herein with a binding partner in an *Oplophorus*-derived luciferase fusion protein, wherein the disclosed compound labels the *Oplophorus*-derived luciferase when the fusion protein is intact. The disclosed compounds may be used in assays that are used detect the presence or activity of enzymes using *Oplophorus* luciferases, to selectively inhibit the signal from the *Oplophorus* luciferase by selectively reacting with the luciferase.

The disclosed compounds may be appended to a variety of functional groups. The disclosed compounds may contain functional groups extending out of the enzyme pocket and into solvent without impacting inhibition potency. For example, the group -Q-L-Z may include an energy acceptor such as a fluorescent or fluorogenic dye moiety, which may be used as a fluorescent tag for NanoLuc-based cell sorting and labeling applications.

In some embodiments, the disclosed compounds may be used to label proteins or surfaces. For example, a compound of Formula (I) may interact with a target protein (such as an enzyme or a receptor) through a reactive or functional group (such as halogen or an inhibitor), which is attached to the compound by an appropriate linker. In some embodiments, the disclosed compounds may be used to capture NLuc fusion proteins, or create a surface, resin, or biomolecule that may quench NLuc bioluminescence.

(1) Cell Uptake, Sorting, and Labeling

In some embodiments, the disclosed compounds may be appended to various biomolecules and macromolecules such as drugs, nucleotides, sugars, proteins, polymers, solid surfaces, chromophores, dyes, etc. for uses in live cell imaging, cell uptake, or cell sorting and labeling. For example, the disclosed compounds may be appended to various functional groups to enable post-labeling of Nluc or NanoBit with desired functional groups.

The disclosed compounds may be appended to a chromophore or a dye, such as a fluorescent dye or a fluorogenic dye. For example, the disclosed compounds may be appended to a fluorescent dye to for use in fluorescent labeling of Nluc or NanoBiT. For example, the disclosed compounds may be appended to a fluorescent dye for use in fluorescence activated cell sorting (FACS). Cells may be transfected with a Nluc fusion protein, such as a Nluc-HT fusion protein, and exposed to disclosed compound appended to the fluorescent dye. A cell permeable compound-dye conjugate will label Nluc in cells expressing the Nluc fusion protein, generating fluorescence. After appropriate incubation and wash steps, the fluorescent cells can be sorted by FACS and used for future biochemical experiments. As another example, the disclosed compounds may be appended to a fluorescent dye or a chromophore for use in live cell imaging, thus enabling bioluminescence imaging of intracellular, extracellular, and cell surface events.

The disclosed compounds may be appended to various functional groups for chemical or bio-orthogonal reactions. For example, the disclosed compounds may be appended to various functional groups and used in click chemistry, cyanobenzthiazole chemistry, triazene chemistry, and the like. For example, the disclosed compounds may be used in a two-step method to fluorescently label NanoLuc. In such embodiments, the disclosed compounds may be appended to a reactive functional group, and a fluorescent dye with a complementary reactive group could be added to fluorescently label NanoLuc. Cells may be transfected with a Nluc fusion protein and exposed to the disclosed compound appended to an azide. A fluorescent dye conjugate could be added, and the Nluc fusion protein bound to the azide-appended compound will be fluorescently labeled.

(2) Protein Isolation

In some embodiments, the disclosed compounds may be used to capture or isolate *Oplophorus* luciferase fusion proteins. In some embodiments, the disclosed compounds may be used to isolate *Oplophorus* luciferase fusion proteins using NanoLuc®- and HALOTAG®-based technologies. In some embodiments, the disclosed compounds may be used to isolate *Oplophorus* luciferase fusion proteins using click chemistry. For example, the disclosed compounds may be used to isolate *Oplophorus* luciferase fusion proteins using NanoLuc®- and azide or alkyne-modified beads or surfaces. In other embodiments, the disclosed compounds may be used to isolate *Oplophorus* luciferase fusion proteins using NanoLuc®- and streptavidin-modified beads or surfaces. In some embodiments, the disclosed compounds may be used to isolate *Oplophorus* luciferase fusion proteins using NanoLuc®- and cyanobenzothiazole-modified beads or surfaces. In some embodiments, the disclosed compounds may be appended to various biomolecules and macromolecules such as drugs, nucleotides, sugars, proteins, polymers, and solid surfaces for use in *Oplophorus* luciferase fusion protein isolation. For example, cells may be transfected with a Nluc fusion protein, such as a Nluc-HT fusion protein, and exposed to disclosed compound appended to a functional group. The functional group may be a molecule that binds to a solid support, thus enabling isolation of the Nluc fusion protein.

6. METHODS OF INHIBITING *OPLOPHORUS* LUCIFERASE ACTIVITY

The disclosed compounds may be used in methods to inhibit *Oplophorus* luciferase. The disclosed compounds may inhibit *Oplophorus* luciferase by forming a covalent bond in the active site. The method may include contacting a compound disclosed herein with a cell expressing or containing an *Oplophorus*-derived luciferase, wherein the disclosed compounds may selectively react with and disable the *Oplophorus*-derived luciferase. The method may include contacting the sample with a coelenterazine substrate and a compound disclosed herein, wherein the compound disclosed herein causes a decrease in the luminescence from the *Oplophorus*-derived luciferase. The method may include contacting the sample with the coelenterazine substrate prior to contacting the sample with the compound disclosed herein. The method may include contacting the sample with the compound disclosed herein prior to contacting the sample with the coelenterazine substrate.

The method may include contacting a compound disclosed herein with a binding partner in an *Oplophorus*-derived luciferase fusion protein, wherein the disclosed compound inhibits the *Oplophorus*-derived luciferase when the fusion protein is intact. The disclosed compounds may serve to inhibit the luciferase to selectively suppress the luminescent signal in embodiments in which such suppression may be desired, such as in applications involving temporal multiplexing of multiple bioluminescent systems, or in some plate-based luminescent assays. For example, the disclosed compounds may be used to inhibit intracellular and/or extracellular *Oplophorus* luciferase activities.

(1) Use of Cell-Impermeable Compounds

In certain embodiments, the methods disclosed herein include contacting a sample (e.g., a cell) with a mixture of a cell-permeable coelenterazine substrate and a compound described herein that is modified such that it is cell-impermeable. In such embodiments, the disclosed compounds and methods may be used to build up the initial brightness of a high-throughput screening operation assay format, and then selectively inhibit any luciferases that may be excreted from cells, to selectively inhibit luminescence that may occur outside of the cells. Such methods may provide for a more selective signal within cells.

(2) Use of Cell-Permeable Compounds

In certain embodiments, the methods disclosed herein include contacting a sample (e.g., a cell) with a mixture of a cell-permeable coelenterazine substrate and a compound described herein that is cell-permeable. In such embodiments, the disclosed compounds can enter in to cells and selectively inhibit an *Oplophorus* luciferase therein. Such methods may be advantageous in multiplexing assays that involve use of two or more luciferases and may allow for inhibition of luminescence from an *Oplophorus* luciferase so as to selectively view luminescence from another luciferase inside the cell.

(3) Multiplexing

The disclosed compounds may be used to inhibit *Oplophorus* luciferases as applied to temporal multiplexing with other luciferases and assays. In some embodiments, the *Oplophorus*-derived luciferase or variant thereof may be multiplexed with another enzyme (e.g. a luciferase) that emits light at a different wavelength, e.g., green firefly luciferase, e.g., *Photinus pyralis* (e.g., Luc2; Promega Corp) or red click beetle luciferase (Chroma-Luc™ luciferase; Promega Corp.). For example, if an *Oplophorus* luciferase is used as a functional reporter, then the green firefly luciferase or red Chroma-Luc™ luciferase could be used to control for non-specific effects on genetic regulation or to normalize for transfection efficiency. In some embodiments, luminescence generated from the *Oplophorus* luciferase (approximately 460 nm) and red Chroma-Luc (approximately 610 nm) can be easily resolved using a luminometer with wavelength-discriminating filters, enabling the measurement of both signals from the same sample. In such embodiments, a compound described herein can be used to selectively inhibit the *Oplophorus* luciferase, such that the signal from the other luciferase can be selectively viewed.

In another example, an *Oplophorus* luciferase could be used as a transcriptional reporter and paired with a luciferase that emits light at a different wavelength contained in an assay reagent. In another example, an *Oplophorus* luciferase may be used with one or more additional luciferases, where the luminescence of each luciferase may be separately measured through the use of selective enzyme inhibitors. For example, the luminescence of the *Oplophorus* luciferase may be measured upon addition of appropriate substrates and buffers, followed by measurement of a second luciferase upon a subsequent addition of appropriate substrates and buffers and one or more compounds described herein, which are selective for the an *Oplophorus* luciferase. In another example, the *Oplophorus* luciferase contained in an assay reagent may be used for measuring a specific aspect of cellular physiology, for example ATP to estimate cell viability or caspase activity to estimate cellular apoptosis.

(4) Suicide Inhibition

In some embodiments, the disclosed compounds may be used as suicide inhibitors which irreversibly inhibit *Oplophorus* luciferase. The disclosed compounds may be suicide substrates of *Oplophorus*-derived luciferase which initially produce a bioluminescent signal upon reaction with the luciferase and subsequently irreversibly inhibit the *Oplophorus*-derived luciferase. The disclosed compounds may inhibit the *Oplophorus*-derived luciferase by forming a covalent adduct with the *Oplophorus*-derived luciferase. The disclosed compounds may inhibit NanoLuc as well as the NanoBiT complementary enzyme system. In some embodiments, the disclosed compounds may be used as suicide substrates applied to a ligand-receptor binding assay.

7. SAMPLE

The disclosed compounds may be used with samples containing biological components. The sample may comprise cells. The sample may comprise heterogeneous mixtures of components (including intact cells, cell extracts, cell lysates, bacteria, viruses, organelles, exosomes, and mixtures thereof) or a single component or homogeneous group of components (e.g., natural or synthetic amino acid, nucleic acid or carbohydrate polymers, or lipid membrane complexes). The disclosed compounds may be generally non-toxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase. The cells may have been genetically modified via recombinant techniques.

8. KITS

Disclosed are kits for determining the presence or activity of one or more enzymes (e.g., an *Oplophorus* or *Oplophorus* variant luciferase). The kit may include one or more of the following: a compound or composition of the invention that may inhibit the *Oplophorus* or *Oplophorus* variant luciferase, a coelenterazine or coelenterazine-derivative substrate, an *Oplophorus* or *Oplophorus* variant luciferase, instructions for carrying out a luminescence assay, and reaction buffer(s). The reaction buffers may be present in individual formulations for the non-luciferase enzyme reactions and the luminescent enzyme reactions or in a single formulation for a single step assay. The kits may also contain other inhibitors, activators, and/or enhancers for the non-luciferase enzyme(s). The kits may also contain a positive and/or negative control for the assay.

9. EXAMPLES

In the following Examples, references to "general procedures" refer to the procedures described following Schemes 1-3 in the Detailed Description section.

Abbreviations used in the Examples include the following: DBCO is dibenzylcyclooctyne; DCM is dichloromethane; DMEM is Dulbecco's Modified Eagle Medium; DMF is N,N-dimethylformamide; DMSO is dimethylsulfoxide; FAM is fluorescein; JOE is carboxy-4',5'-dichloro-2',7'-dimethoxyfluorescein; SE is succinimidyl ester; R110 is rhodamine 110; TCO is trans-cyclooctene; TFA is trifluoroacetic acid.

Example 1

2-(4-((6-aminohexyl)oxy)-3-fluorobenzyl)-8-benzyl-6-(4-hydroxyphenyl)imidazo[1,2-a]pyrazin-3(7H)-one (JRW-0855)

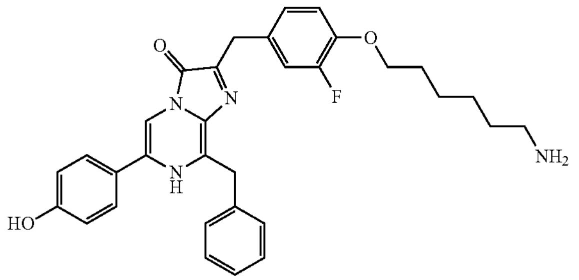 [SMILES: NCCCCCCOc1ccc(Cc2nc3c(Cc4ccccc4)[nH]c(-c4ccc(O)cc4)cn-3c2=O)cc1F]

Step 1. Tert-butyl (Z)-(6-(4-((8-benzyl-6-(4-((tert-butyldimethylsilyl)oxy)phenyl)-3-oxoimidazo[1,2-a]pyrazin-2(3H)-ylidene)methyl)-2-fluorophenoxy)hexyl)carbamate (JRW-0852)

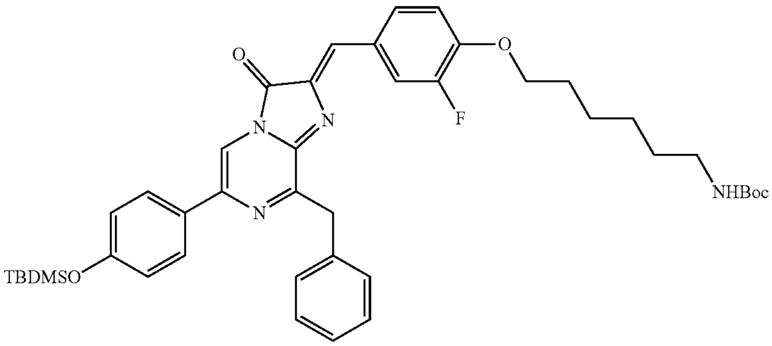 [SMILES: CC(C)(C)OC(=O)NCCCCCCOc1ccc(/C=C2\N=C3C(Cc4ccccc4)=NC(c4ccc(O[Si](C)(C)C(C)(C)C)cc4)=CN3C2=O)cc1F]

Following general procedure A, tert-butyl (6-(2-fluoro-4-formylphenoxy)hexyl)carbamate (271 mg, 0.80 mmol) was reacted with methyl 2-((3-benzyl-5-(4-((tert-butyldimethylsilyl)oxy)phenyl)pyrazin-2-yl)amino)-2-(diethoxyphosphoryl)acetate (400 mg, 0.67 mmol) to afford crude product (490 mg) as a black solid.

Step 2. Tert-butyl (6-(4-((8-benzyl-6-(4-((tert-butyldimethylsilyl)oxy)phenyl)-3-oxo-3,7-dihydroimidazo[1,2-a]pyrazin-2-yl)methyl)-2-fluorophenoxy)hexyl)carbamate (JRW-0853)

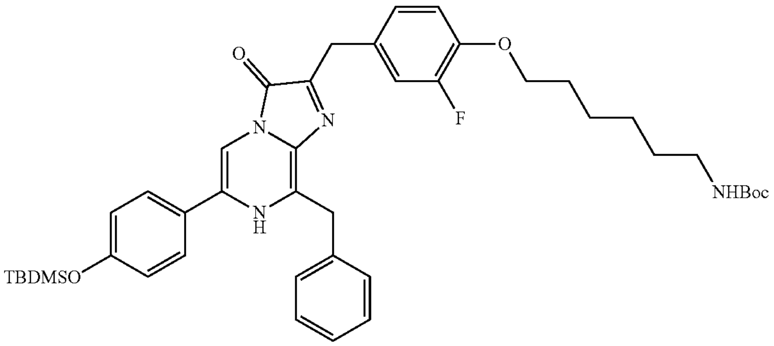 [SMILES: CC(C)(C)OC(=O)NCCCCCCOc1ccc(Cc2nc3c(Cc4ccccc4)[nH]c(-c4ccc(O[Si](C)(C)C(C)(C)C)cc4)cn-3c2=O)cc1F]

Following general procedure B, tert-butyl (Z)-(6-(4-((8-benzyl-6-(4-((tert-butyldimethylsilyl)oxy)phenyl)-3-oxo-imidazo[1,2-a]pyrazin-2(3H)-ylidene)methyl)-2-fluorophenoxy)hexyl)carbamate (490 mg, 0.65 mmol) was reacted with sodium borohydride (123 mg, 3.2 mmol) to afford the crude product (220 mg) as an orange solid.

Step 3. 2-(4-((6-Aminohexyl)oxy)-3-fluorobenzyl)-8-benzyl-6-(4-hydroxyphenyl)imidazo[1,2-a]pyrazin-3(7H)-one (JRW-0855)

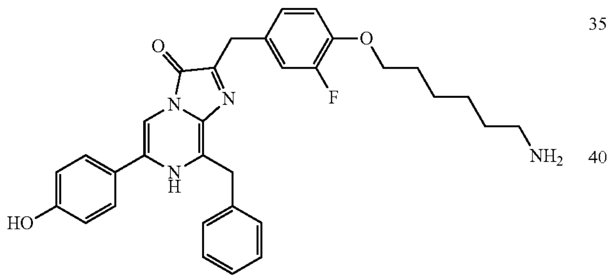

Following general procedure D, tert-butyl (6-(4-((8-benzyl-6-(4-((tert-butyldimethylsilyl)oxy)phenyl)-3-oxo-3,7-dihydroimidazo[1,2-a]pyrazin-2-yl)methyl)-2-fluorophenoxy)hexyl)carbamate (220 mg, 0.29 mmol) was reacted with trifluoroacetic acid (3 mL) to afford the desired product (60 mg, 16% over three steps) as an orange solid. $^1$H NMR (400 MHz, $CD_3OD$) δ 7.67-7.52 (m, 1H), 7.52-7.44 (m, 2H), 7.44-7.38 (m, 2H), 7.36-7.29 (m, 2H), 7.29-7.22 (m, 1H), 7.17-7.04 (m, 2H), 7.00 (t, J=8.5 Hz, 1H), 6.95-6.86 (m, 2H), 4.43 (s, 2H), 4.12 (s, 2H), 4.04 (t, J=6.2 Hz, 2H), 3.01-2.87 (m, 2H), 1.87-1.77 (m, 2H), 1.75-1.64 (m, 2H), 1.61-1.43 (m, 4H); ESI MS m/z 541 $[M+H]^+$; HPLC 84.4% (AUC), $T_R$ 4.42 min; UV (MeOH) λ 264 nm, ε 11,027.

Example 2

4-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-2-(3,6-bis(dimethylamino)xanthylium-9-yl)benzoate (JRW-0857)

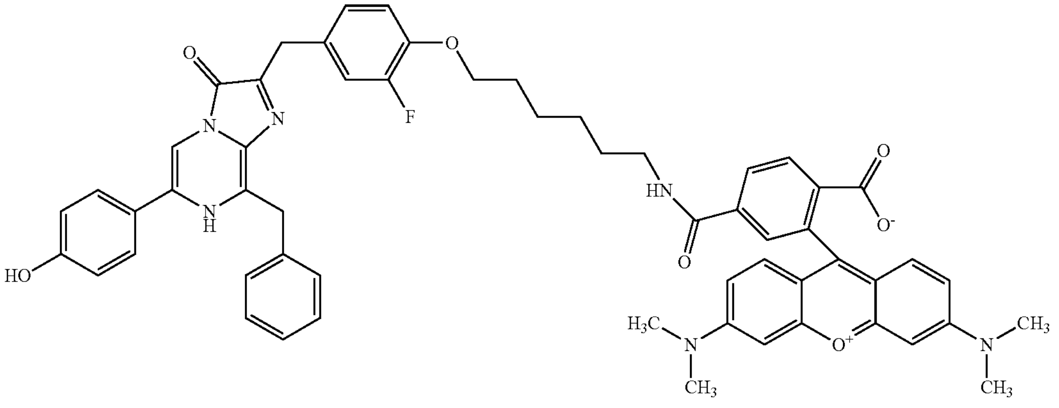 [SMILES: CN(C)c1ccc2c(-c3cc(C(=O)NCCCCCCOc4ccc(Cc5nc6c(Cc7ccccc7)[nH]c(-c7ccc(O)cc7)cn-6c5=O)cc4F)ccc3C(=O)[O-])c3ccc(N(C)C)cc3[o+]c2c1]

Following general procedure G, 2-(4-((6-aminohexyl)oxy)-3-fluorobenzyl)-8-benzyl-6-(4-hydroxyphenyl)imidazo[1,2-a]pyrazin-3(7H)-one (60 mg, 0.11 mmol) was reacted with 2-(3,6-bis(dimethylamino)xanthylium-9-yl)-4-(((2,5-dioxopyrrolidin-1-yl)oxy)carbonyl)benzoate (29 mg, 0.055 mmol) to afford the desired product (9 mg, 8%) as a red solid. Note: compound showed instability in solution. ESI MS m/z 954 $[M+H]^+$; HPLC 60.7% (AUC), $T_R$ 6.58 min; UV (MeOH) λ 542 nm, ε 73,359.

Example 3

Sodium 6-(4-((8-benzyl-6-(4-hydroxyphenyl)-3-oxo-3,7-dihydroimidazo[1,2-a]pyrazin-2-yl)methyl)-2-fluorophenoxy)hexane-1-sulfonate (JRW-0892-2)

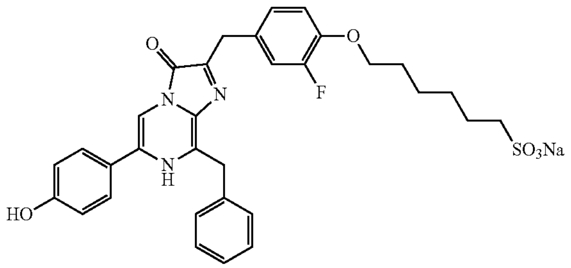

Step 1. Sodium (Z)-6-(4-((8-benzyl-6-(4-((tert-butyldimethylsilyl)oxy)phenyl)-3-oxoimidazo[1,2-a]pyrazin-2(3H)-ylidene)methyl)-2-fluorophenoxy)hexane-1-sulfonate (JRW-0890)

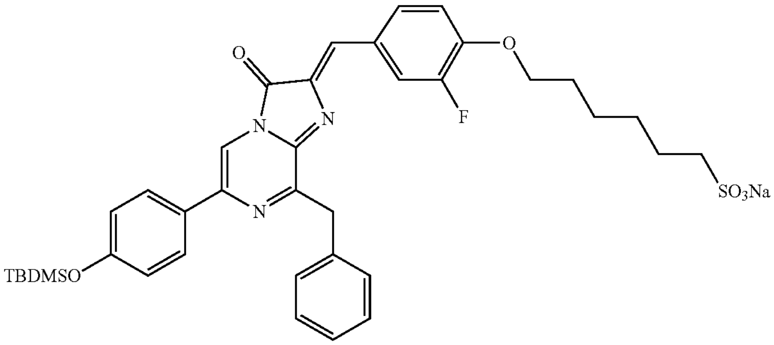

Following general procedure E, sodium 6-(2-fluoro-4-formylphenoxy)hexane-1-sulfonate (108 mg, 0.33 mmol) was reacted with methyl 2-((3-benzyl-5-(4-((tert-butyldimethylsilyl)oxy)phenyl)pyrazin-2-yl)amino)-2-(diethoxyphosphoryl)acetate (200 mg, 0.33 mmol) to afford crude product as a red-black solid.

Step 2. Sodium 6-(4-((8-benzyl-6-(4-hydroxyphenyl)-3-oxo-3,7-dihydroimidazo[1,2-a]pyrazin-2-yl) methyl)-2-fluorophenoxy)hexane-1-sulfonate (JRW-0892-2)

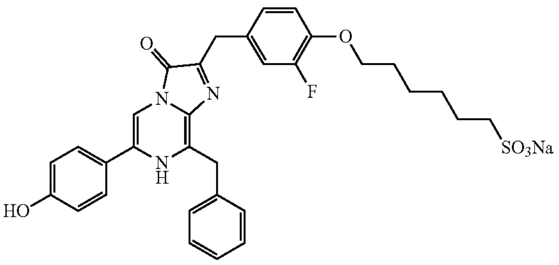

Following general procedure F, sodium (Z)-6-(4-((8-benzyl-6-(4-((tert-butyldimethylsilyl)oxy)phenyl)-3-oxoimidazo[1,2-a]pyrazin-2(3H)-ylidene)methyl)-2-fluorophenoxy)hexane-1-sulfonate (0.33 mmol) was reacted with sodium borohydride (63, mg, 1.7 mmol) to afford the desired product (49 mg, 23% over two steps) as an orange solid. $^1H$ NMR (400 MHz, $CD_3OD$) δ 7.62-7.43 (m, 2H), 7.43-7.38 (m, 2H), 7.36-7.28 (m, 2H), 7.28-7.21 (m, 1H), 7.15-6.96 (m, 3H), 6.94-6.86 (m, 2H), 4.43 (s, 2H), 4.12 (s, 2H), 4.09-3.96 (m, 2H), 2.87-2.79 (m, 2H), 1.93-1.72 (m, 4H), 1.60-1.46 (m, 4H); ESI MS m/z 606 $[M+H-Na]^+$; HPLC 97.6% (AUC), $T_R$ 4.33 min; UV (MeOH) λ 264 nm, ε 25,559.

Example 4

4-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-2-(3,6-dihydroxyxanthylium-9-yl)benzoate (JRW-0893)

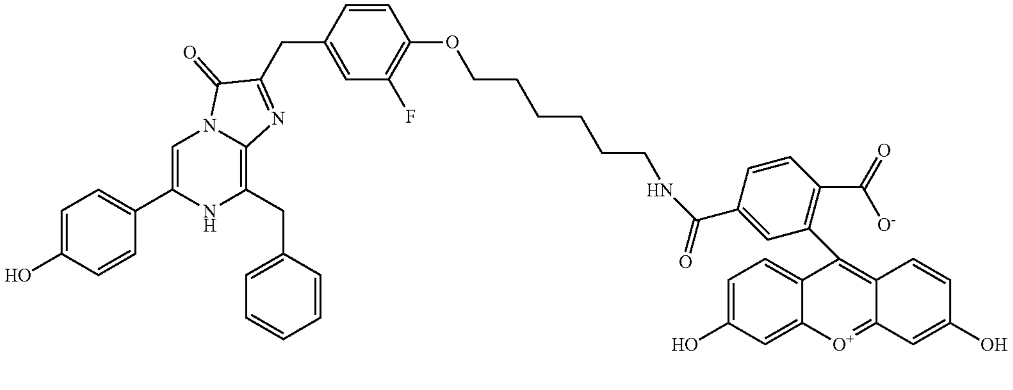 [SMILES: O=C(NCCCCCCOc1ccc(Cc2nc3c(Cc4ccccc4)[nH]c(-c4ccc(O)cc4)cn-3c2=O)cc1F)c1ccc(C(=O)[O-])c(-c2c3ccc(O)cc3[o+]c3cc(O)ccc23)c1]

Following general procedure G, 2-(4-((6-aminohexyl)oxy)-3-fluorobenzyl)-8-benzyl-6-(4-hydroxyphenyl)imidazo[1,2-a]pyrazin-3(7H)-one (53 mg, 0.10 mmol) was reacted with 2-(3,6-dihydroxyxanthylium-9-yl)-4-(((2,5-dioxopyrrolidin-1-yl)oxy)carbonyl)benzoate (55 mg, 0.12 mmol) [Note: the FAM-SE was a mixture of 5- and 6-isomers] to afford the desired product (26 mg, 30%) as an orange solid. $^1$H NMR (400 MHz, $CD_3OD$) δ 8.54-8.42 (m, 2H), 8.35-8.27 (m, 1H), 7.92-7.88 (m, 1H), 7.82-7.76 (m, 2H), 7.60-7.49 (m, 3H), 7.49-7.36 (m, 4H), 7.36-7.15 (m, 5H), 7.13-7.00 (m, 2H), 6.96-6.90 (m, 2H), 4.62 (s, 2H), 4.26 (s, 2H), 4.11-3.96 (m, 2H), 3.42 (t, J=7.0 Hz, 2H), 1.89-1.61 (m, 4H), 1.61-1.41 (m, 4H); ESI MS m/z 899 $[M+H]^+$; HPLC 73.4% (AUC), $T_R$ 5.22 min; UV (MeOH) λ 444 nm, ε 23,843.

Example 5

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3-(5,5-difluoro-7-(1H-pyrrol-2-yl)-5H-514,614-dipyrrolo[1,2-c:2',1'-f][1,3,2]diazaborinin-3-yl)propanamide (JRW-0900)

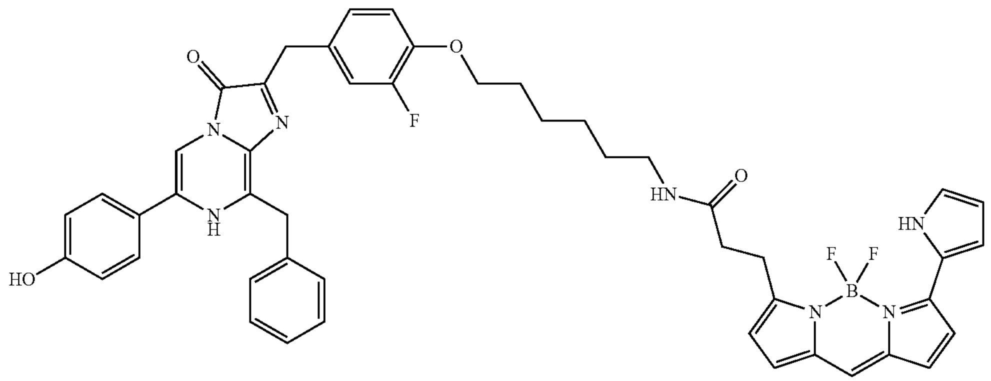

Following general procedure G, 2-(4-((6-aminohexyl)oxy)-3-fluorobenzyl)-8-benzyl-6-(4-hydroxyphenyl)imidazo[1,2-a]pyrazin-3(7H)-one (20 mg, 0.037 mmol) was reacted with 2,5-dioxopyrrolidin-1-yl 3-(5,5-difluoro-7-(1H-pyrrol-2-yl)-5H-514,614-dipyrrolo[1,2-c:2',1'-f][1,3,2]diazaborinin-3-yl)propanoate (15 mg, 0.037 mmol) to afford the desired product (10 mg, 32%) as a black solid. $^1$H NMR (400 MHz, $CD_3OD$) δ 8.37 (s, 1H), 7.73 (d, J=8.7 Hz, 2H), 7.49-7.44 (m, 2H), 7.37-7.29 (m, 2H), 7.29-7.22 (m, 1H), 7.22-6.89 (m, 9H), 6.82 (s, 1H), 6.37-6.26 (m, 1H), 5.53-5.41 (m, 1H), 4.58 (s, 2H), 4.26 (s, 2H), 4.02 (t, J=6.3 Hz, 2H), 3.32-3.27 (m, 2H), 3.24 (t, J=6.9 Hz, 2H), 2.80-2.70 (m, 2H), 1.81-1.67 (m, 2H), 1.56-1.40 (m, 4H), 1.36-1.25 (m, 4H); ESI MS m/z 852 $[M+H]^+$; HPLC 97.1% (AUC), $T_R$ 5.74 min; UV (MeOH) λ 578 nm, ε 72,280.

Example 6

N,N'-(6-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-3-oxo-3H-spiro[isobenzofuran-1,9'-xanthene]-3',6'-diyl)bis(2,2,2-trifluoroacetamide) (JRW-0905)

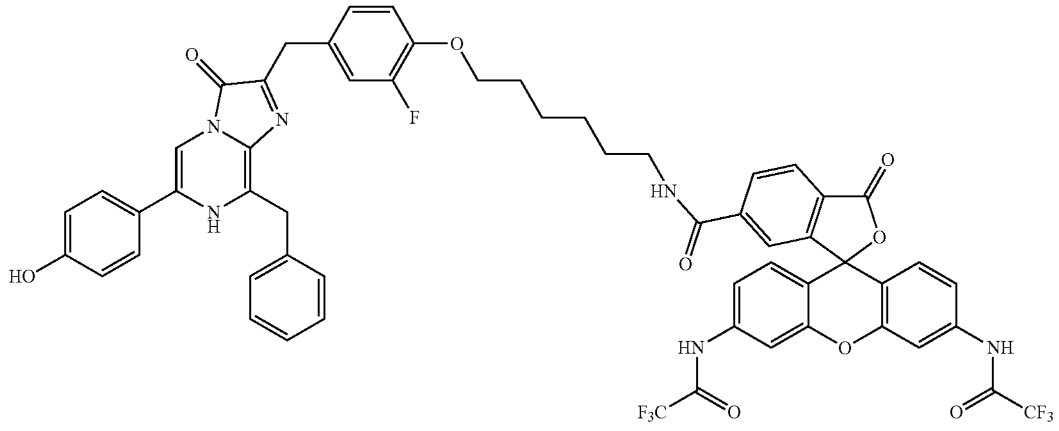 [SMILES: O=C(NCCCCCCOc1ccc(Cc2nc3c(Cc4ccccc4)[nH]c(-c4ccc(O)cc4)cn-3c2=O)cc1F)c1ccc2c(c1)C1(OC2=O)c2ccc(NC(=O)C(F)(F)F)cc2Oc2cc(NC(=O)C(F)(F)F)ccc21]

Following general procedure G, 2-(4-((6-aminohexyl)oxy)-3-fluorobenzyl)-8-benzyl-6-(4-hydroxyphenyl)imidazo[1,2-a]pyrazin-3(7H)-one (50 mg, 0.092 mmol) was reacted with 2,5-dioxopyrrolidin-1-yl 3-oxo-3',6'-bis(2,2,2-trifluoroacetamido)-3H-spiro[isobenzofuran-1,9'-xanthene]-6-carboxylate (67 mg, 0.10 mmol) [Note: the R110-SE was a mixture of 5- and 6-isomers] to afford the desired product (35 mg, 35%) as an orange solid. The 6-isomer is illustrated and named, but the product here is a mixture of the 5- and 6-isomers. $^1$H NMR (400 MHz, $CD_3OD$) δ 8.50-8.44 (m, 1H), 8.23-8.09 (m, 2H), 7.92-7.84 (m, 2H), 7.66-7.55 (m, 2H), 7.52-7.44 (m, 2H), 7.43-7.17 (m, 10H), 7.13-6.82 (m, 10H), 4.44-4.37 (m, 2H), 4.13-4.07 (m, 2H), 4.06-3.93 (m, 2H), 3.46 (t, J=6.9 Hz, 2H), 1.89-1.64 (m, 4H), 1.62-1.45 (m, 4H); ESI MS m/z 1089 $[M+H]^+$; HPLC 61.4% (AUC), $T_R$ 5.97 min; UV (MeOH) λ 434 nm, ε 8,791.

Example 7

2-(4-((8-aminooctyl)oxy)-3-fluorobenzyl)-8-benzyl-6-(4-hydroxyphenyl)imidazo[1,2-a]pyrazin-3(7H)-one (JRW-0904)

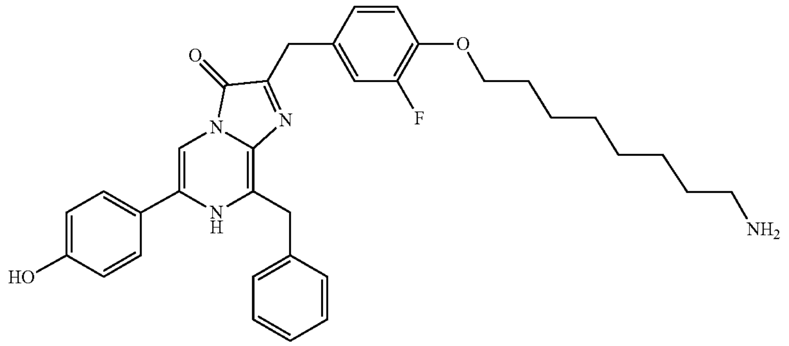 [SMILES: NCCCCCCCCOc1ccc(Cc2nc3c(Cc4ccccc4)[nH]c(-c4ccc(O)cc4)cn-3c2=O)cc1F]

Step 1. tert-butyl (Z)-(8-(4-((8-benzyl-6-(4-((tert-butyldimethylsilyl)oxy)phenyl)-3-oxoimidazo[1,2-a]pyrazin-2(3H)-ylidene)methyl)-2-fluorophenoxy)octyl)carbamate (JRW-0901)

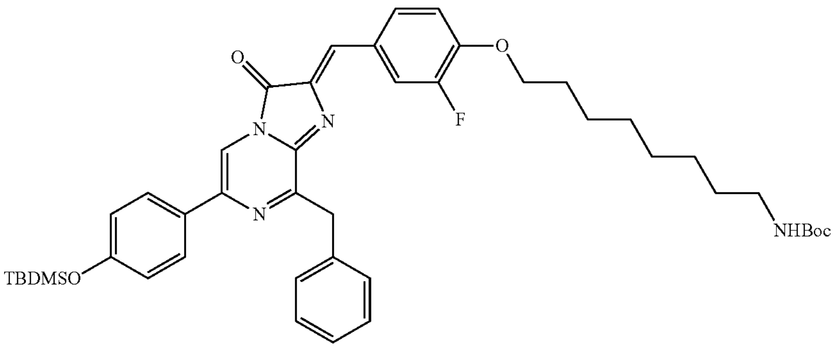 [SMILES: CC(C)(C)OC(=O)NCCCCCCCCOc1ccc(/C=C2\N=C3C(Cc4ccccc4)=NC(c4ccc(O[Si](C)(C)C(C)(C)C)cc4)=CN3C2=O)cc1F]

Following general procedure A, tert-butyl (8-(2-fluoro-4-formylphenoxy)octyl)carbamate (357 mg, 0.97 mmol) was reacted with methyl 2-((3-benzyl-5-(4-((tert-butyldimethylsilyl)oxy)phenyl)pyrazin-2-yl)amino)-2-(diethoxyphosphoryl)acetate (530 mg, 0.88 mmol) to afford crude product (360 mg) as a black solid.

Step 2. tert-butyl (8-(4-((8-benzyl-6-(4-((tert-butyldimethylsilyl)oxy)phenyl)-3-oxo-3,7-dihydroimidazo[1,2-a]pyrazin-2-yl)methyl)-2-fluorophenoxy)octyl)carbamate (JRW-0902)

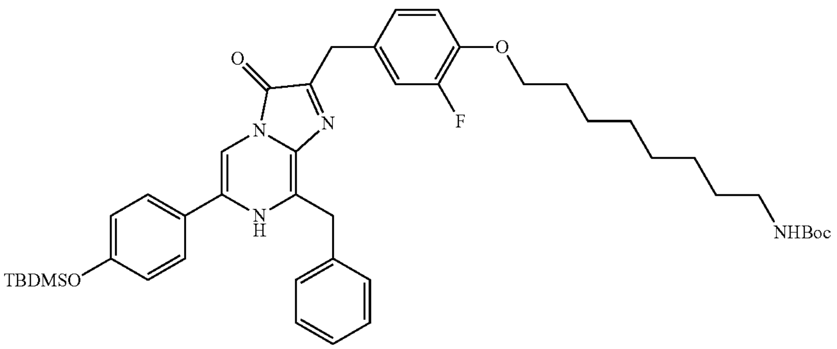 [SMILES: CC(C)(C)OC(=O)NCCCCCCCCOc1ccc(Cc2nc3c(Cc4ccccc4)[nH]c(-c4ccc(O[Si](C)(C)C(C)(C)C)cc4)cn-3c2=O)cc1F]

Following general procedure B, tert-butyl (Z)-(8-(4-((8-benzyl-6-(4-((tert-butyldimethylsilyl)oxy)phenyl)-3-oxo-imidazo[1,2-a]pyrazin-2(3H)-ylidene)methyl)-2-fluorophenoxy)octyl)carbamate (360 mg, 0.46 mmol) was reacted with sodium borohydride (87 mg, 2.3 mmol) to afford crude product as an orange solid.

Step 3. 2-(4-((8-aminooctyl)oxy)-3-fluorobenzyl)-8-benzyl-6-(4-hydroxyphenyl)imidazo[1,2-a]pyrazin-3(7H)-one (JRW-0904)

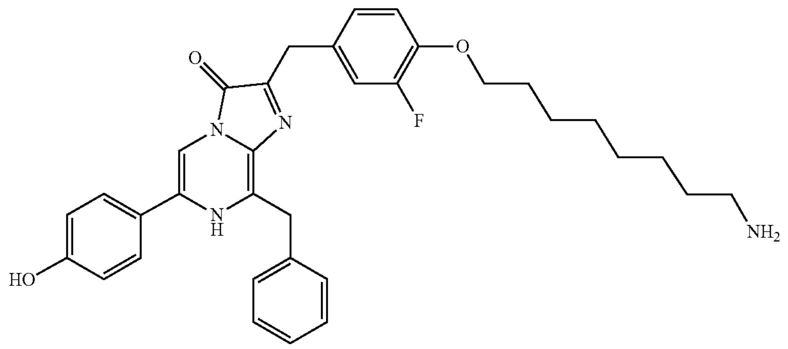 [SMILES: NCCCCCCCCOc1ccc(Cc2nc3c(Cc4ccccc4)[nH]c(-c4ccc(O)cc4)cn-3c2=O)cc1F]

Following general procedure C and D, tert-butyl (8-(4-((8-benzyl-6-(4-((tert-butyldimethylsilyl)oxy)phenyl)-3-oxo-3,7-dihydroimidazo[1,2-a]pyrazin-2-yl)methyl)-2-fluorophenoxy)octyl)carbamate was reacted with HCl/MeOH and TFA/DCM to afford the desired product (192 mg, 73% over three steps) as an orange solid. $^1$H NMR (400 MHz, $CD_3OD$) δ 7.67-7.38 (m, 4H), 7.32 (t, J=7.4 Hz, 2H), 7.28-7.23 (m, 1H), 7.15-7.02 (m, 2H), 7.03-6.96 (m, 1H), 6.95-6.86 (m, 2H), 4.43 (s, 2H), 4.12 (s, 2H), 4.02 (t, J=6.3 Hz, 2H), 2.92 (t, J=7.6 Hz, 2H), 1.87-1.74 (m, 2H), 1.74-1.60 (m, 2H), 1.57-1.47 (m, 2H), 1.46-1.38 (m, 6H); ESI MS m/z 569 $[M+H]^+$; HPLC 97.0% (AUC), $T_R$ 4.47 min; UV (MeOH) λ 438 nm, ε 5,787.

Example 8

4-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,6-dihydroxyxanthylium-9-yl)benzoate (JRW-0906)

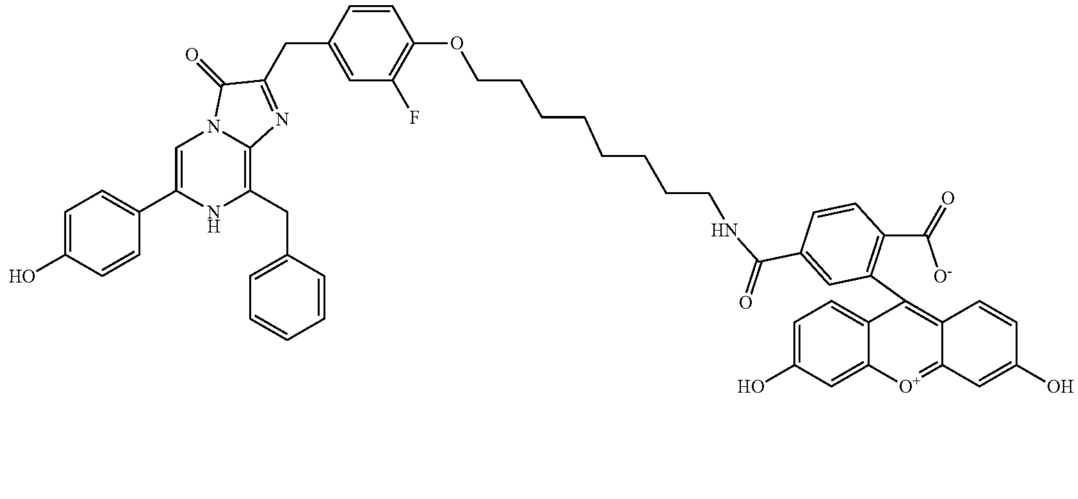 [SMILES: O=C(NCCCCCCCCOc1ccc(Cc2nc3c(Cc4ccccc4)[nH]c(-c4ccc(O)cc4)cn-3c2=O)cc1F)c1ccc(C(=O)[O-])c(-c2c3ccc(O)cc3[o+]c3cc(O)ccc23)c1]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (30 mg, 0.053 mmol) was reacted with 2-(3,6-dihydroxyxanthylium-9-yl)-4-(((2,5-dioxopyrrolidin-1-yl)oxy)carbonyl)benzoate (30 mg, 0.063 mmol) [Note: the FAM-SE was a mixture of 5- and 6-isomers] to afford the desired product (25 mg, 52%) as an orange solid. The 6-isomer is illustrated and named, but the product here is a mixture of the 5- and 6-isomers. $^1$H NMR (400 MHz, $CD_3OD$) δ 8.84 (d, J=1.7 Hz, 0.5H, isomer A), 8.52-8.44 (m, 1.5H), 8.31 (ddd, J=21.2, 8.1, 1.7 Hz, 1H), 7.89 (d, J=1.7 Hz, 0.5H, isomer B), 7.82-7.76 (m, 2H), 7.64-7.49 (m, 3H), 7.48-7.37 (m, 4H), 7.37-7.17 (m, 5H), 7.14-6.99 (m, 3H), 6.98-6.89 (m, 2H), 4.62 (s, 2H), 4.26 (s, 2H), 4.02-3.99 (m, 2H), 3.51-3.38 (m, 2H), 1.87-1.59 (m, 4H), 1.59-1.36 (m, 8H); ESI MS m/z 927 $[M+H]^+$; HPLC 89.5% (AUC), $T_R$ 5.57 min; UV (MeOH) λ 444 nm, ε 24,071.

Example 9

4-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,6-bis(dimethylamino)xanthylium-9-yl)benzoate (JRW-0912)

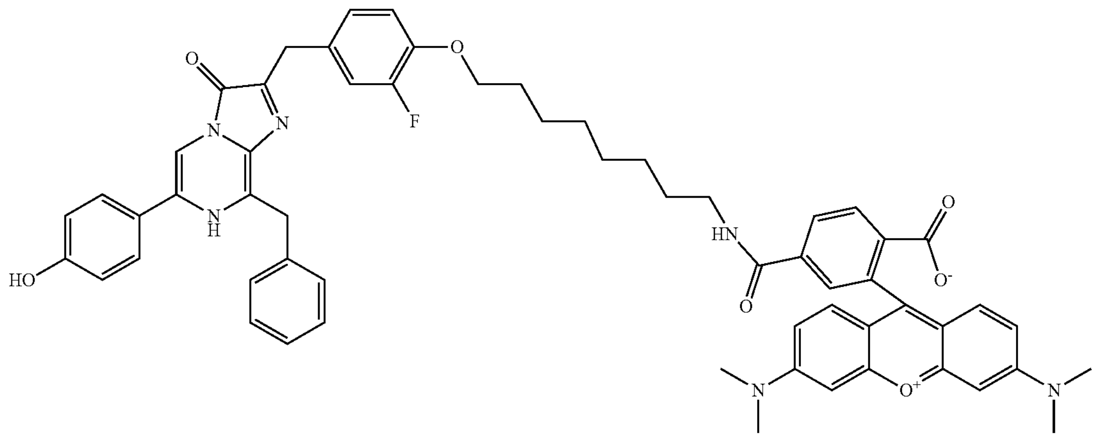 [SMILES: CN(C)c1ccc2c(-c3cc(C(=O)NCCCCCCCCOc4ccc(Cc5nc6c(Cc7ccccc7)[nH]c(-c7ccc(O)cc7)cn-6c5=O)cc4F)ccc3C(=O)[O-])c3ccc(N(C)C)cc3[o+]c2c1]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (50 mg, 0.088 mmol) was reacted with 2-(3,6-bis(dimethylamino)xanthylium-9-yl)-4-(((2,5-dioxopyrrolidin-1-yl)oxy)carbonyl)benzoate (46 mg, 0.088 mmol) to afford the desired product (18 mg, 20%) as a black red solid. Note: compound showed instability in solution. ESI MS m/z 981 $[M+H]^+$; HPLC 64.8% (AUC), $T_R$5.09 min; UV (MeOH) λ 552 nm, ε 125,445.

Example 10

3-(2-(2-aminoethoxy)ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide (JRW-0925)

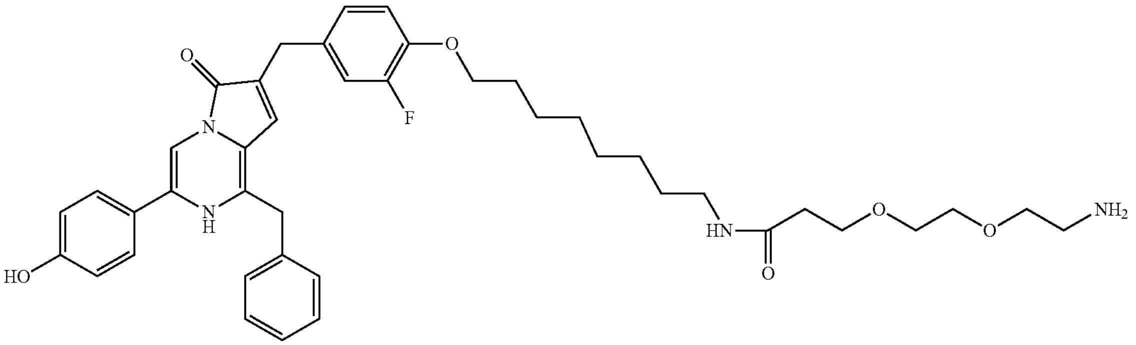 [SMILES: NCCOCCOCCC(=O)NCCCCCCCCOc1ccc(Cc2cc3c(Cc4ccccc4)[nH]c(-c4ccc(O)cc4)cn-3c2=O)cc1F]

Step 1. 4-((8-Aminooctyl)oxy)-3-fluorobenzaldehyde (JRW-0918)

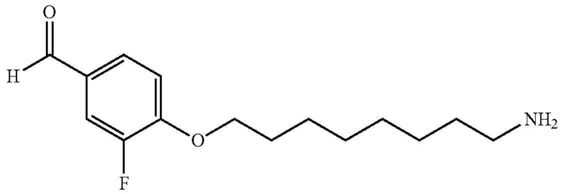 [SMILES: NCCCCCCCCOc1ccc(C=O)cc1F]

Following general procedure D, tert-butyl (8-(2-fluoro-4-formylphenoxy)octyl)carbamate (250 mg, 0.68 mmol) was reacted with trifluoroacetic acid (1 mL) to afford crude product as a colorless oil.

Step 2. Tert-butyl (2-(2-(3-((8-(2-fluoro-4-formylphenoxy)octyl)amino)-3-oxopropoxy)ethoxy)ethyl)carbamate (JRW-0919)

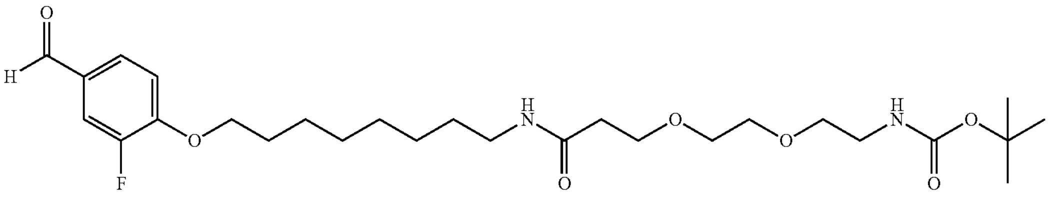 [SMILES: CC(C)(C)OC(=O)NCCOCCOCCC(=O)NCCCCCCCCOc1ccc(C=O)cc1F]

To a solution of 2,2-dimethyl-4-oxo-3,8,11-trioxa-5-aza-tetradecan-14-oic acid (226 mg, 0.82 mmol) in DMF (5 mL), 1-hydroxybenzotriazole hydrate (208 mg, 1.4 mmol), N-(3-dimethylaminopropyl)-N'-ethylcarbodiimide hydrochloride (260 mg, 1.4 mmol), and diisopropylethylamine (263 mg, 2.0 mmol) was added. 4-((8-Aminooctyl)oxy)-3-fluorobenzaldehyde (0.68 mmol) in DMF (5 mL) was added, and the mixture was heated to 60° C. for 30 min. The reaction was diluted with ethyl acetate, and the organic layer was washed with water. The organic layer was dried with sodium sulfate, filtered, concentrated, and purified with silica gel chromatography (DCM/MeOH) to afford the desired product (300 mg, 83%) as a colorless oil. $^1$H NMR (400 MHz, $CDCl_3$) δ 9.87 (d, J=2.1 Hz, 1H), 7.73-7.53 (m, 2H), 7.11-7.04 (m, 1H), 6.31 (s, 1H), 5.00 (s, 1H), 4.13 (t, J=6.5 Hz, 2H), 3.76 (t, J=5.8 Hz, 2H), 3.63 (s, 4H), 3.56 (dd, J=5.6, 4.9 Hz, 2H), 3.40-3.18 (m, 4H), 2.49 (t, J=5.8 Hz, 2H), 1.94-1.81 (m, 2H), 1.47 (s, 13H), 1.43-1.31 (m, 6H); ESI MS m/z 527 $[M+H]^+$.

Step 3. Tert-butyl (E)-(2-(2-(3-((8-(4-((1-benzyl-3-(4-((tert-butyldimethylsilyl)oxy)phenyl)-6-oxopyrrolo[1,2-a]pyrazin-7(6H)-ylidene)methyl)-2-fluorophenoxy)octyl)amino)-3-oxopropoxy)ethoxy)ethyl) carbamate (JRW-0922)

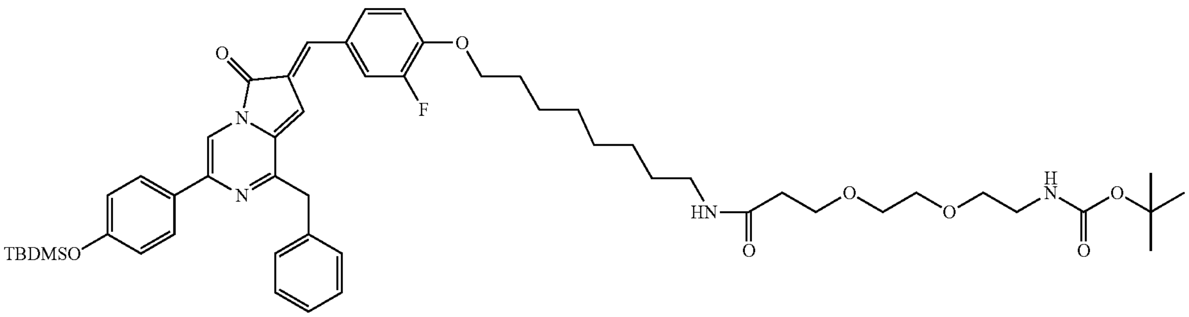 [SMILES: CC(C)(C)OC(=O)NCCOCCOCCC(=O)NCCCCCCCCOc1ccc(/C=C2\C=C3C(Cc4ccccc4)=NC(c4ccc(O[Si](C)(C)C(C)(C)C)cc4)=CN3C2=O)cc1F]

Following general procedure A, tert-butyl (2-(2-(3-((8-(2-fluoro-4-formylphenoxy)octyl)amino)-3-oxopropoxy) ethoxy)ethyl)carbamate (285 mg, 0.54 mmol) was reacted with methyl 2-((3-benzyl-5-(4-((tert-butyldimethylsilyl) oxy)phenyl)pyrazin-2-yl)amino)-2-(diethoxyphosphoryl) acetate (325 mg, 0.54 mmol) to afford crude product (430 mg) as a black solid.

Step 4. Tert-butyl (2-(2-(3-((8-(4-((1-benzyl-3-(4-((tert-butyldimethylsilyl)oxy)phenyl)-6-oxo-2,6-dihydropyrrolo[1,2-a]pyrazin-7-yl)methyl)-2-fluorophenoxy)octyl)amino)-3-oxopropoxy)ethoxy)ethyl) carbamate (JRW-0923)

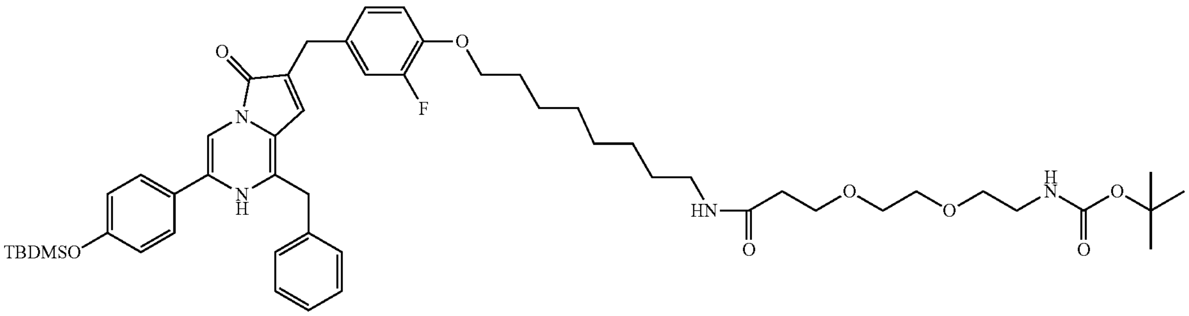 [SMILES: CC(C)(C)OC(=O)NCCOCCOCCC(=O)NCCCCCCCCOc1ccc(Cc2cc3c(Cc4ccccc4)[nH]c(-c4ccc(O[Si](C)(C)C(C)(C)C)cc4)cn-3c2=O)cc1F]

Following general procedure B, tert-butyl (E)-(2-(2-(3-((8-(4-((1-benzyl-3-(4-((tert-butyldimethylsilyl)oxy)phenyl)-6-oxopyrrolo[1,2-a]pyrazin-7(6H)-ylidene)methyl)-2-fluorophenoxy)octyl)amino)-3-oxopropoxy)ethoxy)ethyl) carbamate (430 mg, 0.46 mmol) was reacted with sodium borohydride (86 mg, 2.3 mmol) to afford crude product (370 mg) as an orange solid.

Step 5. -(2-(2-aminoethoxy)ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy) octyl)propanamide (JRW-0925)

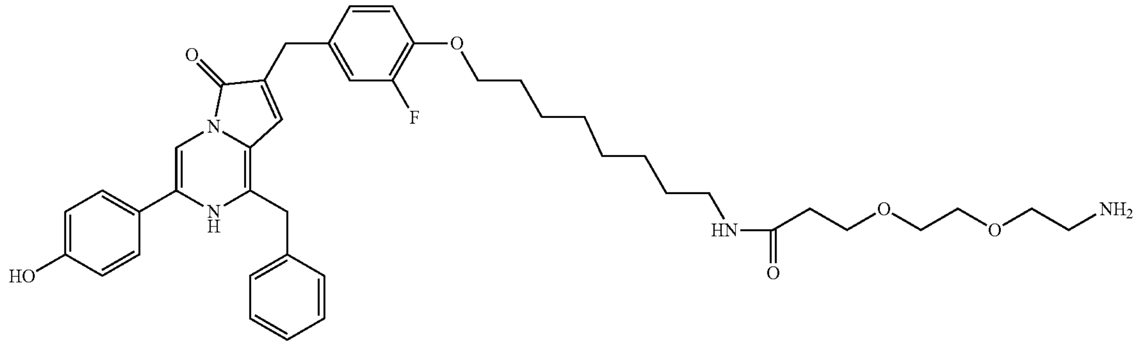 [SMILES: NCCOCCOCCC(=O)NCCCCCCCCOc1ccc(Cc2cc3c(Cc4ccccc4)[nH]c(-c4ccc(O)cc4)cn-3c2=O)cc1F]

Following general procedure C and D, tert-butyl (2-(2-(3-((8-(4-((1-benzyl-3-(4-((tert-butyldimethylsilyl)oxy)phenyl)-6-oxo-2,6-dihydropyrrolo[1,2-a]pyrazin-7-yl)methyl)-2-fluorophenoxy)octyl)amino)-3-oxopropoxy)ethoxy)ethyl) carbamate (370 mg, 0.39 mmol) was reacted with HCl/MeOH and TFA/DCM to afford the desired product (180 mg, 46% over three steps) as an orange solid. $^1$H NMR (400 MHz, $CD_3OD$) δ 7.70-7.38 (m, 5H), 7.36-7.21 (m, 3H), 7.16-6.96 (m, 3H), 6.94-6.87 (m, 2H), 4.43 (s, 2H), 4.12 (s, 2H), 4.02 (t, J=6.4 Hz, 2H), 3.80-3.59 (m, 8H), 3.19 (t, J=7.0 Hz, 2H), 3.15-3.07 (m, 2H), 2.45 (t, J=6.1 Hz, 2H), 1.84-1.71 (m, 2H), 1.56-1.45 (m, 4H), 1.45-1.29 (m, 6H); ESI MS m/z 727 $[M+H]^+$; HPLC 95.3% (AUC), $T_R$ 4.36 min; UV (MeOH) λ 436 nm, ε 6,426.

Example 11

4-((2-(2-(3-((8-(4-((1-benzyl-3-(4-hydroxyphenyl)-6-oxo-2,6-dihydropyrrolo[1,2-a]pyrazin-7-yl) methyl)-2-fluorophenoxy)octyl)amino)-3-oxo-propoxy)ethoxy)ethyl)carbamoyl)-2-(3,6-dihydroxyxanthylium-9-yl)benzoate (JRW-0926)

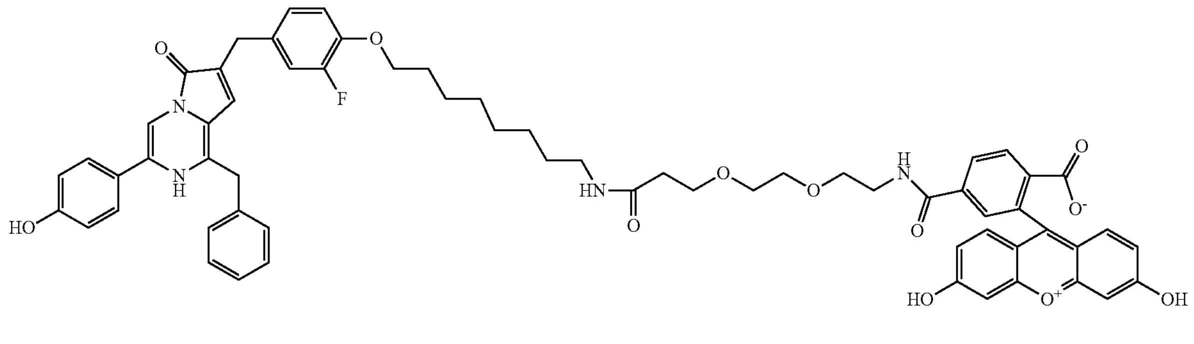 [SMILES: O=C(CCOCCOCCNC(=O)c1ccc(C(=O)[O-])c(-c2c3ccc(O)cc3[o+]c3cc(O)ccc23)c1)NCCCCCCCCOc1ccc(Cc2cc3c(Cc4ccccc4)[nH]c(-c4ccc(O)cc4)cn-3c2=O)cc1F]

Following general procedure G, -(2-(2-aminoethoxy) ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide (50 mg, 0.069 mmol) was reacted with 2-(3,6-dihydroxyxanthylium-9-yl)-4-(((2,5-dioxopyrrolidin-1-yl)oxy)carbonyl)benzoate (32 mg, 0.069 mmol) [Note: the FAM-SE was a mixture of 5- and 6-isomers] to afford the desired product (35 mg, 47%) as an orange brown solid. The 6-isomer is illustrated and named, but the product here is a mixture of the 5- and 6-isomers. $^1$H NMR (400 MHz, $CD_3OD$) δ 8.85 (d, J=1.7 Hz, 0.5H, isomer A), 8.53-8.44 (m, 1.5H), 8.40-8.26 (m, 1H), 7.96-7.88 (m, 0.5H, isomer B), 7.82-7.76 (m, 2H), 7.64-7.48 (m, 4H), 7.48-7.42 (m, 2H), 7.42-7.37 (m, 2H), 7.36-7.28 (m, 2H), 7.28-7.18 (m, 3H), 7.13-6.97 (m, 3H), 6.97-6.89 (m, 2H), 4.63 (s, 2H), 4.27 (s, 2H), 4.02-3.98 (m, 2H), 3.82-3.53 (m, 10H), 3.28-3.13 (m, 2H), 2.59-2.52 (m, 1H), 2.51-2.43 (m, 1H), 1.82-1.68 (m, 2H), 1.58-1.41 (m, 4H), 1.42-1.27 (m, 8H); ESI MS m/z 1086 $[M+H]^+$; HPLC 74.9% (AUC), $T_R$ 5.08 min; UV (MeOH) λ 444 nm, ε 23,614.

Example 12

4-((2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)carbamoyl)-2-(3,6-bis(dimethylamino)xanthylium-9-yl)benzoate (JRW-0927)

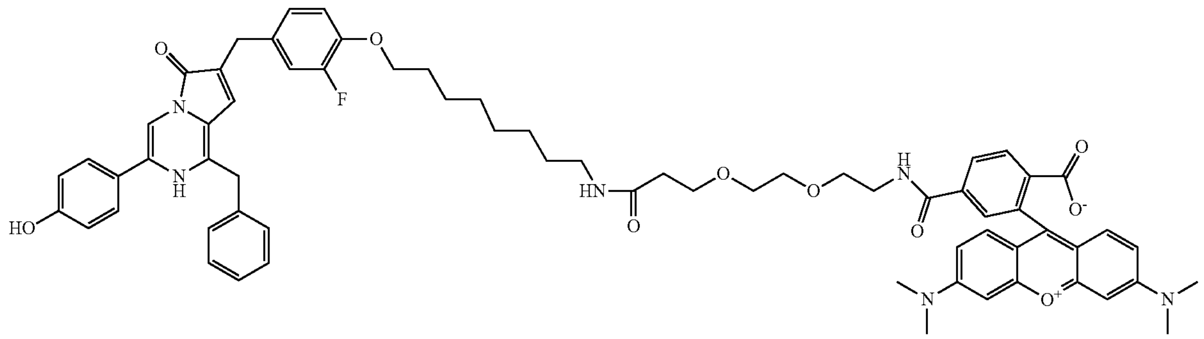 [SMILES: CN(C)c1ccc2c(-c3cc(C(=O)NCCOCCOCCC(=O)NCCCCCCCCOc4ccc(Cc5cc6c(Cc7ccccc7)[nH]c(-c7ccc(O)cc7)cn-6c5=O)cc4F)ccc3C(=O)[O-])c3ccc(N(C)C)cc3[o+]c2c1]

Following general procedure G, -(2-(2-aminoethoxy) ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide (50 mg, 0.068 mmol) was reacted with 2-(3,6-bis(dimethylamino)xanthylium-9-yl)-4-(((2,5-dioxopyrrolidin-1-yl)oxy)carbonyl)benzoate (36 mg, 0.068 mmol) to afford the desired product (18 mg, 23%) as a black red solid. Note: compound showed instability in solution. ESI MS m/z 1140 $[M+H]^+$; HPLC 37.6% (AUC), $T_R$4.79 min; UV (MeOH) λ 552 nm, ε 89,415.

Example 13

6-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-3-oxo-3H-spiro[isobenzofuran-1,9'-xanthene]-3',6'-diyl diacetate (JRW-0972)

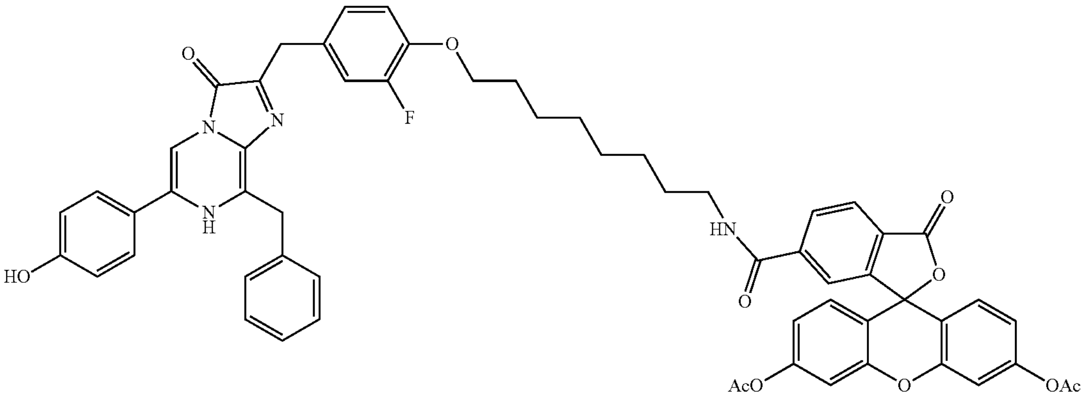 [SMILES: CC(=O)Oc1ccc2c(c1)Oc1cc(OC(C)=O)ccc1C21OC(=O)c2ccc(C(=O)NCCCCCCCCOc3ccc(Cc4nc5c(Cc6ccccc6)[nH]c(-c6ccc(O)cc6)cn-5c4=O)cc3F)cc21]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (50 mg, 0.068 mmol) was reacted with 6-(((2,5-dioxopyrrolidin-1-yl)oxy)carbonyl)-3-oxo-3H-spiro[isobenzofuran-1,9'-xanthene]-3',6'-diyl diacetate (58 mg, 0.10 mmol) [Note: the FAM-SE was a mixture of 5- and 6-isomers] to afford the desired product (42 mg, 47%) as an orange solid. The 6-isomer is illustrated and named, but the product here is a mixture of the 5- and 6-isomers. Note: compound showed instability in solution. ESI MS m/z 1011 $[M+H]^+$; HPLC 45.7% (AUC), $T_R$ 5.83 min; UV (MeOH) λ 444 nm, ε 32,826.

Example 14

2-(4-((6-azidohexyl)oxy)-3-fluorobenzyl)-8-benzyl-6-(4-hydroxyphenyl)imidazo[1,2-a]pyrazin-3(7H)-one (JRW-0975)

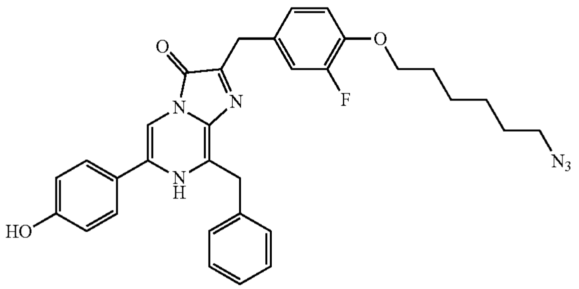 [SMILES: [N-]=[N+]=NCCCCCCOc1ccc(Cc2nc3c(Cc4ccccc4)[nH]c(-c4ccc(O)cc4)cn-3c2=O)cc1F]

Step 1. 4-((6-Azidohexyl)oxy)-3-fluorobenzaldehyde (JRW-0891)

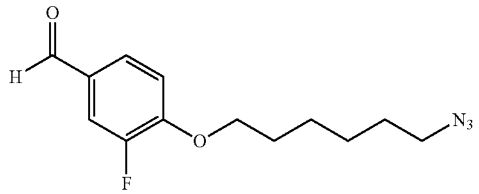 [SMILES: [N-]=[N+]=NCCCCCCOc1ccc(C=O)cc1F]

To a solution of 4-((6-bromohexyl)oxy)-3-fluorobenzaldehyde (250 mg, 0.082 mmol) in DMF (5 mL), sodium azide (107 mg, 1.6 mmol) was added. The reaction was heated to 60° C. for 18 h. The reaction was diluted with ethyl acetate, and the organic layer was washed with water. The organic layer was dried with sodium sulfate, filtered, and concentrated to afford crude product (220 mg) as a colorless oil. $^1H$ NMR (400 MHz, $CDCl_3$) δ 9.88 (d, J=2.1 Hz, 1H), 7.73-7.53 (m, 2H), 7.08 (t, J=8.2 Hz, 1H), 4.15 (t, J=6.4 Hz, 2H), 3.32 (t, J=6.8 Hz, 2H), 1.90 (dt, J=8.0, 6.4 Hz, 2H), 1.81-1.40 (m, 6H).

Step 2. 2-(4-((6-Azidohexyl)oxy)-3-fluorobenzylidene)-8-benzyl-6-(4-((tert-butyldimethylsilyl)oxy)phenyl)imidazo[1,2-a]pyrazin-3(2H)-one (JRW-0969)

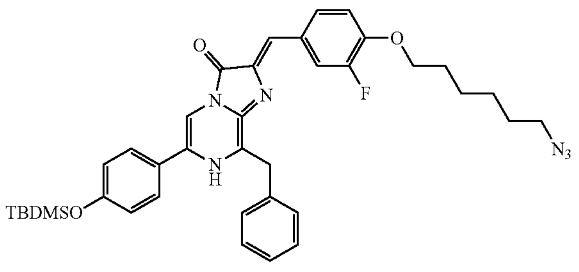

Following general procedure A, 4-((6-azidohexyl)oxy)-3-fluorobenzaldehyde (106 mg, 0.40 mmol) was reacted with methyl 2-((3-benzyl-5-(4-((tert-butyldimethylsilyl)oxy)phenyl)pyrazin-2-yl)amino)-2-(diethoxyphosphoryl)acetate (200 mg, 0.33 mmol) to afford crude product (120 mg) as a black solid.

Step 3. 2-(4-((6-Azidohexyl)oxy)-3-fluorobenzyl)-8-benzyl-6-(4-((tert-butyldimethylsilyl)oxy)phenyl)imidazo[1,2-a]pyrazin-3(7H)-one (JRW-0974)

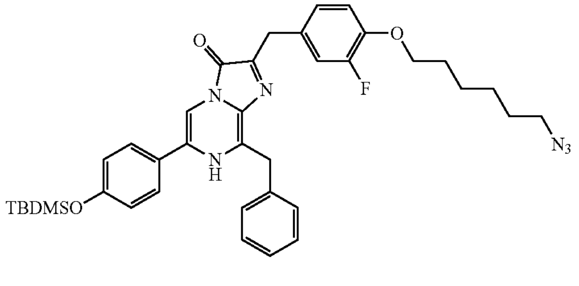 [SMILES: CC(C)(C)[Si](C)(C)Oc1ccc(-c2cn3c(=O)c(Cc4ccc(OCCCCCCN=[N+]=[N-])c(F)c4)nc-3c(Cc3ccccc3)[nH]2)cc1]

Following general procedure B, 2-(4-((6-azidohexyl)oxy)-3-fluorobenzylidene)-8-benzyl-6-(4-((tert-butyldimethylsilyl)oxy)phenyl)imidazo[1,2-a]pyrazin-3(2H)-one (120 mg, 0.18 mmol) was reacted with sodium borohydride (20 mg, 0.53 mmol) to afford crude product as a yellow solid.

Step 4. 2-(4-((6-Azidohexyl)oxy)-3-fluorobenzyl)-8-benzyl-6-(4-hydroxyphenyl)imidazo[1,2-a]pyrazin-3(7H)-one (JRW-0975)

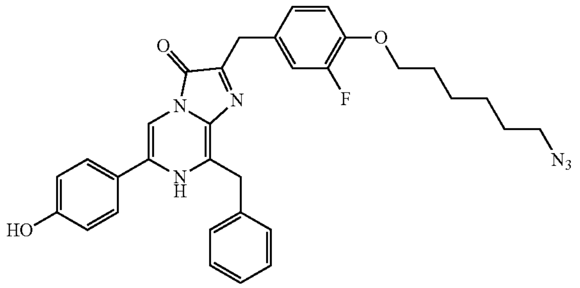 [SMILES: [N-]=[N+]=NCCCCCCOc1ccc(Cc2nc3c(Cc4ccccc4)[nH]c(-c4ccc(O)cc4)cn-3c2=O)cc1F]

Following general procedure C, 2-(4-((6-azidohexyl)oxy)-3-fluorobenzyl)-8-benzyl-6-(4-((tert-butyldimethylsilyl)oxy)phenyl)imidazo[1,2-a]pyrazin-3(7H)-one (0.18 mmol) was reacted with HCl/MeOH to afford the desired product (67 mg, 36% over three steps) as an orange solid. $^1$H NMR (400 MHz, $CD_3OD$) δ 7.67-7.43 (m, 3H), 7.43-7.37 (m, 2H), 7.35-7.20 (m, 3H), 7.15-7.03 (m, 2H), 6.98 (t, J=8.5 Hz, 1H), 6.92-6.86 (m, 2H), 4.41 (s, 2H), 4.11 (s, 2H), 4.01 (t, J=6.3 Hz, 2H), 3.29 (t, J=6.8 Hz, 2H), 1.77 (dt, J=8.0, 6.3 Hz, 2H), 1.70-1.38 (m, 6H); ESI MS m/z 567 $[M+H]^+$; HPLC 99.0% (AUC), $T_R$ 5.85 min; UV (MeOH) λ 438 nm, ε 10,419.

Example 15

6-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-4',5'-dichloro-2',7'-dimethoxy-3-oxo-3H-spiro[isobenzofuran-1,9'-xanthene]-3',6'-diyl diacetate (JRW-0986)

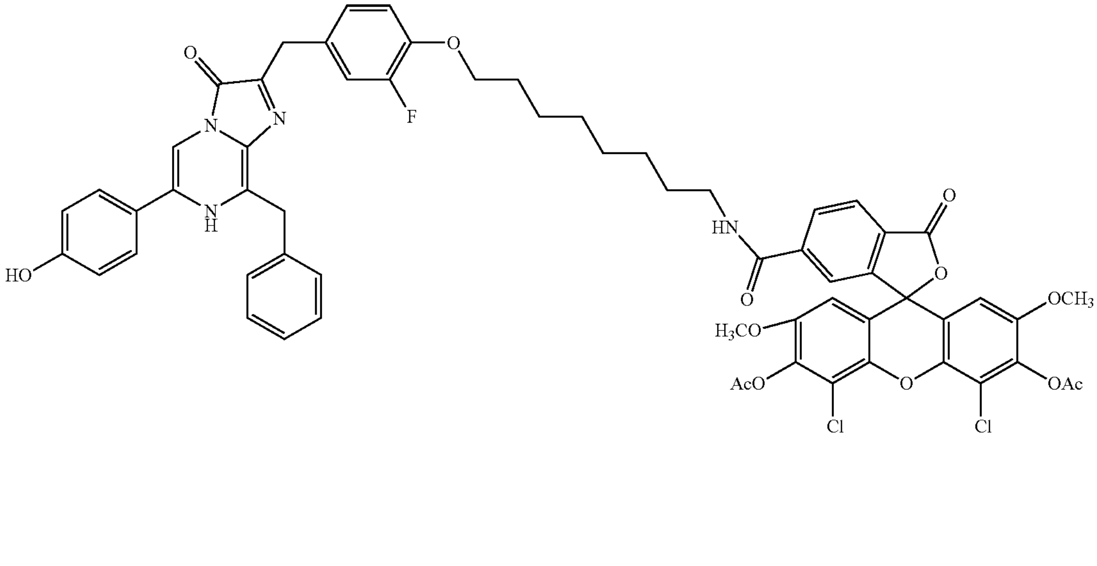 [SMILES: COc1cc2c(c(Cl)c1OC(C)=O)Oc1c(cc(OC)c(OC(C)=O)c1Cl)C21OC(=O)c2ccc(C(=O)NCCCCCCCCOc3ccc(Cc4nc5c(Cc6ccccc6)[nH]c(-c6ccc(O)cc6)cn-5c4=O)cc3F)cc21]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (42 mg, 0.074 mmol) was reacted with 4',5'-dichloro-6-(((2,5-dioxopyrrolidin-1-yl)oxy)carbonyl)-2',7'-dimethoxy-3-oxo-3H-spiro[isobenzofuran-1,9'-xanthene]-3',6'-diyl diacetate (55 mg, 0.081 mmol) [Note: the JOE-SE was a mixture of 5- and 6-isomers] to afford the desired product (40 mg, 47%) as a red solid. The 6-isomer is illustrated and named, but the product here is a mixture of the 5- and 6-isomers. Note: compound showed instability in solution. ESI MS m/z 1141 $[M+H]^+$; HPLC 73.4% (AUC), $T_R$ 6.45 min; UV (MeOH) λ 472 nm, ε 4,433.

Example 16

8-benzyl-6-(4-hydroxyphenyl)-2-((2-oxo-2H-chromen-6-yl)methyl)imidazo[1,2-a]pyrazin-3(7H)-one (JRW-0995)

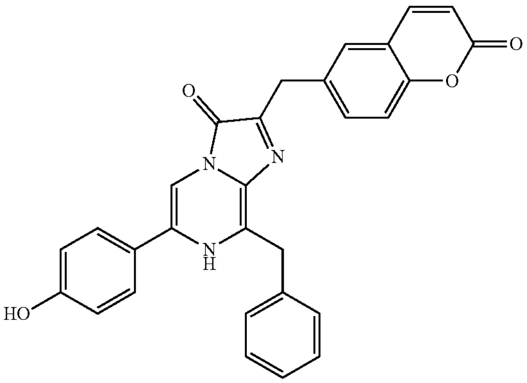 [SMILES: O=c1ccc2cc(Cc3nc4c(Cc5ccccc5)[nH]c(-c5ccc(O)cc5)cn-4c3=O)ccc2o1]

Step 1. 8-Benzyl-6-(4-((tert-butyldimethylsilyl)oxy)phenyl)-2-((2-oxo-2H-chromen-6-yl)methylene)imidazo[1,2-a]pyrazin-3(2H)-one (JRW-0992)

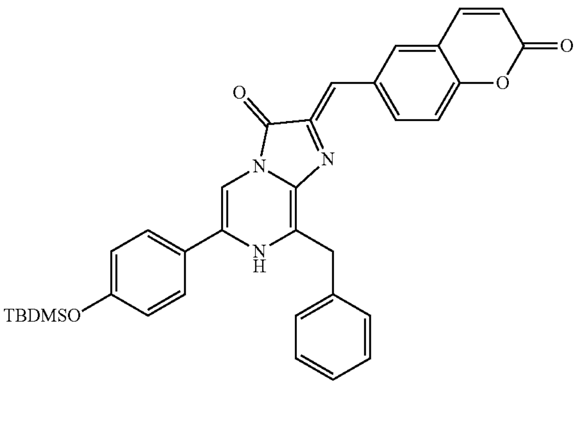

Following general procedure A, 2-oxo-2H-chromene-6-carbaldehyde (52 mg, 0.30 mmol) was reacted with methyl 2-((3-benzyl-5-(4-((tert-butyldimethylsilyl)oxy)phenyl)pyrazin-2-yl)amino)-2-(diethoxyphosphoryl)acetate (150 mg, 0.25 mmol) to afford crude product as a black solid.

Step 2. 8-benzyl-6-(4-((tert-butyldimethylsilyl)oxy)phenyl)-2-((2-oxo-2H-chromen-6-yl)methyl)imidazo[1,2-a]pyrazin-3(7H)-one (JRW-0993)

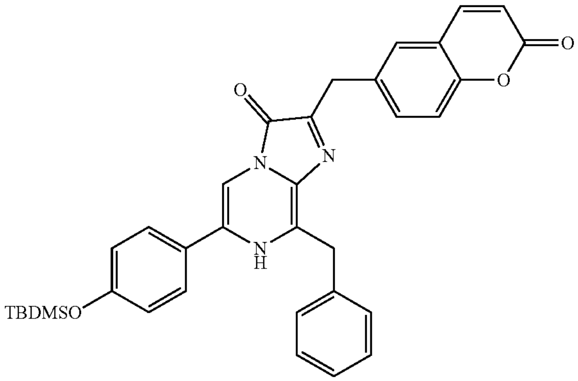 [SMILES: CC(C)(C)[Si](C)(C)Oc1ccc(-c2cn3c(=O)c(Cc4ccc5oc(=O)ccc5c4)nc-3c(Cc3ccccc3)[nH]2)cc1]

Following general procedure B, 8-benzyl-6-(4-((tert-butyldimethylsilyl)oxy)phenyl)-2-((2-oxo-2H-chromen-6-yl)methylene)imidazo[1,2-a]pyrazin-3(2H)-one (0.25 mmol) was reacted with sodium borohydride (47 mg, 1.2 mmol) to afford crude product (45 mg) as an orange solid.

Step 3. 8-benzyl-6-(4-hydroxyphenyl)-2-((2-oxo-2H-chromen-6-yl)methyl)imidazo[1,2-a]pyrazin-3(7H)-one (JRW-0995)

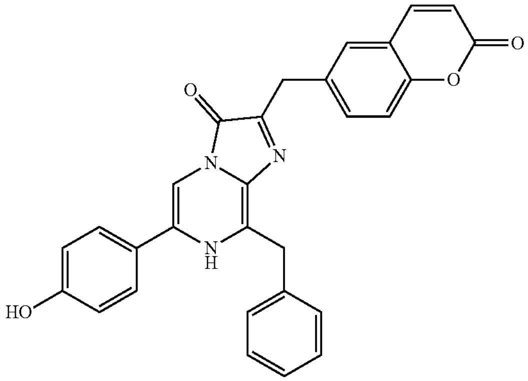 [SMILES: O=c1ccc2cc(Cc3nc4c(Cc5ccccc5)[nH]c(-c5ccc(O)cc5)cn-4c3=O)ccc2o1]

Following general procedure C, 8-benzyl-6-(4-((tert-butyldimethylsilyl)oxy)phenyl)-2-((2-oxo-2H-chromen-6-yl)methyl)imidazo[1,2-a]pyrazin-3(7H)-one (45 mg, 0.076 mmol) was reacted with HCl/MeOH to afford the desired product (32 mg, 27% over three steps) as an orange solid. $^1H$ NMR (400 MHz, $CD_3OD$) δ 7.90 (d, J=9.6 Hz, 1H), 7.68-7.53 (m, 3H), 7.51-7.35 (m, 4H), 7.35-7.18 (m, 4H), 6.93-6.86 (m, 2H), 6.41 (d, J=9.5 Hz, 1H), 4.41 (s, 2H), 4.25 (s, 2H); ESI MS m/z 476 $[M+H]^+$; HPLC 85.3% (AUC), $T_R$ 4.47 min; UV (MeOH) λ 439 nm, ε 8214.

Example 17

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-11-oxo-2,3,6,7-tetrahydro-1H,5H,11H-pyrano[2,3-f]pyrido[3,2,1-ij]quinoline-10-carboxamide (JRW-1023)

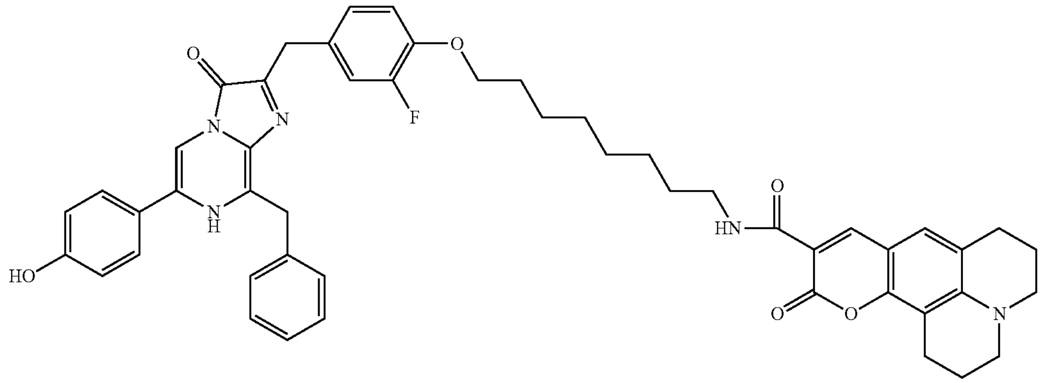 [SMILES: O=C(NCCCCCCCCOc1ccc(Cc2nc3c(Cc4ccccc4)[nH]c(-c4ccc(O)cc4)cn-3c2=O)cc1F)c1cc2cc3c4c(c2oc1=O)CCCN4CCC3]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (50 mg, 0.088 mmol) was reacted with 2,5-dioxopyrrolidin-1-yl 11-oxo-2,3,6,7-tetrahydro-1H,5H,11H-pyrano[2,3-f]pyrido[3,2,1-ij]quinoline-10-carboxylate (67 mg, 0.17 mmol) to afford the desired product (24 mg, 33%) as an orange solid. ESI MS m/z 836 $[M+H]^+$; HPLC 76.0% (AUC), $T_R$ 6.43 min.

Example 18

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-7-hydroxy-2-oxo-2H-chromene-3-carboxamide (JRW-1018)

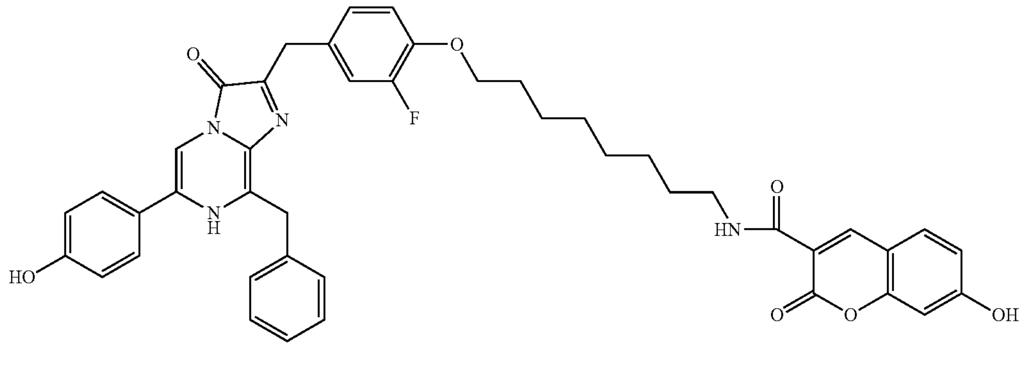 [SMILES: O=C(NCCCCCCCCOc1ccc(Cc2nc3c(Cc4ccccc4)[nH]c(-c4ccc(O)cc4)cn-3c2=O)cc1F)c1cc2ccc(O)cc2oc1=O]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (41 mg, 0.072 mmol) was reacted with 2,5-dioxopyrrolidin-1-yl 7-hydroxy-2-oxo-2H-chromene-3-carboxylate (43 mg, 0.14 mmol) to afford the desired product (36 mg, 67%) as a brown solid. $^1$H NMR (400 MHz, $CD_3OD$) δ 8.71 (s, 1H), 8.45 (s, 1H), 7.84-7.69 (m, 2H), 7.63 (d, J=8.7 Hz, 1H), 7.53 (s, 1H), 7.48-7.39 (m, 2H), 7.35-7.18 (m, 3H), 7.12-6.96 (m, 3H), 6.96-6.85 (m, 3H), 6.75 (d, J=2.3 Hz, 1H), 4.61 (s, 2H), 4.24 (s, 2H), 4.00 (t, J=6.4 Hz, 2H), 3.40-3.35 (m, 2H), 1.81-1.69 (m, 2H), 1.66-1.53 (m, 2H), 1.53-1.33 (m, 8H); ESI MS m/z 757 $[M+H]^+$; HPLC 91.2% (AUC), $T_R$ 5.69 min; UV (MeOH) λ 350 nm, ε 23646.

Example 19

2-(4-((8-azidooctyl)oxy)-3-fluorobenzyl)-8-benzyl-6-(4-hydroxyphenyl)imidazo[1,2-a]pyrazin-3(7H)-one (JRW-1022)

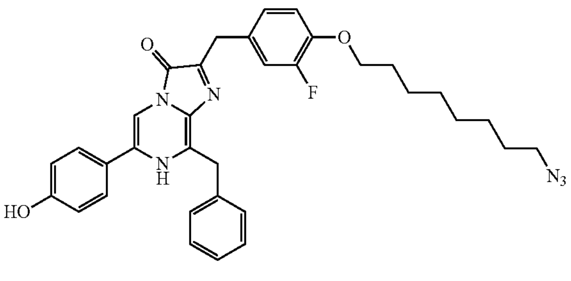 [SMILES: [N-]=[N+]=NCCCCCCCCOc1ccc(Cc2nc3c(Cc4ccccc4)[nH]c(-c4ccc(O)cc4)cn-3c2=O)cc1F]

Step 1. 4-((8-Bromooctyl)oxy)-3-fluorobenzaldehyde (JRW-1016)

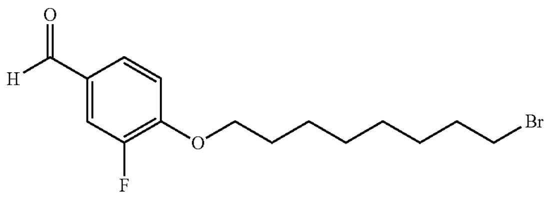 [SMILES: [N-]=[N+]=NCCCCCCCCOc1ccc(C=O)cc1F]

To a solution of 3-fluoro-4-hydroxybenzaldehyde (1.1 g, 7.9 mmol) in acetonitrile (20 mL), 1,8-dibromooctane (2.8 g, 10 mmol) and cesium carbonate (3.1 g, 9.4 mmol) was added. The reaction was heated to 60° C. for 18 h. The reaction was diluted with ethyl acetate, and the organic layer was washed with water. The organic layer was dried with sodium sulfate, filtered, and concentrated to afford desired product (1.56 g, 60%) as a colorless oil. $^1$H NMR (400 MHz, $CDCl_3$) δ 9.87 (d, J=2.1 Hz, 1H), 7.85-7.48 (m, 2H), 7.08 (t, J=8.2 Hz, 1H), 4.13 (t, J=6.5 Hz, 2H), 3.43 (t, J=6.8 Hz, 2H), 2.00-1.73 (m, 4H), 1.73-1.20 (m, 8H).

Step 2. 4-((8-Azidooctyl)oxy)-3-fluorobenzaldehyde (JRW-1017)

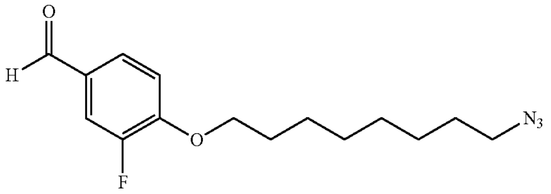

To a solution of 4-((8-bromooctyl)oxy)-3-fluorobenzaldehyde (250 mg, 0.075 mmol) in DMF (5 mL), sodium azide (98 mg, 1.5 mmol) was added. The reaction was heated to 60° C. for 18 h. The reaction was diluted with ethyl acetate, and the organic layer was washed with water. The organic layer was dried with sodium sulfate, filtered, and concentrated to afford crude product (220 mg) as a colorless oil. $^1$H NMR (400 MHz, $CDCl_3$) δ 9.87 (d, J=2.1 Hz, 1H), 7.80-7.48 (m, 2H), 7.25-6.87 (m, 1H), 4.13 (t, J=6.5 Hz, 2H), 3.29 (t, J=6.9 Hz, 2H), 2.00-1.75 (m, 2H), 1.75-1.24 (m, 10H).

Step 3. 2-(4-((8-Azidooctyl)oxy)-3-fluorobenzylidene)-8-benzyl-6-(4-((tert-butyldimethylsilyl)oxy)phenyl)imidazo[1,2-a]pyrazin-3(2H)-one (JRW-1020)

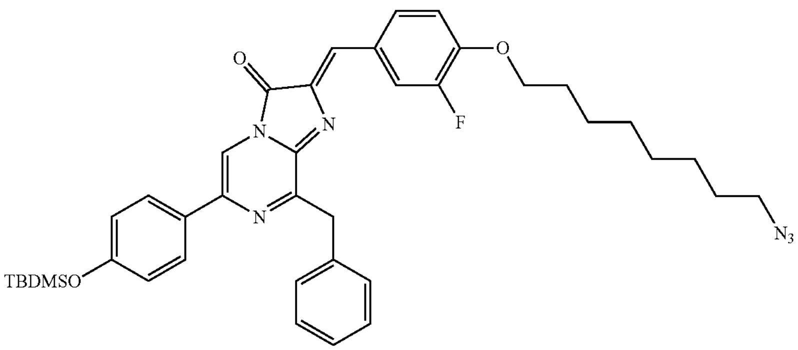 [SMILES: CC(C)(C)[Si](C)(C)Oc1ccc(C2=CN3C(=O)/C(=C/c4ccc(OCCCCCCCCN=[N+]=[N-])c(F)c4)N=C3C(Cc3ccccc3)=N2)cc1]

Following general procedure A, 4-((8-azidooctyl)oxy)-3-fluorobenzaldehyde (64 mg, 0.22 mmol) was reacted with methyl 2-((3-benzyl-5-(4-((tert-butyldimethylsilyl)oxy)phenyl)pyrazin-2-yl)amino)-2-(diethoxyphosphoryl)acetate (110 mg, 0.18 mmol) to afford crude product as a black solid.

Step 4. 2-(4-((8-Azidooctyl)oxy)-3-fluorobenzyl)-8-benzyl-6-(4-((tert-butyldimethylsilyl)oxy)phenyl)imidazo[1,2-a]pyrazin-3(7H)-one (JRW-1021)

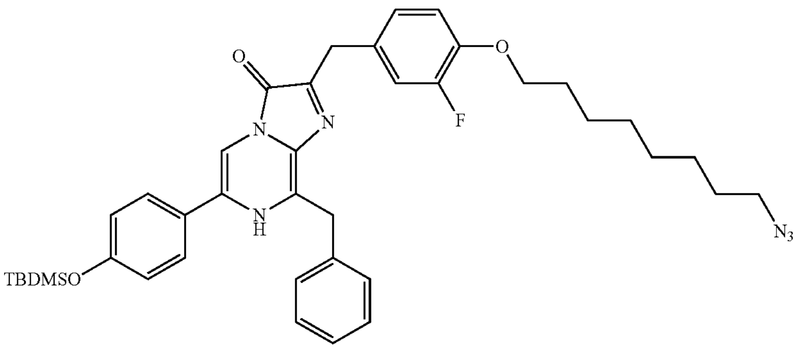 [SMILES: CC(C)(C)[Si](C)(C)Oc1ccc(-c2cn3c(=O)c(Cc4ccc(OCCCCCCCCN=[N+]=[N-])c(F)c4)nc-3c(Cc3ccccc3)[nH]2)cc1]

Following general procedure B, 2-(4-((8-azidooctyl)oxy)-3-fluorobenzylidene)-8-benzyl-6-(4-((tert-butyldimethylsilyl)oxy)phenyl)imidazo[1,2-a]pyrazin-3(2H)-one (0.18 mmol) was reacted with sodium borohydride (20 mg, 0.54 mmol) to afford crude product as a yellow solid.

Step 5. 2-(4-((8-azidooctyl)oxy)-3-fluorobenzyl)-8-benzyl-6-(4-hydroxyphenyl)imidazo[1,2-a]pyrazin-3(7H)-one (JRW-1022)

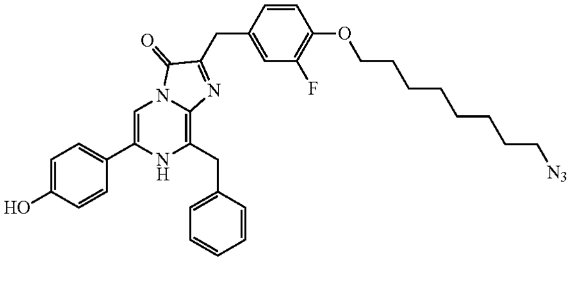 [SMILES: [N-]=[N+]=NCCCCCCCCOc1ccc(Cc2nc3c(Cc4ccccc4)[nH]c(-c4ccc(O)cc4)cn-3c2=O)cc1F]

Following general procedure C, 2-(4-((8-azidooctyl)oxy)-3-fluorobenzyl)-8-benzyl-6-(4-((tert-butyldimethylsilyl)oxy)phenyl)imidazo[1,2-a]pyrazin-3(7H)-one (0.18 mmol) was reacted with HCl/MeOH to afford the desired product (64 mg, 60% over three steps) as an orange solid. $^1H$ NMR (400 MHz, $CD_3OD$) δ 7.69-7.37 (m, 5H), 7.35-7.20 (m, 3H), 7.16-7.03 (m, 2H), 6.98 (t, J=8.5 Hz, 1H), 6.93-6.87 (m, 2H), 4.42 (s, 2H), 4.11 (s, 2H), 4.01 (t, J=6.4 Hz, 2H), 3.27 (t, J=6.9 Hz, 2H), 1.85-1.71 (m, 2H), 1.67-1.30 (m, 10H); ESI MS m/z 595 $[M+H]^+$; HPLC 99.2% (AUC), $T_R$ 6.25 min; UV (MeOH) λ 438 nm, ε 10,536.

Example 20

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(2,7-difluoro-3,6-dihydroxyxanthylium-9-yl)benzoate (JRW-1058)

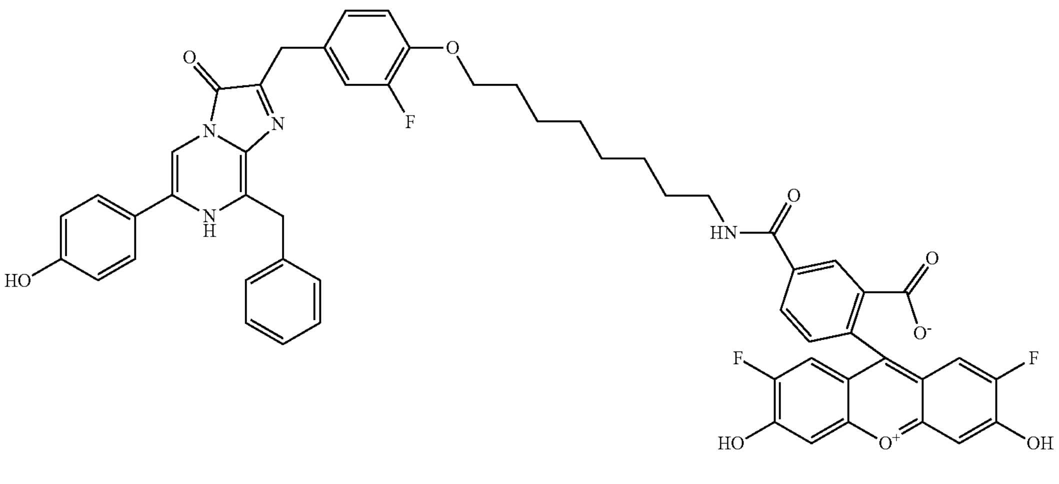 [SMILES: O=C(NCCCCCCCCOc1ccc(Cc2nc3c(Cc4ccccc4)[nH]c(-c4ccc(O)cc4)cn-3c2=O)cc1F)c1ccc(-c2c3cc(F)c(O)cc3[o+]c3cc(O)c(F)cc23)c(C(=O)[O-])c1]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (15 mg, 0.026 mmol) was reacted with 2,5-dioxopyrrolidin-1-yl 2',7'-difluoro-3',6'-dihydroxy-3-oxo-3H-spiro[isobenzofuran-1,9'-xanthene]-5-carboxylate (13 mg, 0.026 mmol) to afford the desired product (12 mg, 48%) as a red solid. ESI MS m/z 963 $[M+H]^+$; HPLC 58.1% (AUC), $T_R$ 5.50 min; UV (MeOH) λ 280 nm, ε 21,600.

Example 21

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,11-dihydroxydibenzo[c,h]xanthen-14-ium-7-yl)benzoate (JRW-1059)

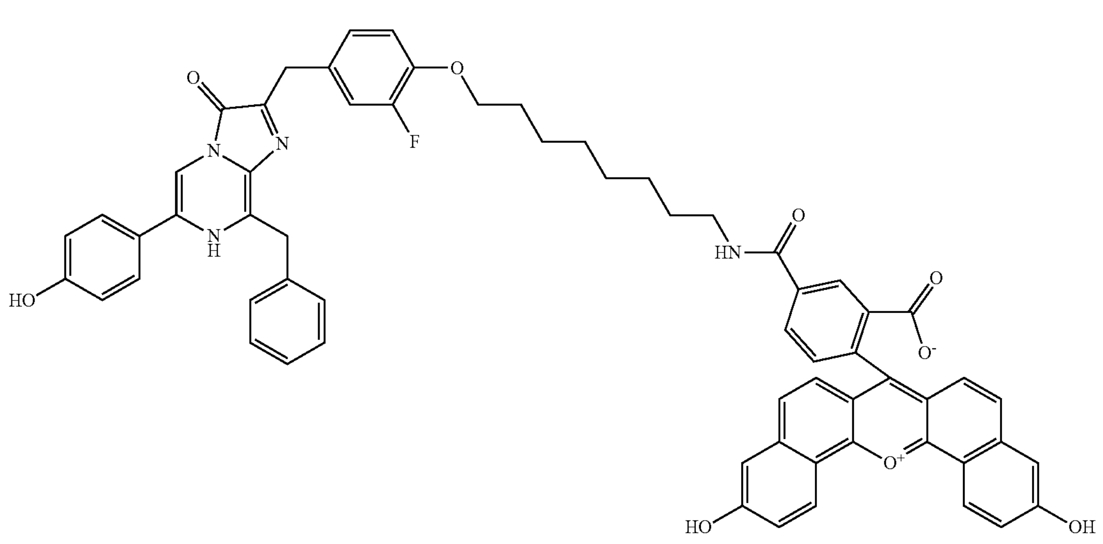 [SMILES: O=C(NCCCCCCCCOc1ccc(Cc2nc3c(Cc4ccccc4)[nH]c(-c4ccc(O)cc4)cn-3c2=O)cc1F)c1ccc(-c2c3ccc4cc(O)ccc4c3[o+]c3c2ccc2cc(O)ccc23)c(C(=O)[O-])c1]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (25 mg, 0.044 mmol) was reacted with 2,5-dioxopyrrolidin-1-yl 3,11-dihydroxy-3'-oxo-3'H-spiro[dibenzo[c,h]xanthene-7,1'-isobenzofuran]-5'-carboxylate (25 mg, 0.044 mmol) to afford the desired product (13 mg, 28%) as a brown solid. ESI MS m/z 1028 $[M+H]^+$; HPLC 82.3% (AUC), $T_R$ 5.71 min; UV (MeOH) λ 528 nm, ε 11,800.

Example 22

N1-(8-(4-((8-benzyl-6-(4-hydroxyphenyl)-3-oxo-3,7-dihydroimidazo[1,2-a]pyrazin-2-yl)methyl)-2-fluorophenoxy)octyl)-N4-(2-(5,5-difluoro-1,3-dimethyl-5H-5$\lambda^4$,6$\lambda^4$-dipyrrolo[1,2-c:2',1'-f][1,3,2]diazaborinin-10-yl)ethyl)succinamide (JRW-1088)

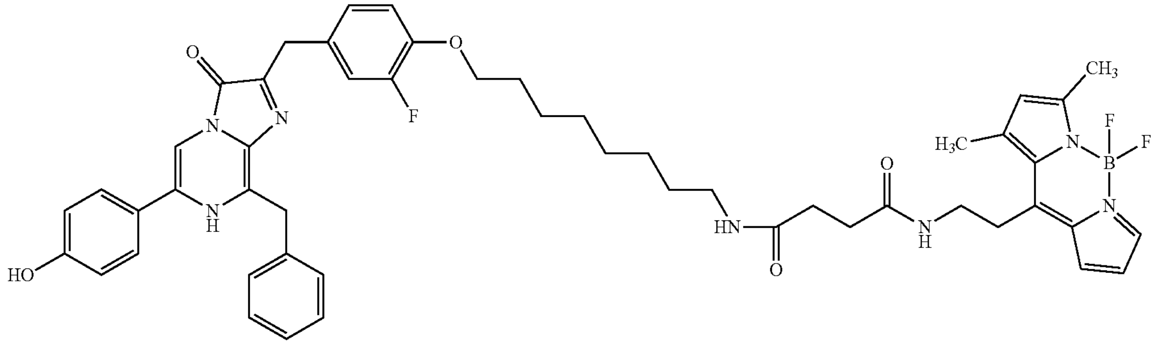

Following general procedure G, 2-(4-((8-aminooctyl)oxy)-3-fluorobenzyl)-8-benzyl-6-(4-hydroxyphenyl)imidazo[1,2-a]pyrazin-3(7H)-one (30 mg, 0.052 mmol) was reacted with 2,5-dioxopyrrolidin-1-yl 4-((2-(5,5-difluoro-1,3-dimethyl-5H-5$\lambda^4$,6$\lambda^4$-dipyrrolo[1,2-c:2',1'-f][1,3,2]diazaborinin-10-yl)ethyl)amino)-4-oxobutanoate (48 mg, 0.10 mmol) to afford the desired product (16 mg, 33%) as a brown solid. ESI MS m/z 914 $[M+H]^+$; HPLC 75.6% (AUC), $T_R$ 5.63 min; UV (MeOH) λ 490 nm, ε 48,754.

Example 23

Luminescent Properties

Luminescence Assay Procedure: Each compound to be screened was dissolved in DMSO (5 mM) and then further diluted to 100 μM in NANO-GLO® Luciferase Assay Buffer. Km values were determined by first serially diluting substrates two-fold into NANO-GLO® Luciferase Assay Buffer. Substrate dilutions were then combined with an equal volume of NanoLuc diluted to 4 ng/ml in TBS+0.01% BSA. Autoluminescence was measured by combining the 100 uM dilution of substrate with TBS+0.01% BSA. Luminescence and autoluminescence values were measured in a GloMax®-Multi+ luminometer three minutes after substrate addition. Signal decay was measured by combining equal volumes of 100 uM of substrate with 4 ng/ml NanoLuc in TBS+0.01% BSA and then samples were read in five minute intervals for two hours using a GloMax®-Multi+. Luminescence and autoluminescence values at 100 uM are shown in FIG. 1. Km was calculated using GraphPad Prism using nonlinear Michaelis-Menten regression. Signal half-life values were calculated using GraphPad Prism Non-linear decay, plateau set to zero. Light output, signal half-life, and Km values are summarized in Table 1. Values are represented as relative values where Furimazine is set to 1 in each category (~$2.0\times10^7$ RLU at 2 ng/mL NanoLuc).

TABLE 1

| Compound | RLU (at 100 μM) | Signal half life | Km |
|---|---|---|---|
| Furimazine | 1 | 1 | 1 |
| Furimazine-h | 1 | 0.04 | NT |
| JRW-0855 | 0.004 | 1.2 | 10 |
| JRW-0857 | 0.00000029 | 0.8 | NC |
| JRW-0892-2 | 0.04 | 0.3 | 1.4 |
| JRW-0893 | 0.05 | 2.2 | 5.7 |
| JRW-0900 | 0.00094 | 3.1 | 2.2 |
| JRW-0905 | NT | NT | NT |
| JRW-0906 | 0.036 | 2.6 | 16 |
| JRW-0912 | 0.000061 | NC | NC |
| JRW-0925 | 0.02 | 0.12 | 2.3 |
| JRW-0926 | 0.04 | 1.2 | 17 |
| JRW-0927 | 0.0000024 | NC | NC |
| JRW-0972 | 0.00005 | NC | 2.2 |
| JRW-0975 | 0.005 | NC | 4.8 |
| JRW-0986 | 0.00005 | NC | 4.3 |
| JRW-0995 | 0.009 | NC | 2.3 |
| JRW-1018 | NT | NT | NT |
| JRW-1022 | NT | NT | NT |
| JRW-1023 | NT | NT | NT |
| JRW-1058 | NT | NT | NT |
| JRW-1059 | NT | NT | NT |
| JRW-1088 | NT | NT | NT |
| JRW-1549 | NT | NT | NT |
| JRW-1566 | NT | NT | NT |

NT—not tested
NC—not calculable

Figure 2:
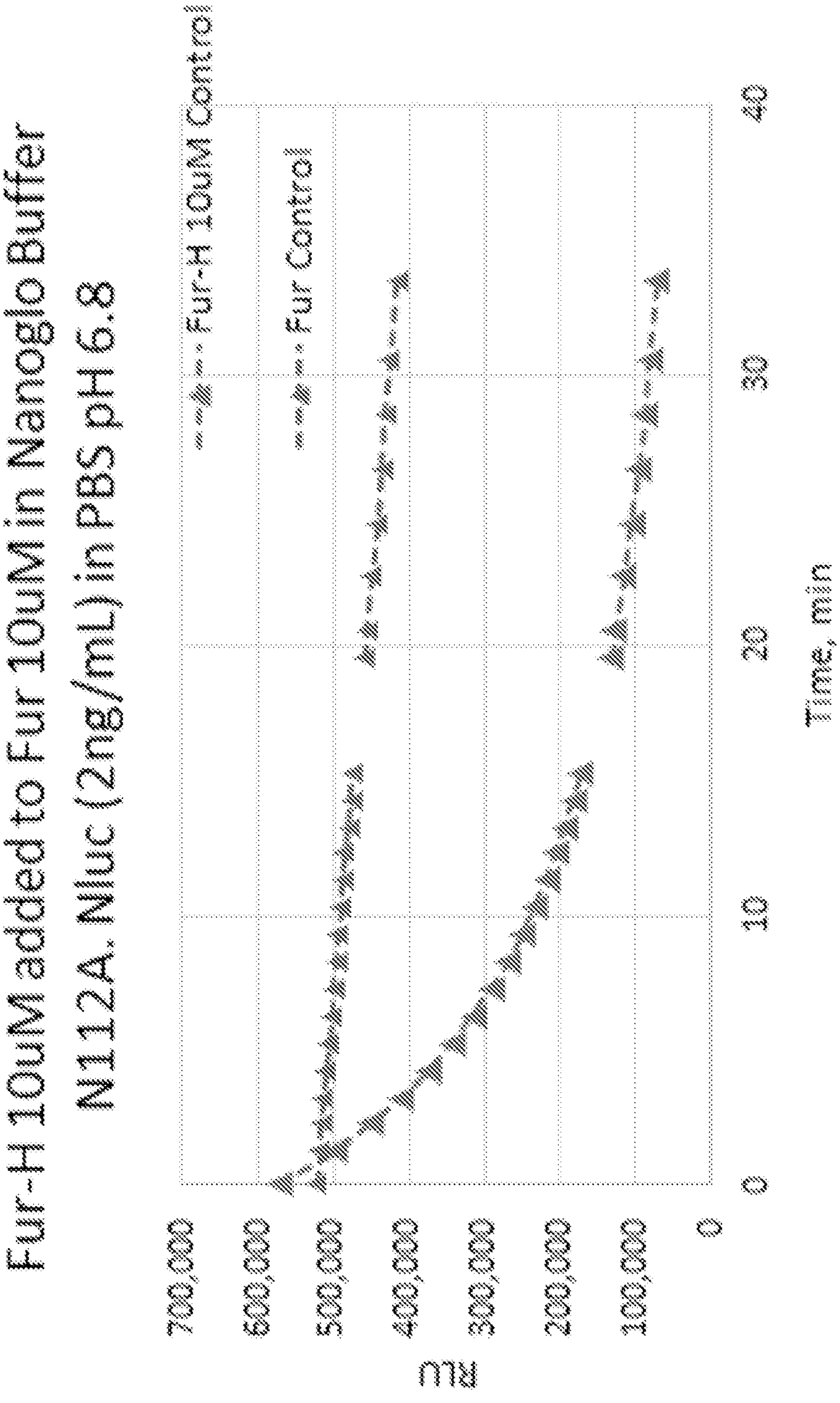
FIG. 2 shows kinetic reads of furimazine and furimazine-h in NanoGlo® buffer at 10 μM with 2 ng/mL NanoLuc® luciferase (Nluc).
Figure 4A:
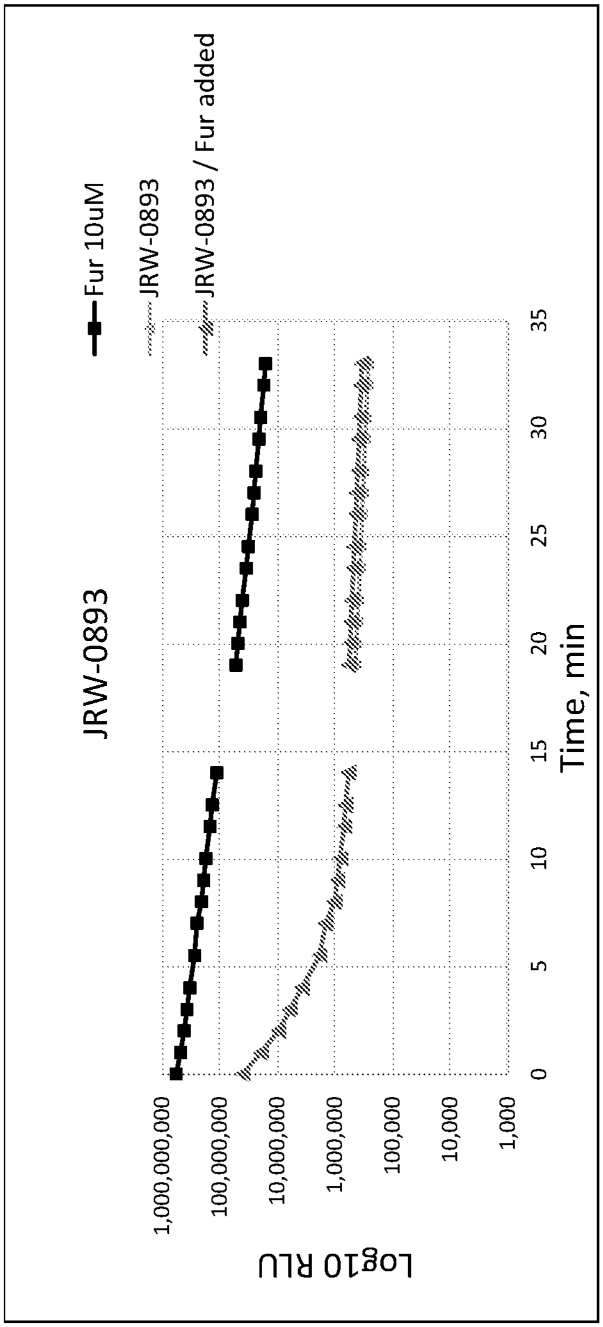
FIGS. 4A-F show NanoLuc® luciferase (Nluc) inhibitory activity of exemplary compounds in comparison to furimazine.
Figure 4B:
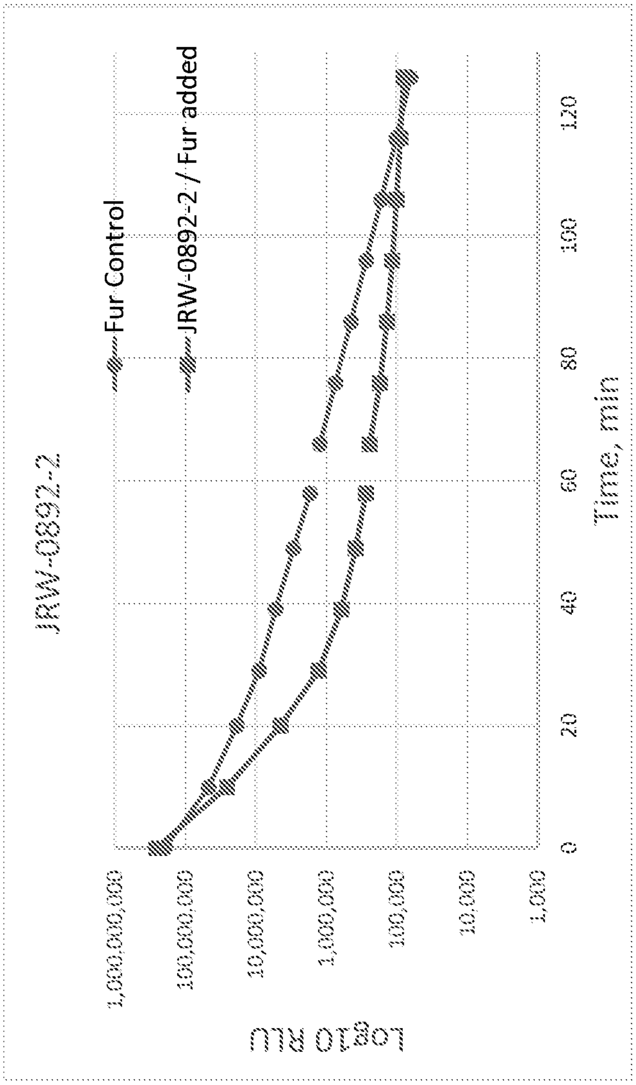
Figure 4C:
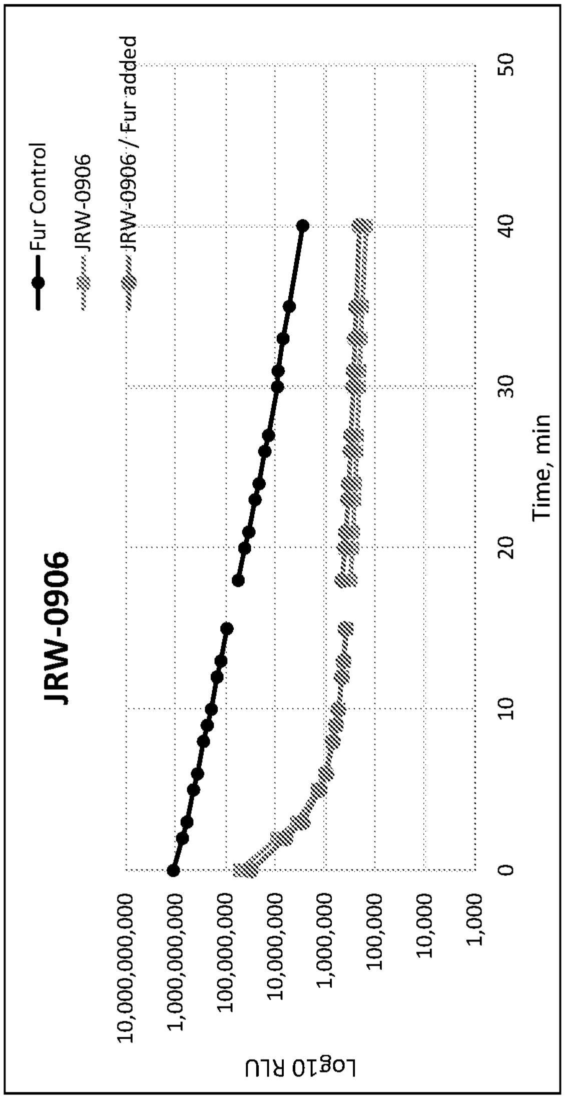
Figure 4D:
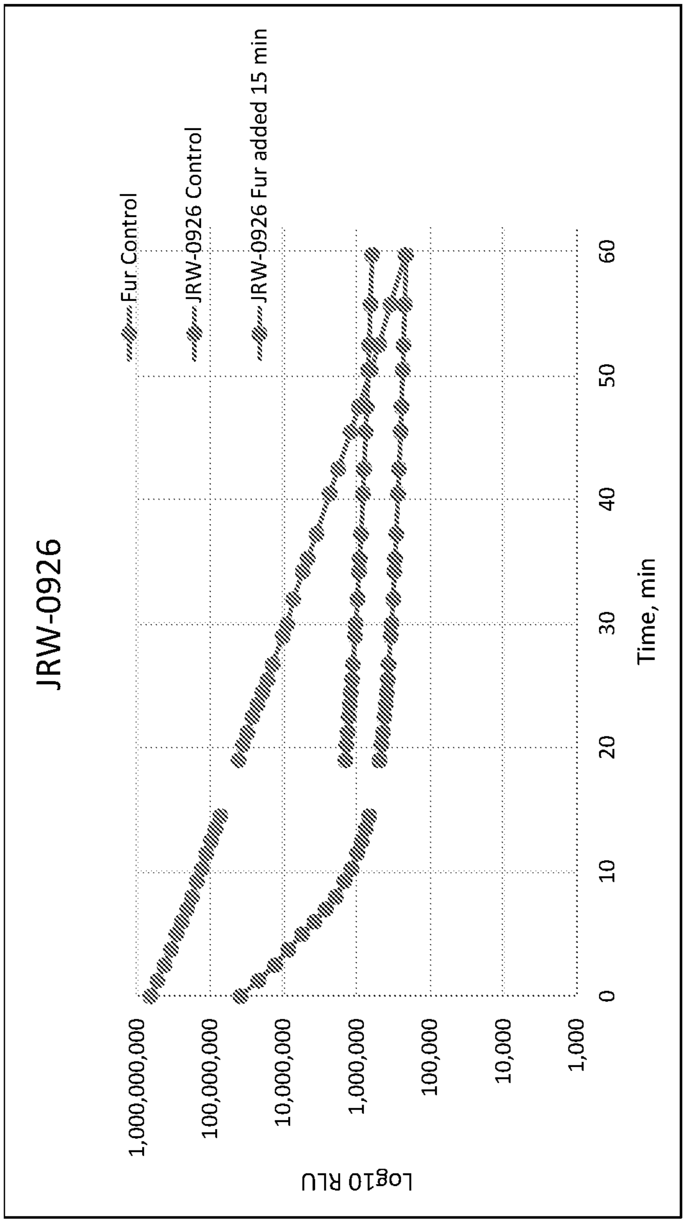
Figure 4E:
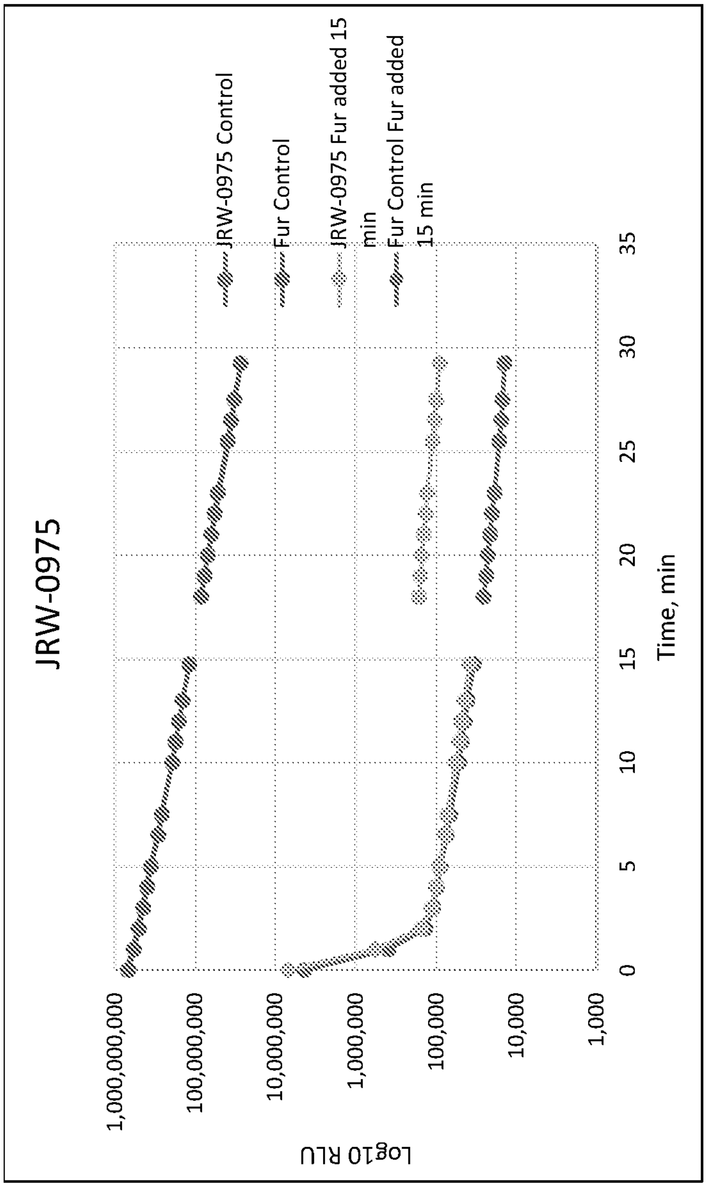
Figure 4F:
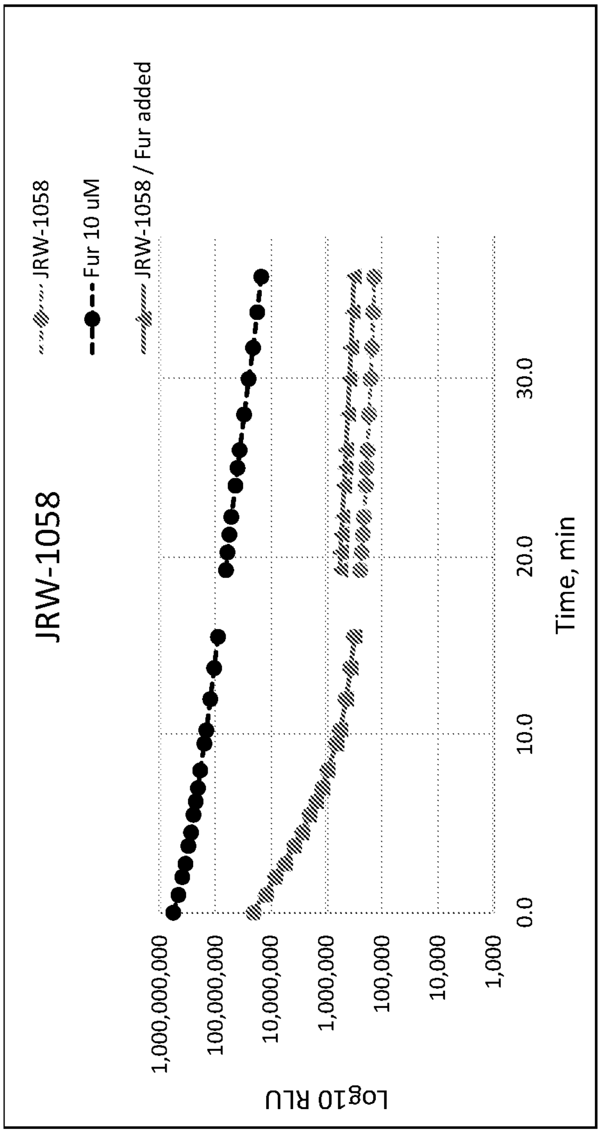

Kinetic Read Procedure: Furimazine (8-benzyl-2-(furan-2-ylmethyl)-6-phenylimidazo[1,2-a]pyrazin-3 (7H)-one) or furimazine-h (8-benzyl-2-(furan-2-ylmethyl)-6-(4-hydroxyphenyl)imidazo[1,2-a]pyrazin-3(7H)-one) was dissolved in Ethanol:propylene glycol (85:15) (5 mM) and then further diluted to various concentrations in NANO-GLO® Luciferase Assay Buffer. Each diluted substrate was then combined in equal volumes with purified NANOLUC® Luciferase diluted into phosphate buffered saline at pH 6.8. Light output for each substrate was measured in a GloMax®-Multi+ luminometer over various lengths of time. The kinetic read of signal half-life for furimazine and furimazine-h is shown in FIG. 2.

Example 24

Inhibition of NanoLuc® Luciferase (Nluc)

Compounds were also tested for their ability to block furimazine luminescence with NanoLuc. Typically, NanoLuc (0.4 μg/mL) in DMEM was incubated with either furimazine or test compound (50 μM) while monitoring RLU's with a GloMax® luminometer for 10-60 minutes. After the set time, the plate was removed from the instrument, and a dose of furimazine (10 μM) was added to the well containing the test compound and monitored for 10-60 minutes.

Suicide Inhibition: FIGS. 3A-B depicts inhibition of Nluc luciferase by furimazine-h. Furimazine-h (10 μM) was incubated with NanoLuc in NanoGlo or DMEM for 15 or 10 minutes, respectively. This bright signal rapidly degrades to a fraction of the signal observed in the furimazine positive control wells. Following the incubation period, various concentrations of furimazine was added to the well containing furimazine-h and these additions of furimazine results in no increase in bioluminescence, indicating that NanoLuc is inhibited.

Other examples of exemplary Nluc suicide substrates are shown in FIG. 4A-F. Taken together, these results demonstrate that furimazine-h, JRW-0893, JRW-0892-2, JRW-0906, JRW-0926, JRW-0975, and JRW-1058 are exemplary suicide substrates of NanoLuc.

Figure 9:
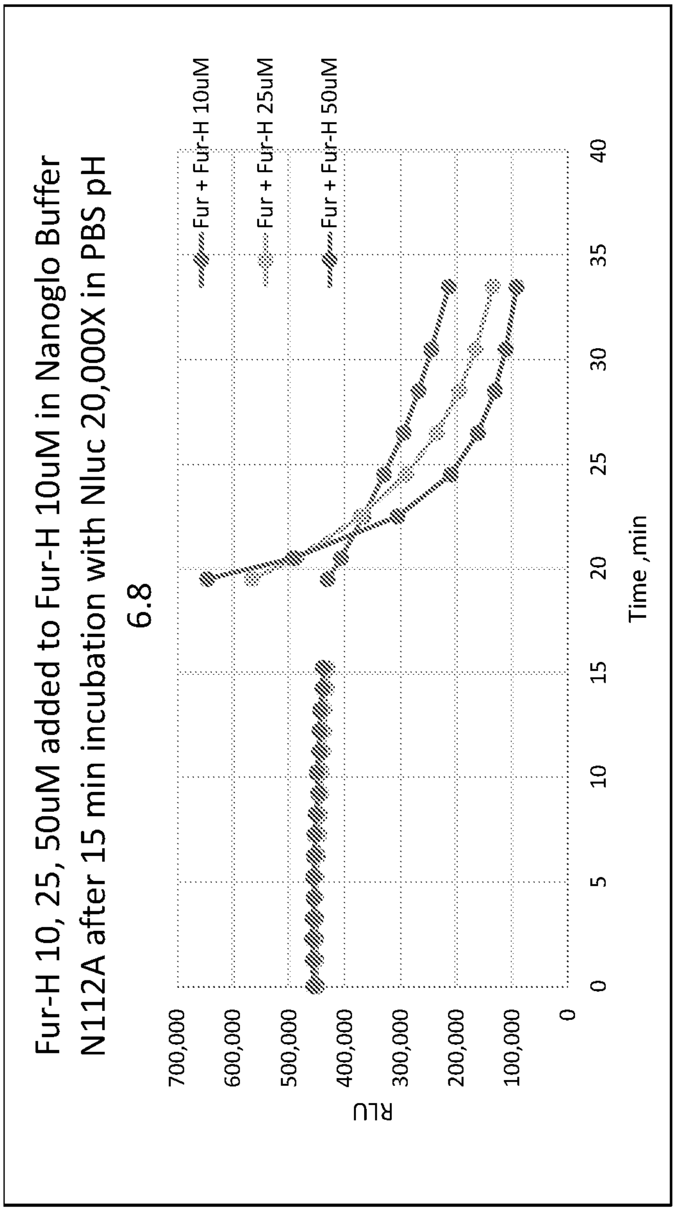
FIG. 9 shows Nluc inhibitory activity of furimazine-h even after first exposing NanoLuc® luciferase (Nluc) to furimazine.

FIG. 9 depicts inhibition of Nluc luciferase by furimazine-h. This is a reverse addition experiment as compared to FIG. 3. Furimazine (10 μM) was incubated with NanoLuc in NanoGlo® buffer for 15 minutes. Following the incubation period, various concentrations of furimazine-h was added to the well containing furimazine and these additions of furimazine-h results in a rapid signal decay. This indicates that furimazine-h can compete out furimazine from Nluc and upon undergoing the bioluminescent reaction, Nluc is inhibited by the suicide substrate.

Figure 5A:
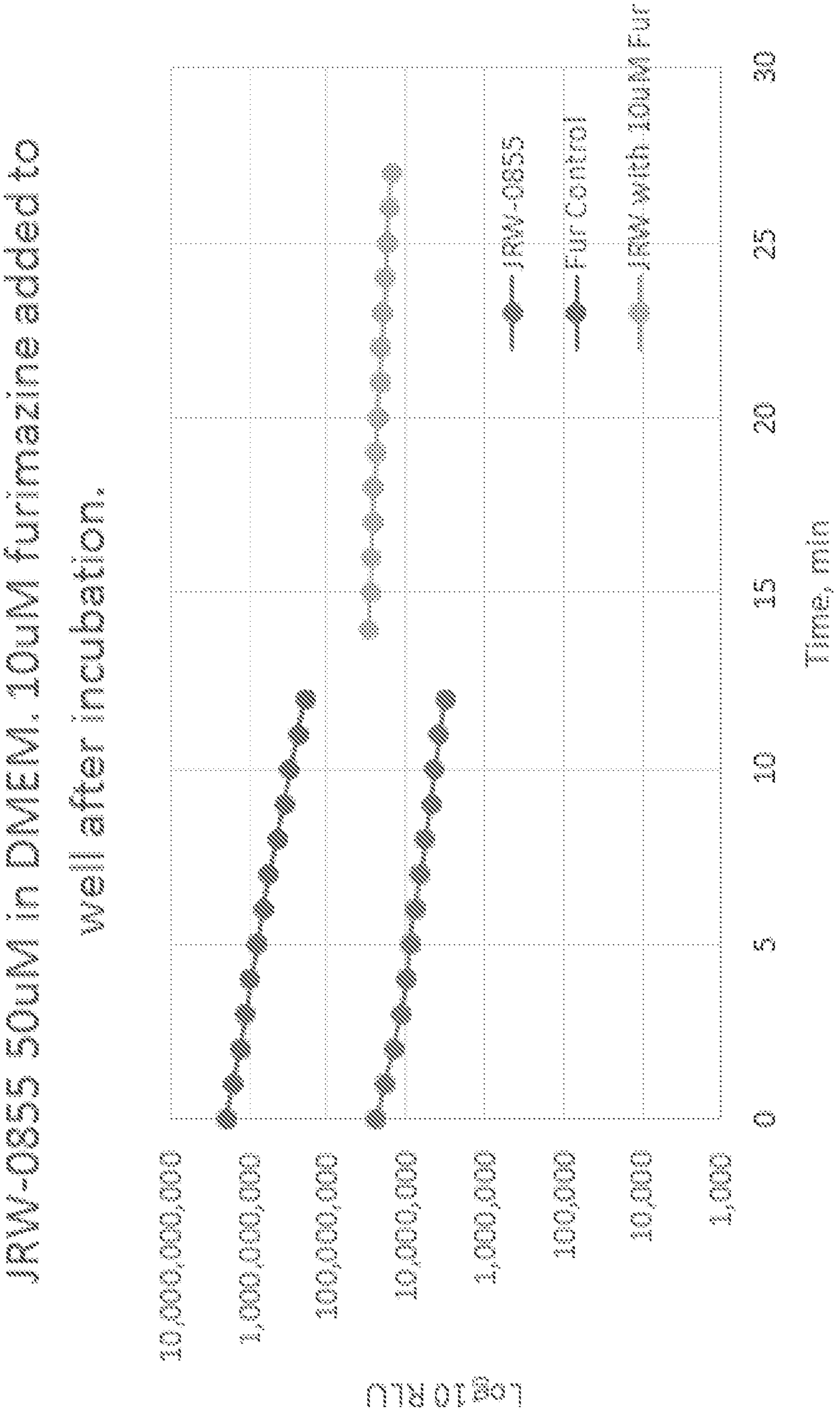
FIGS. 5A-B show partial NanoLuc® luciferase (Nluc) inhibitory activity of JRW-0855 and JRW-1088.
Figure 5B:
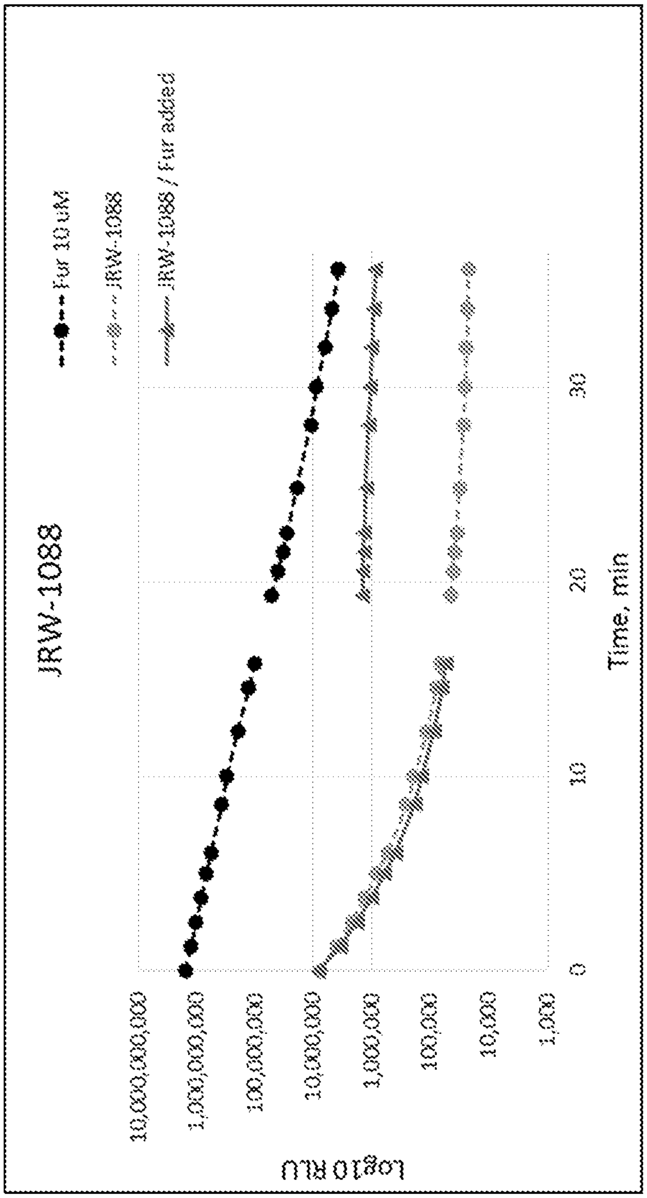

Partial Inhibition: Tested compounds that were fairly poor substrates for Nluc showed only partial inhibition of bioluminescence upon furimazine addition. These partial inhibitors typically showed less than about 1% of the bioluminescent activity of furimazine when incubated with NanoLuc. FIG. 5A-B shows the partial inhibitory activity of JRW-0855 and JRW-1088. JRW-0855 and JRW-1088 were incubated with NanoLuc in DMEM for 12 minutes. As shown in the figure, the initial luminescent signal for the reaction of JRW-0855 and JRW-1088 with NanoLuc was significantly lower than the initial luminescent signal for the reaction of furimazine with NanoLuc. After the incubation period, 10 μM furimazine was added to the well. The addition of furimazine resulted in a partial recovery of bioluminescence, indicating that Nluc is only partially inhibited by JRW-0855 and JRW-1088. Other exemplary partial Nluc inhibitors included JRW-0904, JRW-0925, and JRW-0995, JRW-1018, and JRW-1022.

Figure 6A:
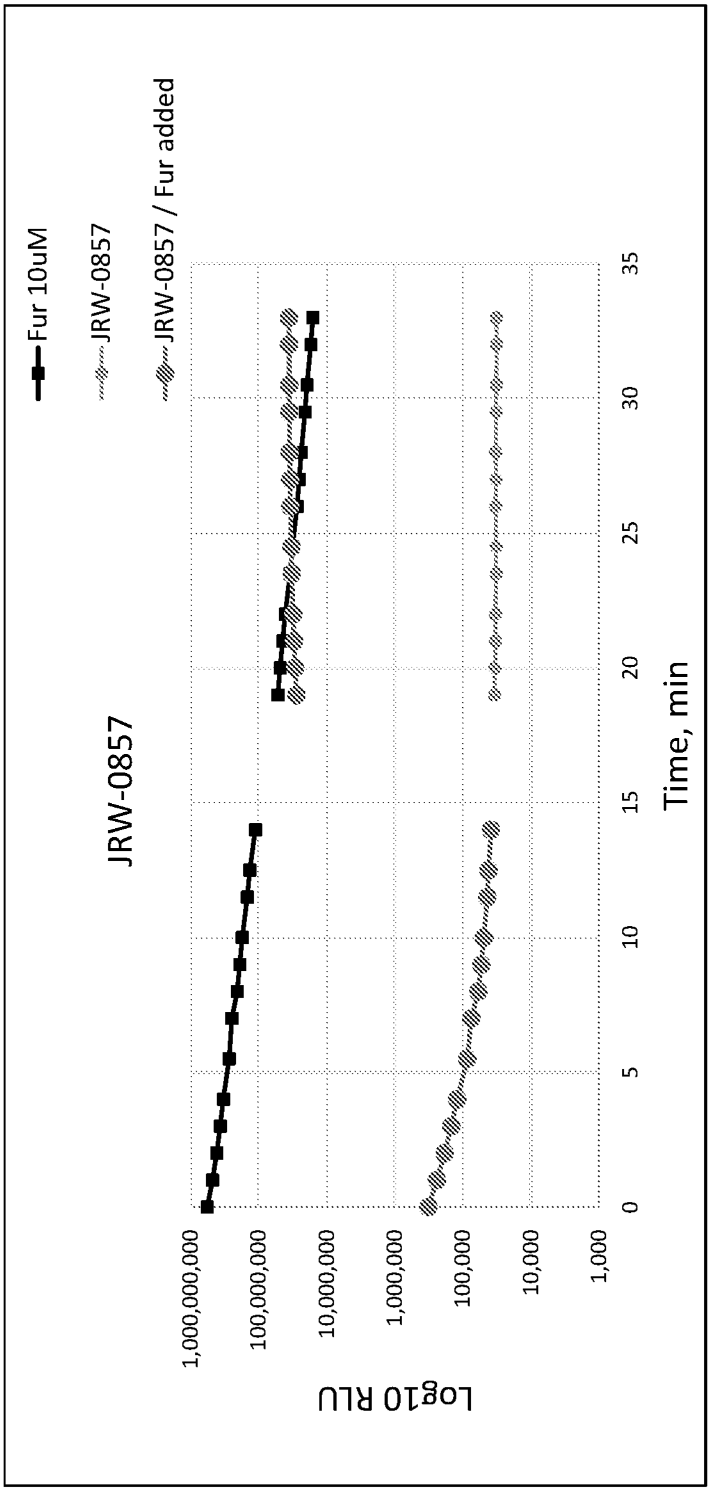
FIGS. 6A-B show that JRW-0857 and JRW-1059 do not inhibit NanoLuc® luciferase (Nluc).
Figure 6B:
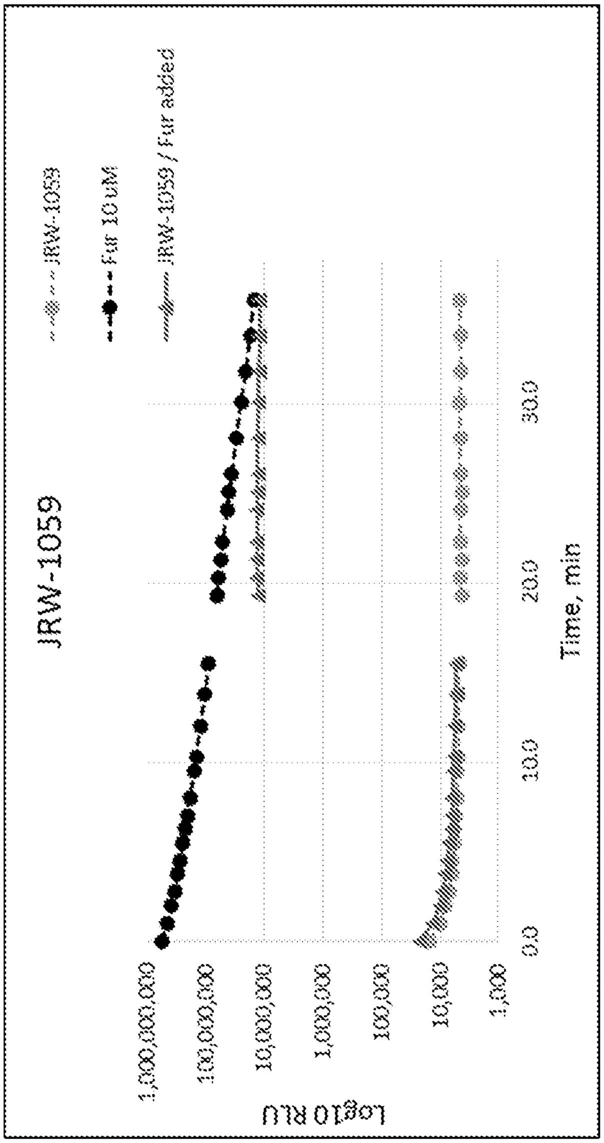

Lack of inhibition: Tested compounds that were not substrates of NanoLuc showed no inhibition of bioluminescence upon furimazine addition. FIG. 6A-B shows the failure of JRW-0857 and JRW-1059 to inhibit NanoLuc. The addition of furimazine resulted in a large increase in bioluminescence, indicating that NanoLuc is not inhibited. Examples of tested compounds that did not inhibit NanoLuc include JRW-0857, JRW-0900, JRW-0912, JRW-0927, JRW-0972, JRW-0986, and JRW-1023.

Taken together, the results of these studies suggest that the inhibition of NanoLuc is a product of the initial bioluminescence reaction produced when the disclosed compounds are incubated with NanoLuc. As such, compounds with inhibitory activity were termed suicide substrates. Further studies are required to understand the mechanism of action for these substrates.

Example 25

Inhibition of NanoBiT™ Binary Luciferase System

Figure 7:
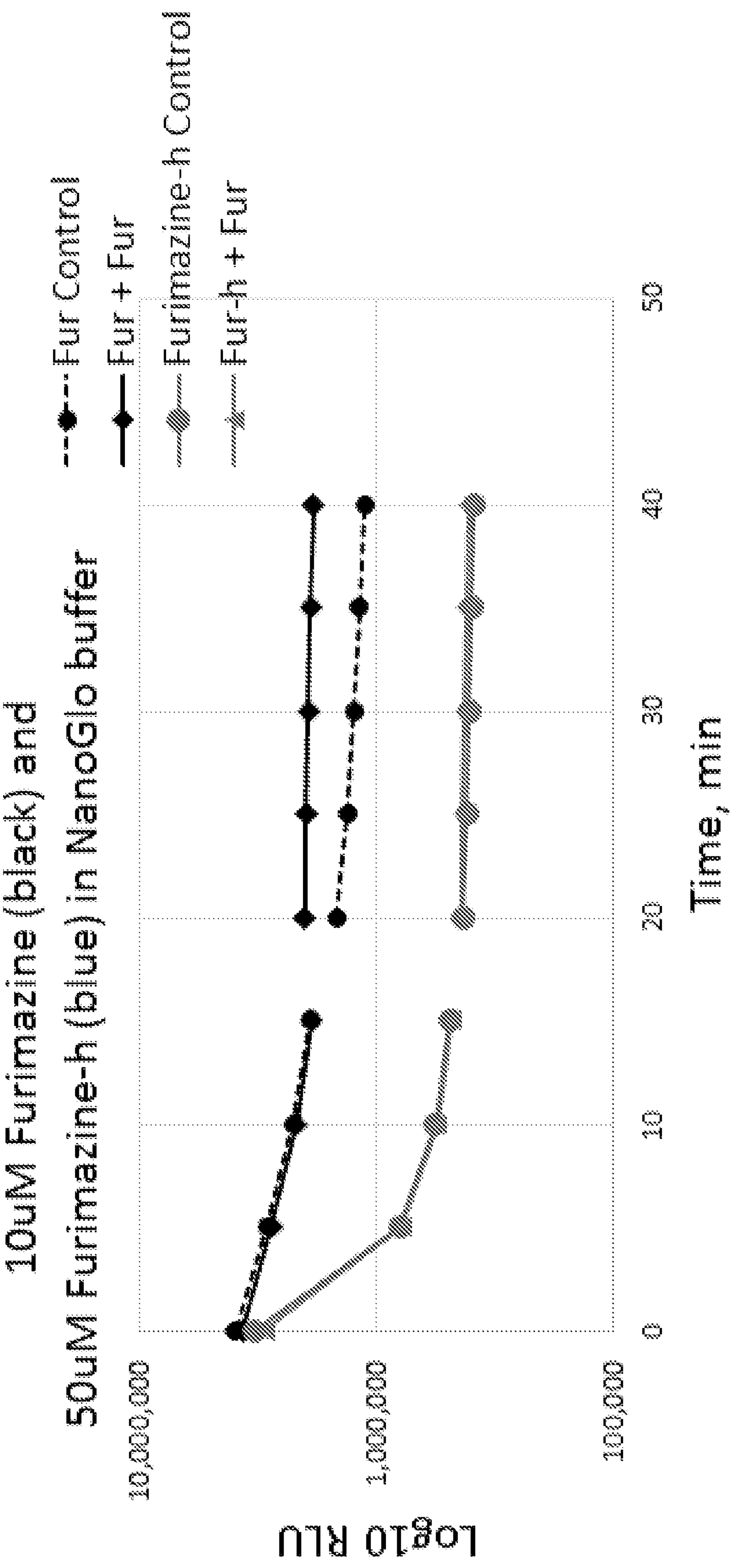
FIG. 7 shows inhibition of the NanoBiT™ Binary luciferase by furimazine-h.

Compounds were also tested for their ability to inhibit the NanoBiT™ Binary luciferase. HiBiT (SEQ ID NO: 3) and LgBiT (SEQ ID NO: 4) (two subunits of the NanoBiT™ luciferase) were incubated with furimazine or furimazine-h for 15 minutes. Following the incubation period, 10 μM furimazine was added. As shown in FIG. 7, the furimazine-h initially produces a luminescent signal comparable to that of furimazine following incubation with Nluc. This signal rapidly degrades to a fraction of the signal observed in the furimazine positive control wells. Addition of furimazine to the furimazine positive control wells results in an increase in bioluminescence. In comparison, addition of furimazine to the furimazine-h wells results in no increase in bioluminescence indicating that the NanoBiT™ luciferase is effectively inhibited by furimazine-h.

Example 26

Example 27 Fluorescence Imaging

To further demonstrate the labeling of the suicide substrates to NanoLuc, NanoLuc was incubated with two of the fluorescent FAM-coelenterazine substrates, JRW-0906 and JRW-0926. The efficiency of the NanoLuc suicide substrates was compared with a chloroalkane-FAM substrate with a fusion protein in which the HaloTag protein (SEQ ID NO: 5) is fused to either glutathione transferase (GST) or NanoLuc.

Figure 8:
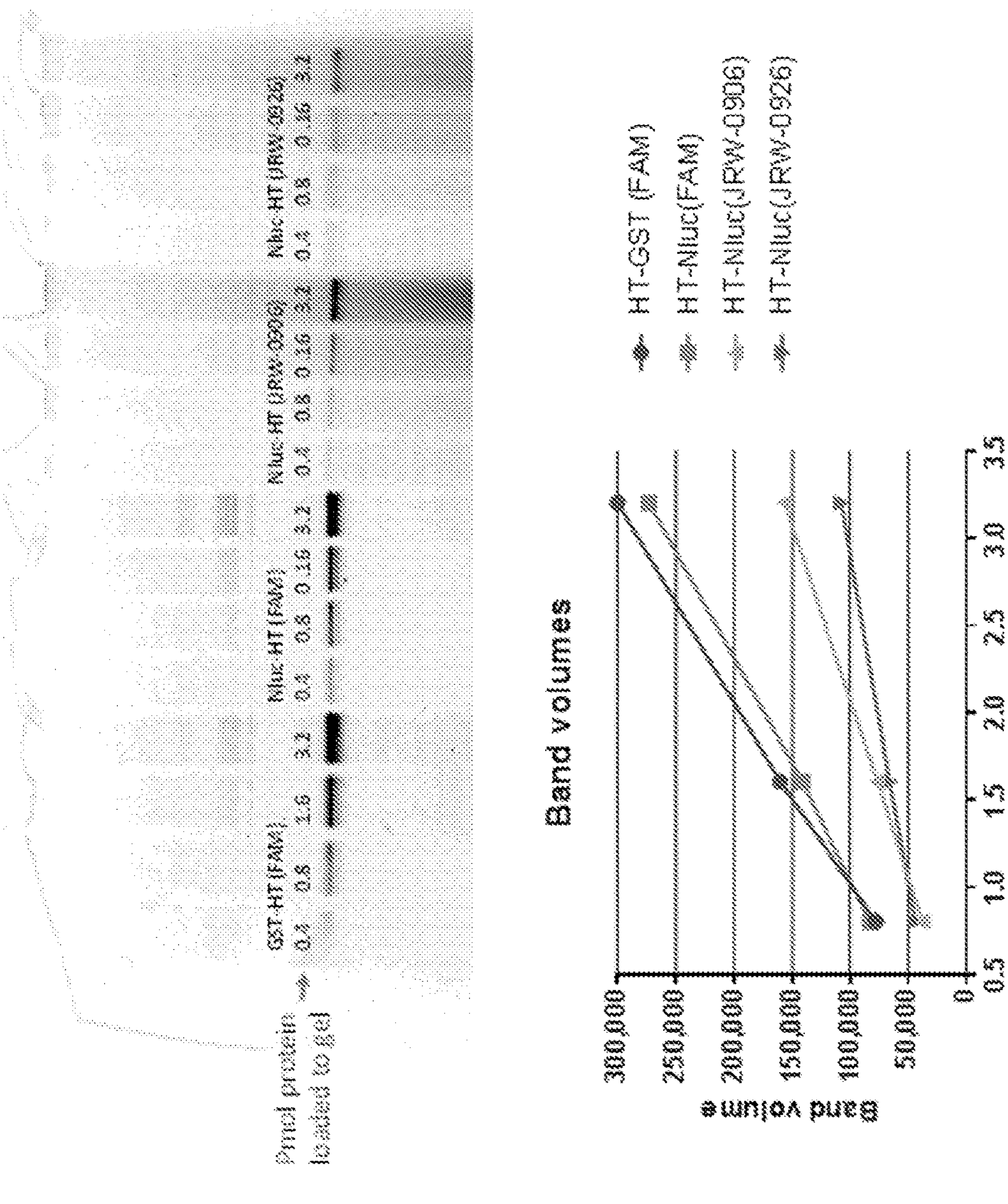
FIGS. 8A-B show fluorescent labeling of NanoLuc® luciferase (Nluc) with two of the fluorescent FAM-coelenterazine substrates, JRW-0906 and JRW-0926. The efficiency of labeling was compared to that of a chloroalkane-FAM substrate with a HaloTag® fusion to either glutathione transferase (GST) or NanoLuc® luciferase (Nluc).

Either FAM chloroalkane or coelenterazine FAM substrate was incubated with glutathione transferase-HaloTag (GST-HT) or NanoLuc-HaloTag (Nluc-HT) fusions. The reactions were with 0.5 μM protein (GST-HT or Nluc-HT) and 50 μM of label (100× excess of label) and incubated for 30 minutes at room temperature. The sample titrations of each sample were then loaded to the SDS/PAGE gel. The fluorescence (473ex) (Cy2 filter set) was read and quantified. As shown in FIG. 8A, both chloroalkane and coelenterazine substrates show dose dependent labeling. Results are quantified in FIG. 8B. As shown in FIG. 8B, the FAM appended suicide substrate (JRW-0906) can label NanoLuc with ~50% efficiency as the chloroalkane-HT system.

Example 27

3-(2-(2-azidoethoxy)ethoxy)-N-(2-(2-((6-chlorohexyl)oxy)ethoxy)ethyl)propanamide (JRW-1505)

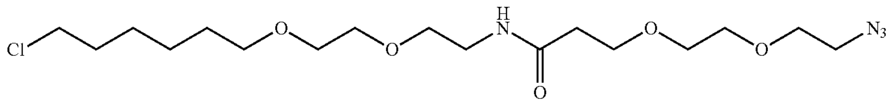 [SMILES: [N-]=[N+]=NCCOCCOCCC(=O)NCCOCCOCCCCCCCl]

To a solution of 2-(2-((6-chlorohexyl)oxy)ethoxy)ethan-1-amine (60 mg, 0.27 mmol) and 2,5-dioxopyrrolidin-1-yl 3-(2-(2-azidoethoxy)ethoxy)propanoate (80 mg, 0.27 mmol) in DMF (5 mL), trimethylamine (54 mg, 0.54 mmol) was added. The reaction was stirred at RT for 3 h. The reaction was diluted with ethyl acetate, and the organic layer was washed with water. The organic layer was dried with sodium sulfate, filtered, concentrated, and chromatographed to afford desired product (38 mg, 34%) as a colorless oil. ESI MS m/z 409 $[M+H]^+$.

Example 28

(2-(2-((6-chlorohexyl)oxy)ethoxy)ethyl)succinamide-DBCO (JRW-1550)

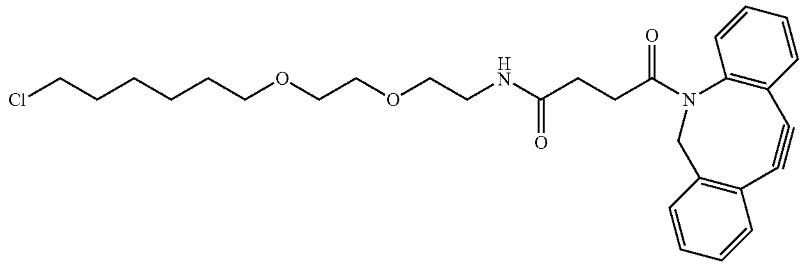 [SMILES: O=C(CCC(=O)N1Cc2ccccc2C#Cc2ccccc21)NCCOCCOCCCCCCCl]

To a solution of 2-(2-((6-chlorohexyl)oxy)ethoxy)ethan-1-amine (20 mg, 0.090 mmol) and 2,5-dioxopyrrolidin-1-yl 4-DBCO-amino-4-oxobutanoate (36 mg, 0.090 mmol) in DMF (5 mL), trimethylamine (18 mg, 0.18 mmol) was added. The reaction was stirred at RT for 4 h. The reaction was diluted with ethyl acetate, and the organic layer was washed with water. The organic layer was dried with sodium sulfate, filtered, concentrated, and chromatographed to afford desired product (37 mg, 80%) as a light brown oil. ESI MS m/z 512 $[M+H]^+$.

Example 29

$N^1$-(8-(4-((8-benzyl-6-(4-hydroxyphenyl)-3-oxo-3,7-dihydroimidazo[1,2-a]pyrazin-2-yl)methyl)-2-fluorophenoxy)octyl)-$N^4$-DBCO-succinamide (JRW-1549)

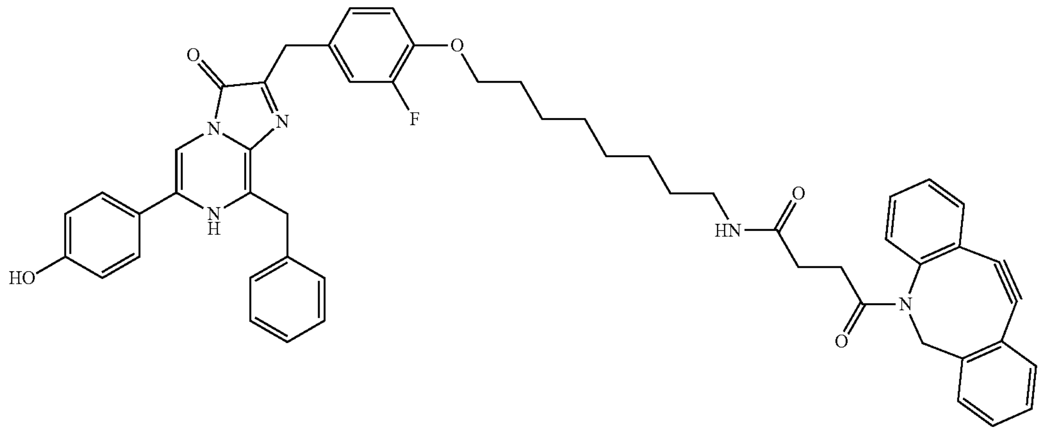 [SMILES: O=C(CCC(=O)N1Cc2ccccc2C#Cc2ccccc21)NCCCCCCCCOc1ccc(Cc2nc3c(Cc4ccccc4)[nH]c(-c4ccc(O)cc4)cn-3c2=O)cc1F]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (25 mg, 0.044 mmol) was reacted with 2,5-dioxopyrrolidin-1-yl 4-DBCO-amino-4-oxobutanoate (21 mg, 0.053 mmol) to afford the desired product (23 mg, 62%) as an orange solid. ESI MS m/z 857 $[M+H]^+$.

Example 30

(E)-cyclooct-4-en-1-yl (2-(2-((6-chlorohexyl)oxy)ethoxy)ethyl)carbamate (JRW-1567)

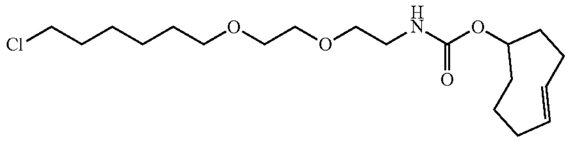 [SMILES: O=C(NCCOCCOCCCCCCCl)OC1CC/C=C/CCC1]

To a solution of 2-(2-((6-chlorohexyl)oxy)ethoxy)ethan-1-amine (20 mg, 0.090 mmol) and (E)-cyclooct-4-en-1-yl (2,5-dioxopyrrolidin-1-yl) carbonate (24 mg, 0.090 mmol) in DCM (5 mL), trimethylamine (18 mg, 0.18 mmol) was added. The reaction was stirred at rt for 3 h. The reaction was diluted with DCM, and Celite was added. The mixture was concentrated and chromatographed to afford desired product (27 mg, 81%) as a colorless oil. ESI MS m/z 376 $[M+H]^+$.

Example 31

(E)-cyclooct-4-en-1-yl (8-(4-((8-benzyl-6-(4-hydroxyphenyl)-3-oxo-3,7-dihydroimidazo[1,2-a]pyrazin-2-yl)methyl)-2-fluorophenoxy)octyl)carbamate (JRW-1566)

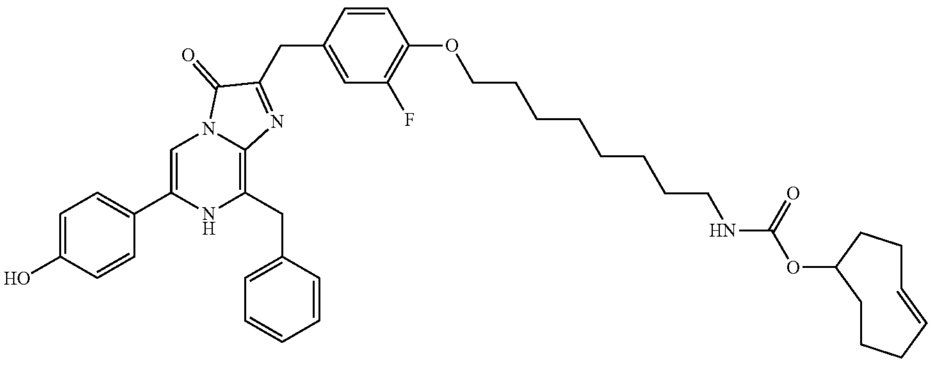 [SMILES: O=C(NCCCCCCCCOc1ccc(Cc2nc3c(Cc4ccccc4)[nH]c(-c4ccc(O)cc4)cn-3c2=O)cc1F)OC1CC/C=C/CCC1]

Following general procedure G, 2-(4-((8-aminooctyl)oxy)-3-fluorobenzyl)-8-benzyl-6-(4-hydroxyphenyl)imidazo[1,2-a]pyrazin-3(7H)-one (25 mg, 0.044 mmol) was reacted with (E)-cyclooct-4-en-1-yl (2,5-dioxopyrrolidin-1-yl) carbonate (14 mg, 0.053 mmol) to afford the desired product (13 mg, 40%) as an orange solid. ESI MS m/z 721 $[M+H]^+$.

Example 32

2-(6-hydroxy-3-oxo-3H-xanthen-9-yl)-4-((3-(4-(6-methyl-1,2,4,5-tetrazin-3-yl)phenoxy)propyl)carbamoyl)benzoic acid (JRW-1577)

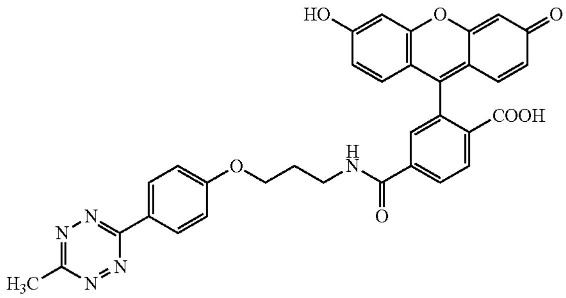 [SMILES: Cc1nnc(-c2ccc(OCCCNC(=O)c3ccc(C(=O)O)c(-c4c5ccc(=O)cc-5oc5cc(O)ccc45)c3)cc2)nn1]

To a solution of 3-(4-(6-methyl-1,2,4,5-tetrazin-3-yl)phenoxy)propan-1-amine hydrochloride (25 mg, 0.089 mmol) and 4-(((2,5-dioxopyrrolidin-1-yl)oxy)carbonyl)-2-(6-hydroxy-3-oxo-3H-xanthen-9-yl)benzoic acid (31 mg, 0.066 mmol) in DMF (5 mL), diisopropylethylamine (34 mg, 0.27 mmol) was added. The reaction was stirred at RT for 2 h. The reaction was diluted with ethyl acetate, and the organic layer was washed with a solution of $NH_4Cl$. The organic layer was dried with sodium sulfate, filtered, concentrated, and chromatographed to afford desired product (16 mg, 30%) as a red solid. ESI MS m/z 604 $[M+H]^+$.

Example 33

Comparison of Direct Labeling and Two-Step Labeling with an Azide-DBCO Pair by Fluorescence Imaging In Example 26, a dye-appended suicide substrate is shown by fluorescence imaging to label NanoLuc. In this example, a suicide substrate with an appended azide is shown to label a NanoLuc-HaloTag protein in a two-step procedure in which the second step is copper-free click chemistry with a DBCO appended FAM dye. This example compared five methods: direct labeling of NanoLuc with JRW-0926; the two-step labeling of NanoLuc between JRW-0975 and a DBCO-FAM; the two-step labeling of NanoLuc between JRW-1022 and a DBCO-FAM; direct labeling of HaloTag with a FAM-HT ligand; and two-step labeling with an SE appended with an azide. Structures of the compounds used in this example are illustrated in FIG. 10A.

0.5 uM NanoLuc-HaloTag in 100 mM Tris pH 8.0 was incubated for 1 hour with 50 uM of: Tube 1—JRW-1505; Tube 2—FAM-HaloTag ligand; Tube 3—JRW-0926; Tube 4—JRW-0975; Tube 5—JRW-1022; and Tube 6—SE-azide. In the second step, 100 uM DBCO-FAM was incubated for 4 hours in Tubes 1, 4, 5, and 6, followed by SDS/PAGE gel for all samples (FIG. 10B). The fluorescence (473ex) (Cy2 filter set) of bands corresponding to the size of NanoLuc-HaloTag was read and quantified.

Tube 1 shows two-step labeling occurs between HaloTag ligand-Azide and DBCO-FAM. Tube 2 and 3 shows direct labeling of HaloTag or NanoLuc with the chloroalkane or the suicide substrate. Tube 4 and 5 shows two-step labeling occurs with azide appended suicide substrates. Tube 6 shows two-step labeling available lysines on the protein.

In a second experiment, 1.5 uM NanoLuc-HaloTag in 100 mM Tris (or DPBS buffer) pH 8.0 was incubated with 50 uM of JRW-0975, FAM-HaloTag ligand, JRW-0926, JRW-1022, or SE-azide for 1 hour. In the second step, 100 uM DBCO-FAM was incubated for 4 hours with tubes 3, 4, and 5, followed by SDS/PAGE gel (FIG. 11A). The fluorescence (473ex) (Cy2 filter set) of bands corresponding to the size of NanoLuc-HaloTag was read and quantified (FIG. 11B).

The data from both experiments demonstrates two step labeling with azide appended ligands and a DBCO-FAM. However, direct labeling appears more efficient with this configuration.

Example 34

Comparison of Direct Labeling and Two-Step Labeling with TCO-Tetrazine Pair by Fluorescence Imaging Similar to the previous example, NanoLuc-HaloTag protein was incubated with compounds to either directly label or label via the two-step process with FAM. Structures of additional compounds used in this example are shown in FIG. 12A. Compounds were incubated with the NanoLuc-HaloTag fusion protein and analyzed by florescence imaging on SDS/PAGE gel.

Tube 1.1 shows two-step labeling occurs between DBCO-HaloTag ligand (JRW-1550) and Azide-FAM. Tube 1.2 shows direct labeling of HaloTag with the FAM-HaloTag Ligand (structure shown in FIG. 10A). Tube 1.3 shows two-step labeling occurs with an azide appended suicide substrate (JRW-1022) and DBCO-FAM (structure shown in FIG. 10A). Tube 1.4 shows little to no labeling with a DBCO appended suicide substrate (JRW-1549) and Azide-FAM. Tube 1.5 shows little to no labeling with an SE-DBCO and Azide-FAM with available lysines on the protein. Tube 2.1 shows two-step labeling occurs between TCO-HaloTag ligand (JRW-1567) and tetrazine-FAM (JRW-1577). Tube 2.2 shows direct labeling of HaloTag with the FAM-HaloTag Ligand. Tube 2.3 shows two-step labeling of NanoLuc with TCO appended suicide substrate (JRW-1566) and tetrazine-FAM (JRW-1577). Tube 2.4 shows two-step labeling with available lysines with SE-TCO and tetrazine-FAM (JRW-1577) on the protein. The SDS-PAGE gel is shown in FIG. 12B and results of a band volume analysis are shown in FIG. 12C.

The data from both examples demonstrates two step labeling with azide appended ligands and a DBCO-FAM. Experiments with DBCO appended ligands does not show labeling with azide appended ligands. Two-step labeling with TCO appended ligands is demonstrated with tetrazine appended ligands. Although direct labeling appears more efficient with these configurations, suicide substrates with TCO and tetrazine-FAM is almost equivalent as direct labeling and much more efficient than the DCBO ligands with azide-FAM and azide ligands and DBCO-FAM.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A method of detecting an *Oplophorus*-derived luciferase in a sample, the method comprising contacting the sample with a compound of m formula (I):

(I)

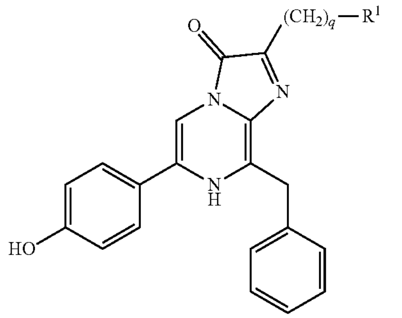

or a tautomer or a salt thereof, wherein:

$R^1$ is optionally substituted aryl, optionally substituted heteroaryl, optionally substituted heterocycle, or optionally substituted cycloalkyl, wherein $R^1$ is substituted with at least one group that is -Q-L-Z;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y}$—$CR^{1x}R^{1y}$—$O)_{t1}$—$(CR^{1x}R^{1y})_{t2}$—$O^1$—, —$CR^{1x}R^{1y})_{t2}$-A-$(CR^{1x}R^{1y}$—$CR^{1x}R^{1y}$—$O)_{t1}$-$Q^1$-, wherein each $Q^1$ is independently a bond, —O—, or —$NR^{Q1}$—, and A is a bond, —O—, —$NR^Q$—, —$NR^Q$—CO—, —CO—$NR^Q$—, —O—CO—$NR^Q$—, or —$NR^Q$—CO—O—;

Z is —$COOR^2$, —$SO_2$—$OR^3$, —$PO(OR^4)(OR^5)$, halo, azide, $C_2$-$C_{10}$ alkynyl, a biotin moiety, —$NR^6R^7$, or —$NR^8$—CO—$R^9$;

$R^2$, $R^3$, $R^4$, $R^5$, $R^8$, $R^9$, $R^{10}$, $R^{11}$, and $R^{12}$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1, 2, 3, 4, 5, 6, 7, 8, 9, 10, 11, or 12;

t1 at each occurrence is independently 1, 2, 3, 4, 5, 6, 7, 8, 9, or 10; and t2 is an integer from 0-5;

wherein, when a group is optionally substituted, it is either unsubstituted or substituted with one or more substituents independently selected from halogen, =O, =S, cyano, nitro, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, aryloxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, amide, carbamate, and acyl; and wherein the compound is not 4-[4-[[8-benzyl-6-(4-hydroxyphenyl)-3-oxo-7H-imidazo[1,2-a]pyrazin-2-yl] methyl]phenoxy]butanoic acid.

2. The method of claim 1, further comprising detecting luminescence in the sample.

3. A method of detecting luminescence in a sample, the method comprising:

(a) contacting the sample with a compound of formula (I):

(I)

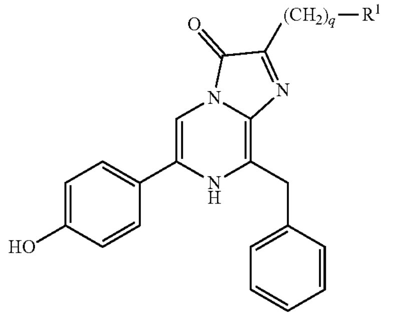

or a tautomer or a salt thereof, wherein:

$R^1$ is optionally substituted aryl, optionally substituted heteroaryl, optionally substituted heterocycle, or optionally substituted cycloalkyl, wherein $R^1$ is substituted with at least one group that is -Q-L-Z;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y}$—$CR^{1x}R^{1y}$—$O)_{t1}$—$(CR^{1x}R^{1y})_{t2}$-$Q^1$-, —$(CR^{1x}R^{1y})_{t2}$-A-$(CR^{1x}R^{1y}$—$CR^{1x}R^{1y}$—$O)_{t1}$-$Q^1$-, wherein each $Q^1$ is independently a bond, —O—, or —$NR^{Q1}$—, and A is a bond, —O—, —$NR^Q$—, —$NR^Q$—CO—, —CO—$NR^Q$—, —O—CO—$NR^Q$—, or —$NR^Q$—CO—O—;

Z is —$COOR^2$, —$SO_2$—$OR^3$, —$PO(OR^4)(OR^5)$, halo, azide, $C_2$-$C_{10}$ alkynyl, a biotin moiety, —$NR^6R^7$, or —$NR^8$—CO—$R^9$;

$R^2$, $R^3$, $R^4$, $R^5$, $R^8$, $R^9$, $R^{10}$, $R^{11}$, and $R^{12}$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1, 2, 3, 4, 5, 6, 7, 8, 9, 10, 11, or 12;

t1 at each occurrence is independently 1, 2, 3, 4, 5, 6, 7, 8, 9, or 10; and t2 is an integer from 0-5;

wherein, when a group is optionally substituted, it is either unsubstituted or substituted with one or more substituents independently selected from halogen, =O, =S, cyano, nitro, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, aryloxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, amide, carbamate, and acyl; and wherein the compound is not 4-[4-[[8-benzyl-6-(4-hydroxyphenyl)-3-oxo-7H-imidazo[1,2-a]pyrazin-2-yl] methyl]phenoxy]butanoic acid;

(b) contacting the sample with an *Oplophorus*-derived luciferase, if it is not present in the sample; and (c) detecting luminescence in the sample.

4. The method of claim 1, wherein the *Oplophorus*-derived luciferase comprises a polypeptide sequence of SEQ ID NO: 2.

5. A method of modulating luminescence of an *Oplophorus*-derived luciferase in a sample, the method comprising (a) contacting the sample with a coelenterazine substrate and the compound of formula (I):

(I)

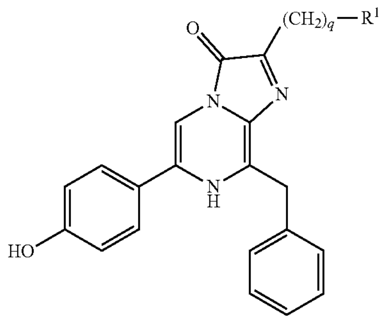

or a tautomer or a salt thereof, wherein:

$R^1$ is optionally substituted aryl, optionally substituted heteroaryl, optionally substituted heterocycle, or optionally substituted cycloalkyl, wherein $R^1$ is substituted with at least one group that is -Q-L-Z:

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$—, —$(CR^{1x}R^{1y}$—$CR^{1x}R^{1y}$—$O)_{t1}$—$CR^{1x}R^{1y})_{t2}$-$Q^1$-, —$(CR^{1x}R^{1y})_{t2}$-A-$(CR^{1x}R^{1y}$—$CR^{1x}R^{1y}$—$O)_{t1}$-$Q^1$-, wherein each $Q^1$ is independently a bond, —O—, or —$NR^{Q1}$—, and A is a bond, —O—, —$NR^Q$—, —$NR^Q$—CO—, —CO—$NR^Q$—, —O—CO—$NR^Q$—, or —$NR^Q$—CO—O—;

Z is —$COOR^2$, —$SO_2$—$OR^3$, —$PO(OR^4)(OR^5)$, halo, azide, $C_2$-$C_{10}$ alkynyl, a biotin moiety, —$NR^6R^7$, or —$NR^8$—CO—$R^9$;

$R^2$, $R^3$, $R^4$, $R^5$, $R^8$, $R^9$, $R^{10}$, $R^{11}$, and $R^{12}$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, optionally substituted heterocycle, optionally substituted heteroalkyl, or an energy acceptor; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1, 2, 3, 4, 5, 6, 7, 8, 9, 10, 11, or 12;

t1 at each occurrence is independently 1, 2, 3, 4, 5, 6, 7, 8, 9, or 10; and t2 is an integer from 0-5;

wherein, when a group is optionally substituted, it is either unsubstituted or substituted with one or more substituents independently selected from halogen, =O, =S, cyano, nitro, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, aryloxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, amide, carbamate, and acyl; and wherein the compound is not 4-[4-[[8-benzyl-6-(4-hydroxyphenyl)-3-oxo-7H-imidazo[1,2-a]pyrazin-2-yl]methyl]phenoxy]butanoic acid; and (b) detecting luminescence in the sample, wherein the compound of formula (I) causes a decrease in the luminescence from the *Oplophorus*-derived luciferase.

6. The method of claim 5, comprising contacting the sample with the coelenterazine substrate prior to contacting the sample with the compound of formula (I).

7. The method of claim 5, comprising contacting the sample with the compound of formula (I) prior to contacting the sample with the coelenterazine substrate.

8. The method of claim 1, wherein the sample comprises a cell.

9. The method of claim 8, wherein the cell comprises the *Oplophorus*-derived luciferase.

10. The method of claim 9, wherein the cell expresses the *Oplophorus*-derived luciferase.

11. The method of claim 5, wherein the coelenterazine substrate is selected from a coelenterazine, coelenterazine derivatives, coelenterazine analogs, pro-coelenterazine, and quinone-masked coelenterazine.

12. The method of claim 3, wherein the *Oplophorus*-derived luciferase comprises a polypeptide sequence of SEQ ID NO: 2.

13. The method of claim 5, wherein the *Oplophorus*-derived luciferase comprises a polypeptide sequence of SEQ ID NO: 2.

14. The method of claim 3, wherein the sample comprises a cell.

15. The method of claim 14, wherein the cell comprises the *Oplophorus*-derived luciferase.

16. The method of claim 15, wherein the cell expresses the *Oplophorus*-derived luciferase.

17. The method of claim 5, wherein the sample comprises a cell.

18. The method of claim 17, wherein the cell comprises the *Oplophorus*-derived luciferase.

19. The method of claim 18, wherein the cell expresses the *Oplophorus*-derived luciferase.

20. The method of claim 5, wherein the modulating comprises inhibiting *Oplophorus*-derived luciferase activity in the sample.

21. The method of claim 1, wherein the compound of formula (I) is selected from the group consisting of:

2-(4-((6-aminohexyl)oxy)-3-fluorobenzyl)-8-benzyl-6-(4-hydroxyphenyl)imidazo[1,2-a]pyrazin-3(7H)-one;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-bis(dimethylamino)-3-oxo-3H-spiro[isobenzofuran-1,9'-xanthene]-6-carboxamide;

6-(4-((8-benzyl-6-(4-hydroxyphenyl)-3-oxo-3,7-dihydroimidazo[1,2-a]pyrazin-2-yl)methyl)-2-fluorophenoxy)hexane-1-sulfonic acid;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-dihydroxy-3-oxo-3H-spiro[isobenzofuran-1,9'-xanthene]-6-carboxamide;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3-(5,5-difluoro-7-(1H-pyrrol-2-yl)-5H-514,614-dipyrrolo[1,2-c:2',1'-f][1,3,2]diazaborinin-3-yl)propanamide;

N,N-(6-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-3-oxo-3H-spiro[isobenzofuran-1,9'-xanthene]-3',6'-diyl)bis(2,2,2-trifluoroacetamide);

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-dihydroxy-3-oxo-3H-spiro[isobenzofuran-1,9'-xanthene]-6-carboxamide;

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-bis(dimethylamino)-3-oxo-3H-spiro[isobenzofuran-1,9'-xanthene]-6-carboxamide;

3-(2-(2-aminoethoxy)ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-dihydroxy-3-oxo-3H-spiro[isobenzofuran-1,9'-xanthene]-6-carboxamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-bis(dimethylamino)-3-oxo-3H-spiro[isobenzofuran-1,9'-xanthene]-6-carboxamide;

6-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-3-oxo-3H-spiro[isobenzofuran-1,9'-xanthene]-3',6'-diyl diacetate;

2-(4-((6-azidohexyl)oxy)-3-fluorobenzyl)-8-benzyl-6-(4-hydroxyphenyl)imidazo[1,2-a]pyrazin-3(7H)-one;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(2,7-difluoro-3,6-dihydroxyxanthylium-9-yl)benzoate;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,11-dihydroxydibenzo[c,h]xanthen-14-ium-7-yl)benzoate; and N1-(8-(4-((8-benzyl-6-(4-hydroxyphenyl)-3-oxo-3,7-dihydroimidazo[1,2-a]pyrazin-2-yl)methyl)-2-fluorophenoxy)octyl)-N4-(2-(5,5-difluoro-1,3-dimethyl-5H-$5\lambda^4$,$6\lambda^4$-dipyrrolo[1,2-c:2',1'-f][1,3,2]diazaborinin-10-yl)ethyl)succinamide, or a tautomer or a salt thereof.

22. The method of claim 3, wherein the compound of formula (I) is selected from the group consisting of:

2-(4-((6-aminohexyl)oxy)-3-fluorobenzyl)-8-benzyl-6-(4-hydroxyphenyl)imidazo[1,2-a]pyrazin-3(7H)-one;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-bis(dimethylamino)-3-oxo-3H-spiro[isobenzofuran-1,9'-xanthene]-6-carboxamide;

6-(4-((8-benzyl-6-(4-hydroxyphenyl)-3-oxo-3,7-dihydroimidazo[1,2-a]pyrazin-2-yl)methyl)-2-fluorophenoxy)hexane-1-sulfonic acid;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-dihydroxy-3-oxo-3H-spiro[isobenzofuran-1,9'-xanthene]-6-carboxamide;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3-(5,5-difluoro-7-(1H-pyrrol-2-yl)-5H-514,614-dipyrrolo[1,2-c:2',1'-f][1,3,2]diazaborinin-3-yl)propanamide;

N,N-(6-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-3-oxo-3H-spiro[isobenzofuran-1,9'-xanthene]-3',6'-diyl)bis(2,2,2-trifluoroacetamide);

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-dihydroxy-3-oxo-3H-spiro[isobenzofuran-1,9'-xanthene]-6-carboxamide;

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-bis(dimethylamino)-3-oxo-3H-spiro[isobenzofuran-1,9'-xanthene]-6-carboxamide;

3-(2-(2-aminoethoxy)ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-dihydroxy-3-oxo-3H-spiro[isobenzofuran-1,9'-xanthene]-6-carboxamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-bis(dimethylamino)-3-oxo-3H-spiro[isobenzofuran-1,9'-xanthene]-6-carboxamide;

6-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-3-oxo-3H-spiro[isobenzofuran-1,9'-xanthene]-3',6'-diyl diacetate;

2-(4-((6-azidohexyl)oxy)-3-fluorobenzyl)-8-benzyl-6-(4-hydroxyphenyl)imidazo[1,2-a]pyrazin-3(7H)-one;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(2,7-difluoro-3,6-dihydroxyxanthylium-9-yl)benzoate;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,11-dihydroxydibenzo[c,h]xanthen-14-ium-7-yl)benzoate; and N1-(8-(4-((8-benzyl-6-(4-hydroxyphenyl)-3-oxo-3,7-dihydroimidazo[1,2-a]pyrazin-2-yl)methyl)-2-fluorophenoxy)octyl)-N4-(2-(5,5-difluoro-1,3-dimethyl-5H-$5\lambda^4$,$6\lambda^4$-dipyrrolo[1,2-c:2',1'-f][1,3,2]diazaborinin-10-yl)ethyl)succinamide, or a tautomer or a salt thereof.

23. The method of claim 5, wherein the compound of formula (I) is selected from the group consisting of:

2-(4-((6-aminohexyl)oxy)-3-fluorobenzyl)-8-benzyl-6-(4-hydroxyphenyl)imidazo[1,2-a]pyrazin-3(7H)-one;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-bis(dimethylamino)-3-oxo-3H-spiro[isobenzofuran-1,9'-xanthene]-6-carboxamide;

6-(4-((8-benzyl-6-(4-hydroxyphenyl)-3-oxo-3,7-dihydroimidazo[1,2-a]pyrazin-2-yl)methyl)-2-fluorophenoxy)hexane-1-sulfonic acid;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3',6'-dihydroxy-3-oxo-3H-spiro[isobenzofuran-1,9'-xanthene]-6-carboxamide;

N-(6-(4-((8-benzyl-6-(4-hydroxyphenyl)-3-oxo-3,7-dihydroimidazo[1,2-a]pyrazin-2-yl)methyl)-2-fluorophenoxy)hexyl)-3-(5,5-difluoro-7-(1H-pyrrol-2-yl)-5H-514,614-dipyrrolo[1,2-c:2',1'-f][1,3,2]diazaborinin-3-yl)propanamide;

N,N-(6-((6-(4-((8-benzyl-6-(4-hydroxyphenyl)-3-oxo-3,7-dihydroimidazo[1,2-a]pyrazin-2-yl)methyl)-2-fluorophenoxy)hexyl)carbamoyl)-3-oxo-3H-spiro[isobenzofuran-1,9'-xanthene]-3',6'-diyl)bis(2,2,2-trifluoroacetamide);

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-dihydroxy-3-oxo-3H-spiro[isobenzofuran-1,9'-xanthene]-6-carboxamide;

N-(8-(4-((8-benzyl-6-(4-hydroxyphenyl)-3-oxo-3,7-dihydroimidazo[1,2-a]pyrazin-2-yl)methyl)-2-fluorophenoxy)octyl)-3',6'-bis(dimethylamino)-3-oxo-3H-spiro[isobenzofuran-1,9'-xanthene]-6-carboxamide;

3-(2-(2-aminoethoxy)ethoxy)-N-(8-(4-((1-benzyl-3-(4-hydroxyphenyl)-6-oxo-2,6-dihydropyrrolo[1,2-a]pyrazin-7-yl)methyl)-2-fluorophenoxy)octyl)propanamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-dihydroxy-3-oxo-3H-spiro[isobenzofuran-1,9'-xanthene]-6-carboxamide;

N-(2-(2-(3-((8-(4-((1-benzyl-3-(4-hydroxyphenyl)-6-oxo-2,6-dihydropyrrolo[1,2-a]pyrazin-7-yl)methyl)-2-fluorophenoxy)octyl)amino)-3-oxopropoxy)ethoxy)ethyl)-3',6'-bis(dimethylamino)-3-oxo-3H-spiro[isobenzofuran-1,9'-xanthene]-6-carboxamide;

6-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-3-oxo-3H-spiro[isobenzofuran-1,9'-xanthene]-3',6'-diyl diacetate;

2-(4-((6-azidohexyl)oxy)-3-fluorobenzyl)-8-benzyl-6-(4-hydroxyphenyl)imidazo[1,2-a]pyrazin-3(7H)-one;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(2,7-difluoro-3,6-dihydroxyxanthylium-9-yl)benzoate;

5-((8-(4-((8-benzyl-6-(4-hydroxyphenyl)-3-oxo-3,7-dihydroimidazo[1,2-a]pyrazin-2-yl)methyl)-2-fluorophenoxy)octyl)carbamoyl)-2-(3,11-dihydroxydibenzo[c,h]xanthen-14-ium-7-yl)benzoate; and N1-(8-(4-((8-benzyl-6-(4-hydroxyphenyl)-3-oxo-3,7-dihydroimidazo[1,2-a]pyrazin-2-yl)methyl)-2-fluorophenoxy)octyl)-N4-(2-(5,5-difluoro-1,3-dimethyl-5H-5$\lambda^4$,6$\lambda^4$-dipyrrolo[1,2-c:2',1'-f][1,3,2]diazaborinin-10-yl)ethyl)succinamide, or a tautomer or a salt thereof.

* * * * *

SEQUENCE LISTING

```
Sequence total quantity: 5
SEQ ID NO: 1          moltype = AA  length = 169
FEATURE               Location/Qualifiers
source                1..169
                      mol_type = protein
                      organism = Oplophorus gracilirostris
SEQUENCE: 1
FTLADFVGDW QQTAGYNQDQ VLEQGGLSSL FQALGVSVTP IQKVVLSGEN GLKADIHVII  60
PYEGLSGFQM GLIEMIFKVV YPVDDHHFKI ILHYGTLVID GVTPNMIDYF GRPYPGIAVF  120
DGKQITVTGT LWNGNKIYDE RLINPDGSLL FRVTINGVTG WRLCENILA             169

SEQ ID NO: 2          moltype = AA  length = 171
```

-continued

```
FEATURE                Location/Qualifiers
source                 1..171
                       mol_type = protein
                       organism = Synthetic construct
SEQUENCE: 2
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171

SEQ ID NO: 3           moltype = AA  length = 11
FEATURE                Location/Qualifiers
source                 1..11
                       mol_type = protein
                       organism = Synthetic construct
SEQUENCE: 3
VSGWRLFKKI S                                                       11

SEQ ID NO: 4           moltype = AA  length = 158
FEATURE                Location/Qualifiers
source                 1..158
                       mol_type = protein
                       organism = Synthetic construct
SEQUENCE: 4
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTIN                          158

SEQ ID NO: 5           moltype = AA  length = 297
FEATURE                Location/Qualifiers
source                 1..297
                       mol_type = protein
                       organism = Synthetic construct
SEQUENCE: 5
MAEIGTGFPF DPHYVEVLGE RMHYVDVGPR DGTPVLFLHG NPTSSYVWRN IIPHVAPTHR  60
CIAPDLIGMG KSDKPDLGYF FDDHVRFMDA FIEALGLEEV VLVIHDWGSA LGFHWAKRNP  120
ERVKGIAFME FIRPIPTWDE WPEFARETFQ AFRTTDVGRK LIIDQNVFIE GTLPMGVVRP  180
LTEVEMDHYR EPFLNPVDRE PLWRFPNELP IAGEPANIVA LVEEYMDWLH QSPVPKLLFW  240
GTPGVLIPPA EAARLAKSLP NCKAVDIGPG LNLLQEDNPD LIGSEIARWL STLEISG     297
```